(12) United States Patent
Oz et al.

(10) Patent No.: US 10,039,459 B2
(45) Date of Patent: *Aug. 7, 2018

(54) CONTINUOUS NON-INVASIVE MONITORING OF A PREGNANT HUMAN SUBJECT

(71) Applicant: Nuvo Group Ltd., Ramat Gan (IL)

(72) Inventors: Oren Oz, Modiin (IL); Ilya Divinsky, Tel Aviv (IL); Muhammad Mhajna, Umm al Fahem (IL); Elad Knoll, Tel Aviv (IL); Amit Kam, Tel Aviv (IL); Nathan Intrator, Tel Aviv (IL)

(73) Assignee: Nuvo Group Ltd., Ramat Gan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/389,618

(22) Filed: Dec. 23, 2016

(65) Prior Publication Data

US 2017/0172426 A1    Jun. 22, 2017

Related U.S. Application Data

(63) Continuation of application No. 15/072,051, filed on Mar. 16, 2016, now Pat. No. 9,572,504, which is a continuation-in-part of application No. 14/921,489, filed on Oct. 23, 2015, now Pat. No. 9,392,952.

(60) Provisional application No. 62/133,485, filed on Mar. 16, 2015.

(51) Int. Cl.
| *A61B 5/0245* | (2006.01) |
| *A61B 5/00* | (2006.01) |
| *A61B 5/024* | (2006.01) |
| *A61B 5/04* | (2006.01) |
| *A61B 5/0402* | (2006.01) |
| *A61B 5/0408* | (2006.01) |
| *A61B 5/0444* | (2006.01) |
| *A61B 5/0452* | (2006.01) |

(52) U.S. Cl.
CPC .......... *A61B 5/0245* (2013.01); *A61B 5/0022* (2013.01); *A61B 5/02405* (2013.01); *A61B 5/02411* (2013.01); *A61B 5/0402* (2013.01); *A61B 5/04014* (2013.01); *A61B 5/04017* (2013.01); *A61B 5/0444* (2013.01); *A61B 5/04085* (2013.01); *A61B 5/04525* (2013.01); *A61B 5/6823* (2013.01); *A61B 5/7203* (2013.01); *A61B 5/7225* (2013.01); *A61B 2562/0204* (2013.01); *A61B 2562/0209* (2013.01)

(58) Field of Classification Search
CPC ... A61B 5/0245; A61B 5/022; A61B 5/02411; A61B 5/0402; A61B 5/04085; A61B 5/0428; A61B 5/0444; A61B 5/04362; A61B 5/04; A61B 5/7225
See application file for complete search history.

(56) References Cited

U.S. PATENT DOCUMENTS

| 7,474,915 | B2* | 1/2009 | Assaleh | A61B 5/0444 600/508 |
| 8,892,181 | B2* | 11/2014 | Wolfberg | A61B 5/0444 600/391 |
| 9,572,504 | B2* | 2/2017 | Oz | A61B 5/0245 |

(Continued)

*Primary Examiner* — Catherine Voorhees
(74) *Attorney, Agent, or Firm* — Greenberg Traurig, LLP

(57) ABSTRACT

The invention provides systems and methods for monitoring the wellbeing of a fetus by the non-invasive detection and analysis of fetal cardiac electrical activity data.

10 Claims, 55 Drawing Sheets

(56) References Cited

U.S. PATENT DOCUMENTS

| | | | |
|---|---|---|---|
| 9,579,055 B1* | 2/2017 | Rood | A61B 5/4362 |
| 2005/0267377 A1* | 12/2005 | Marossero | A61B 5/02411 |
| | | | 600/511 |
| 2011/0098586 A1* | 4/2011 | Kabakov | A61B 5/02411 |
| | | | 600/511 |
| 2012/0232398 A1* | 9/2012 | Roham | A61B 8/0866 |
| | | | 600/453 |

* cited by examiner

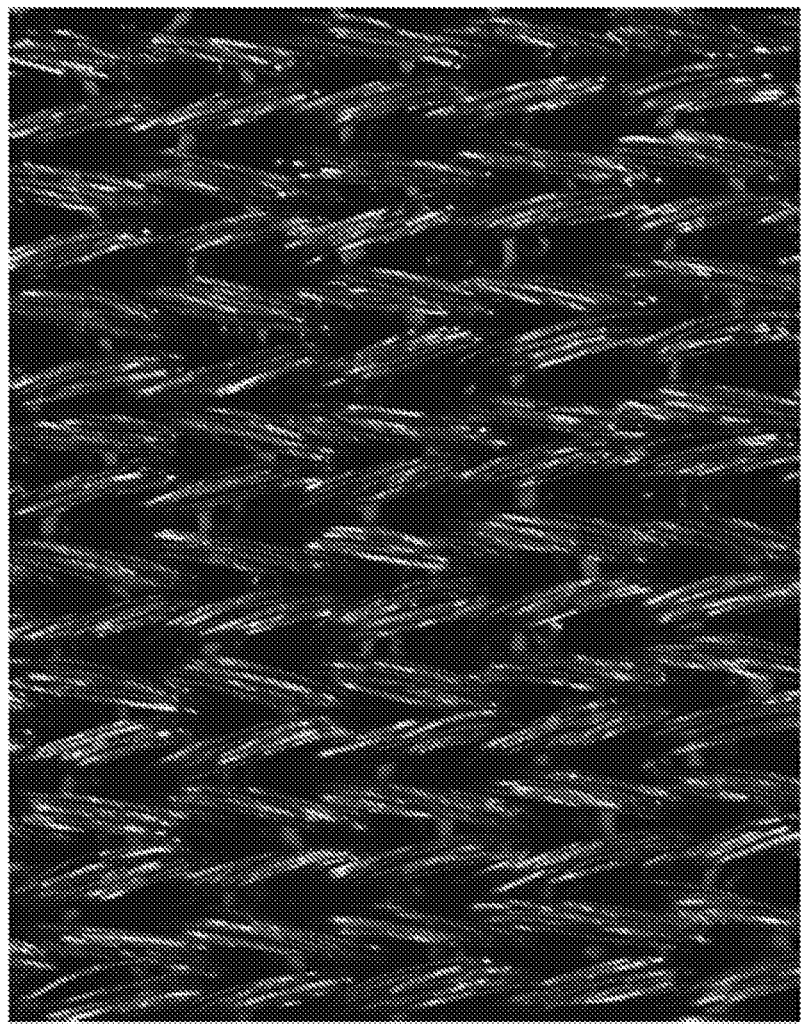
Main direction
Figure 10

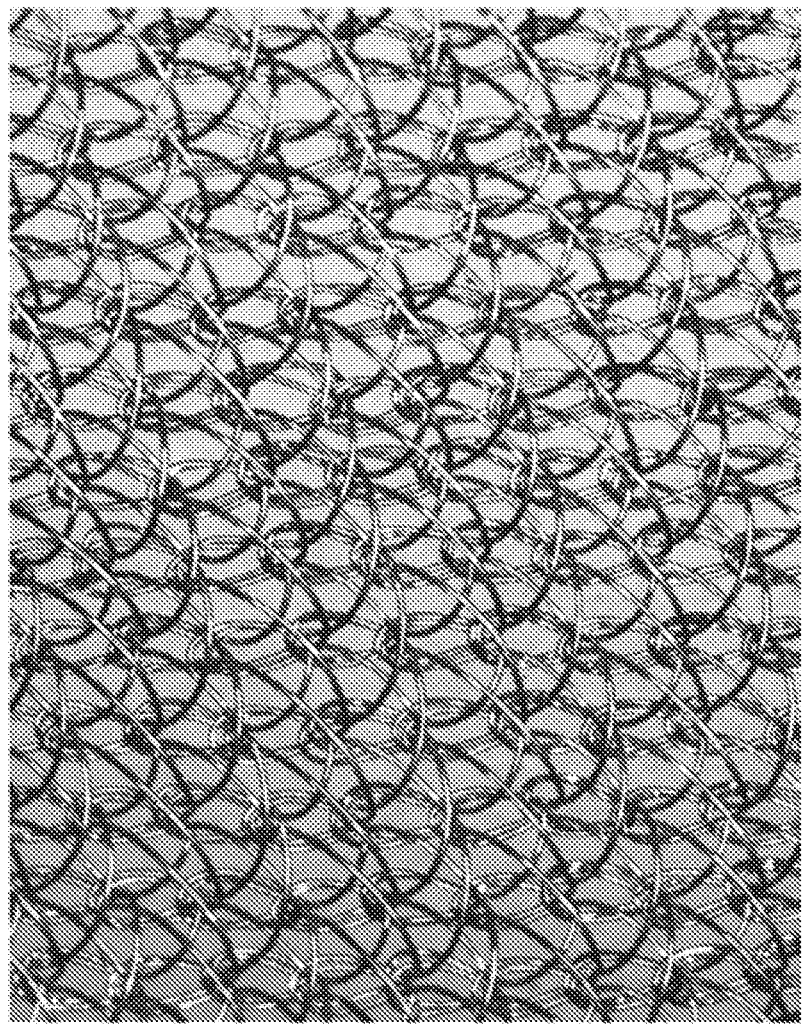
Figure 14

Figure 39
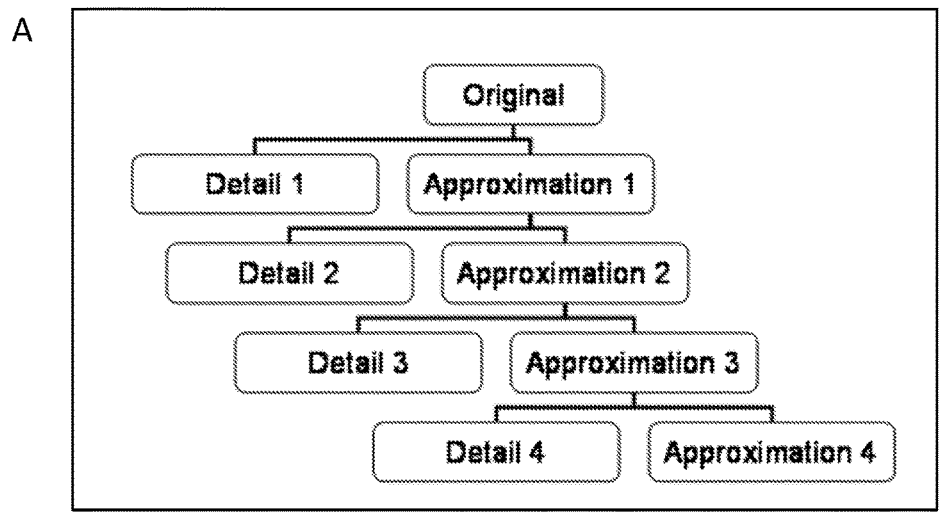
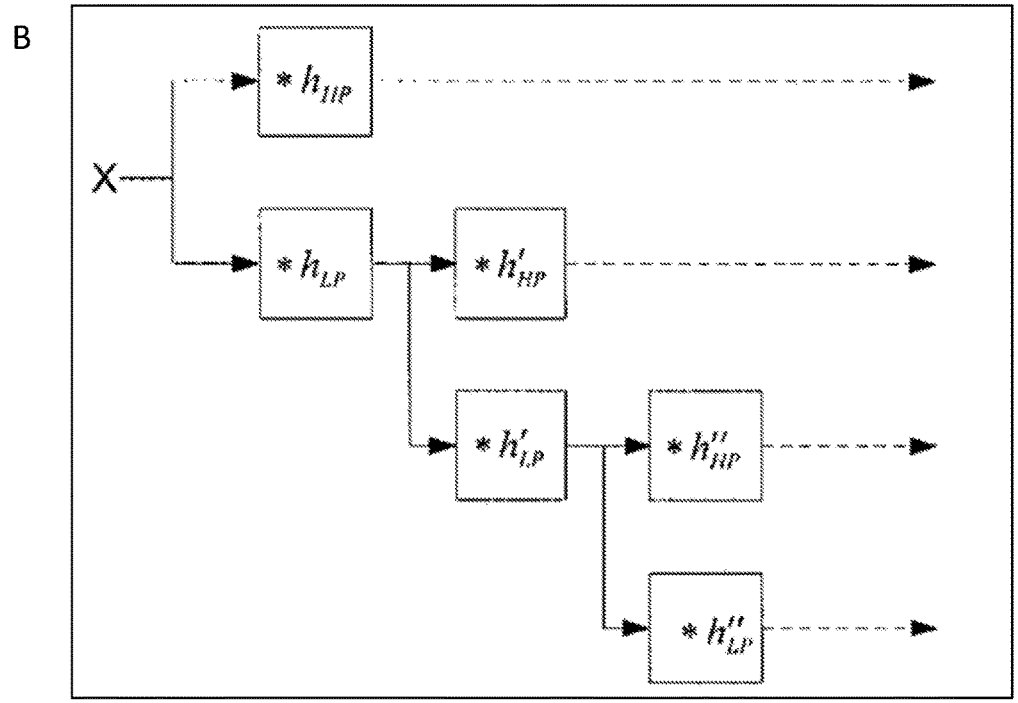

CONTINUOUS NON-INVASIVE MONITORING OF A PREGNANT HUMAN SUBJECT

CROSS REFERENCE TO RELATED APPLICATIONS

This application is a continuation of U.S. application Ser. No. 15/072,051, filed Mar. 16, 2016, which is a continuation-in-part of U.S. patent application Ser. No. 14/921,489, filed on Oct. 23, 2015, patented on Jul. 19, 2016 and issued U.S. Pat. No. 9,392,952, which claims priority to U.S. Provisional Patent Application Ser. No. 62/133,485, filed on Mar. 16, 2015, the entire contents of which are incorporated by reference in their entirety.

FIELD OF THE INVENTION

This invention relates to apparatuses, systems and methods for continuous, non-invasive monitoring of a fetus and/or mother using from multiple sensors that collect maternal and fetal cardiac signals data.

BACKGROUND

Monitoring maternal and fetal cardiac activity can be useful to determine of the health of a fetus and the mother during pregnancy.

SUMMARY

In one embodiment, the present invention provides a garment that includes:
a) at least one electrocardiogram sensor configured to contact the skin of the abdomen of a pregnant human subject and detect fetal and maternal cardiac electrical activity;
b) at least one acoustic sensor configured to contact the skin of the abdomen of a pregnant human subject and detect fetal and maternal cardiac electrical activity; and
c) a garment configured to position and contact the at least one electrocardiogram sensor and the at least one acoustic sensor on the abdomen of the pregnant human subject.

In one embodiment, the garment is further configured to include:
d) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving raw Electrocardiogram (ECG) signals data from the at least one pair of ECG sensors; wherein the at least one pair of ECG sensors is positioned in on an abdomen of a pregnant human subject; wherein the raw ECG signals data comprise data representative of a N number of raw ECG signals (raw N-ECG signals data) which are being acquired in real-time from the at least one pair of ECG sensors; digital signal filtering the raw ECG signals data to form filtered N-ECG signals data having filtered N-ECG signals; detecting maternal heart peaks in each of the filtered N-ECG signal in the filtered N-ECG signals data; subtracting, from each of the filtered N-ECG signal of the filtered N-ECG signals data, the maternal ECG signal, by utilizing at least one non-linear subtraction procedure to obtain corrected ECG signals data which comprise data representative of a N number of corrected ECG signals (corrected N-ECG signals data), wherein the at least one non-linear subtraction procedure comprises: iteratively performing: i) dividing each filtered N-ECG signal of N-ECG signals of the filtered N-ECG signals data into a second plurality of ECG signal segments,) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) modifying each of the plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being; 2) setting a set of tentative values for a local template for each filtered N-ECG signal segment; and 3) utilizing at least one optimization scheme to determine an adaptive template for each filtered N-ECG signal segment based on the local template being matched to the global template within a pre-determined similarity value; and iii) eliminating the modified segments from each of the filtered N-ECG signals, by subtracting the adaptive template from the filtered N-ECG signal thereby generating each corrected ECG signal; extracting raw fetal ECG signals data from the filtered N-ECG signals data based on the corrected ECG signals data, wherein the raw fetal ECG signals data comprises a N number of fetal ECG signals (raw N-ECG fetal signals data); processing the raw N-ECG fetal signals data to improve a signal-to-noise ratio of the N-ECG fetal signals to form filtered N-ECG fetal signals data; detecting fetal heart peaks in the filtered N-ECG fetal signals data; calculating, based on detected fetal heart peaks, at least one of: i) fetal heart rate, ii) fetal heart curve, iii) beat-2-beat fetal heart rate, or iv) fetal heart rate variability; and outputting a result of the calculating operation;
e) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving, by at least one computer processor executing specific programmable instructions configured for the method, a plurality of Phonocardiogram (PCG) signals data inputs from a plurality of acoustic sensors; digital signal filtering, by the at least one computer processor, utilizing a plurality of bandpass filters, the plurality of PCG signals data inputs to form a plurality of filtered PCG outputs, wherein the plurality of bandpass filters comprises a L number of bandpass filters, wherein each bandpass filter outputs a K number of filtered PCG outputs; wavelet denoising, by the at least one computer processor, a first subset of filtered PCG outputs of the plurality of filtered PCG outputs to form a M number of denoised filtered PCG outputs, wherein M is equal to L multiply by K; transforming, by the at least one computer processor, utilizing an Independent-Component-Analysis (ICA), a second subset of filtered PCG outputs of the plurality of filtered PCG outputs to form the M number of filtered ICA transforms; transforming, by the at least one computer processor, utilizing the Independent-Component-Analysis (ICA), a first portion of the second subset of denoised filtered PCG outputs to form the M number of denoised filtered ICA transforms; compiling, by the at least one computer processor, a S number of a plurality of detection heartbeat (DH) inputs, comprising: i) the M number of filtered PCG outputs, ii) the M number of the denoised filtered PCG outputs, iii) the M number of the filtered ICA transforms, and iv) the M number of the denoised filtered ICA transforms; detecting, by the at least one computer processor, beat locations of beats in each of DH inputs; calculating, by the at least one computer processor, a confidence score that describes a probability that the beats in each DH input of the plurality of DH inputs represent actual heartbeats and not a noise; dividing, by the at least one computer processor, the plurality of DH inputs into at least two groups: i) a first group of DH inputs containing fetal heartbeats, ii) a second group of DH inputs containing maternal heartbeats; selecting, by the at least one computer processor, from the first group of DH inputs, at least one particular fetal DH input that contains the fetal heartbeat based on a first confidence score of the at least one particular fetal DH input; and selecting, by the at least one computer processor, from the second group of DH inputs, at least one particular maternal DH input that contains the maternal heartbeat, based on a second confidence score of the at least one particular maternal DH input;

f) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations:
  i. receiving a calculated fetal heart rate for a plurality of time points over a particular time interval from filtered N-ECG fetal signals data and a calculated fetal heart rate for a plurality of time points over a particular time interval from filtered PCG outputs;
  ii. determining the score of the calculated fetal heart rate for the plurality of time points over the particular time interval for the filtered N-ECG fetal signals;
  iii. determining the score of the calculated fetal heart rate for the plurality of time points over the particular time interval for the filtered PCG outputs;
  iv. based on the calculated fetal heart rate and score for a plurality of time points over a particular time interval from filtered N-ECG fetal signals data, and the calculated fetal heart rate and score for a plurality of time points over a particular time interval from filtered PCG outputs, determining a consolidated fetal heart rate and score for the plurality of time points over the particular time interval,
    wherein the consolidated fetal heart rate and score for an individual time point within the plurality of time points is determined as one of the four options selected from the group consisting of:
      1. the weighted average of the calculated heart rate from the filtered N-ECG fetal signals data and the filtered PCG outputs for the individual time point, if the calculated heart rate from the filtered N-ECG fetal signals data and the filtered PCG outputs for the individual time point differs by 10 beats per minute or less, and if the scores of the calculated fetal heart rate for the individual time point for both the filtered N-ECG fetal signals data and the filtered PCG outputs are valid;
      2. the calculated heart rate having the lower score, if the calculated heart rate from the filtered N-ECG fetal signals data and the filtered PCG outputs for the individual time point differs by more than 10 beats per minute, and if the scores of the calculated fetal heart rate for the individual time point for both the filtered N-ECG fetal signals data and the filtered PCG outputs are valid;
      3. the calculated heart rate that has the valid score; and
      4. no consolidated fetal heart rate and score, if neither the calculated heart rate from the filtered N-ECG fetal signals data or the filtered PCG outputs has a valid score;
  v. based on the consolidated heart rate and scores for the plurality of time points over the particular time interval, generating, by the at least one computer processor, a fetal heart rate probability mesh;
  vi. based on the fetal heart rate probability mesh, generating, by the at least one computer processor, an estimated fetal heart rate over the particular time interval,
    wherein the estimated fetal heart rate over the particular time interval is calculated based on (1) cost representing fetal heart probability mesh values at each point of the estimated fetal heart rate over the particular time interval; and (2) cost representing the overall tortuosity of the estimated fetal heart rate over the particular time interval.

In one embodiment, the garment is a belt.

In one embodiment, the present invention provides a system for monitoring maternal and fetal cardiac activity that includes:
a) at least one electrocardiogram sensor configured to contact the skin of the abdomen of a pregnant human subject and detect fetal and maternal cardiac electrical activity;
b) at least one acoustic sensor configured to contact the skin of the abdomen of a pregnant human subject and detect fetal and maternal cardiac electrical activity;
c) a garment configured to position and contact the at least one electrocardiogram sensor and the at least one acoustic sensor on the abdomen of the pregnant human subject;
d) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving raw Electrocardiogram (ECG) signals data from the at least one pair of ECG sensors; wherein the at least one pair of ECG sensors is positioned in on an abdomen of a pregnant human subject; wherein the raw ECG signals data comprise data representative of a N number of raw ECG signals (raw N-ECG signals data) which are being acquired in real-time from the at least one pair of ECG sensors; digital signal filtering the raw ECG signals data to form filtered N-ECG signals data having filtered N-ECG signals; detecting maternal heart peaks in each of the filtered N-ECG signal in the filtered N-ECG signals data; subtracting, from each of the filtered N-ECG signal of the filtered N-ECG signals data, the maternal ECG signal, by utilizing at least one non-linear subtraction procedure to obtain corrected ECG signals data which comprise data representative of a N number of corrected ECG signals (corrected N-ECG signals data), wherein the at least one non-linear subtraction procedure comprises: iteratively performing: i) dividing each filtered N-ECG signal of N-ECG signals of the filtered N-ECG signals data into a second plurality of ECG signal segments,) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) modifying each of the plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being; 2) setting a set of tentative values for a local template for each filtered N-ECG signal segment; and 3) utilizing at least one optimization scheme to determine an adaptive template for each filtered N-ECG signal segment based on the local template being matched to the global template within a pre-determined similarity value; and iii) eliminating the modified segments from each of the filtered N-ECG signals, by subtracting the adaptive template from the filtered N-ECG signal thereby generating each corrected ECG signal; extracting raw fetal ECG signals data from the filtered N-ECG signals data based on the corrected ECG signals data, wherein the raw fetal ECG signals data comprises a N number of fetal ECG signals (raw N-ECG fetal signals data); processing the raw N-ECG fetal signals data to improve a signal-to-noise ratio of the N-ECG fetal signals to form filtered N-ECG fetal signals data; detecting fetal heart peaks in the filtered N-ECG fetal signals data; calculating, based on detected fetal heart peaks, at least one of: i) fetal heart rate, ii) fetal heart curve, iii) beat-2-beat fetal heart rate, or iv) fetal heart rate variability; and outputting a result of the calculating operation;

e) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving, by at least one computer processor executing specific programmable instructions configured for the method, a plurality of Phonocardiogram (PCG) signals data inputs from a plurality of acoustic sensors; digital signal filtering, by the at least one computer processor, utilizing a plurality of bandpass filters, the plurality of PCG signals data inputs to form a plurality of filtered PCG outputs, wherein the plurality of bandpass filters comprises a L number of bandpass filters, wherein each bandpass filter outputs a K number of filtered PCG outputs; wavelet denoising, by the at least one computer processor, a first subset of filtered PCG outputs of the plurality of filtered PCG outputs to form a M number of denoised filtered PCG outputs, wherein M is equal to L multiply by K; transforming, by the at least one computer processor, utilizing an Independent-Component-Analysis (ICA), a second subset of filtered PCG outputs of the plurality of filtered PCG outputs to form the M number of filtered ICA transforms; transforming, by the at least one computer processor, utilizing the Independent-Component-Analysis (ICA), a first portion of the second subset of denoised filtered PCG outputs to form the M number of denoised filtered ICA transforms; compiling, by the at least one computer processor, a S number of a plurality of detection heartbeat (DH) inputs, comprising: i) the M number of filtered PCG outputs, ii) the M number of the denoised filtered PCG outputs, iii) the M number of the filtered ICA transforms, and iv) the M number of the denoised filtered ICA transforms; detecting, by the at least one computer processor, beat locations of beats in each of DH inputs; calculating, by the at least one computer processor, a confidence score that describes a probability that the beats in each DH input of the plurality of DH inputs represent actual heartbeats and not a noise; dividing, by the at least one computer processor, the plurality of DH inputs into at least two groups: i) a first group of DH inputs containing fetal heartbeats, ii) a second group of DH inputs containing maternal heartbeats; selecting, by the at least one computer processor, from the first group of DH inputs, at least one particular fetal DH input that contains the fetal heartbeat based on a first confidence score of the at least one particular fetal DH input; and selecting, by the at least one computer processor, from the second group of DH inputs, at least one particular maternal DH input that contains the maternal heartbeat, based on a second confidence score of the at least one particular maternal DH input;

f) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations:
  i. receiving a calculated fetal heart rate for a plurality of time points over a particular time interval from filtered N-ECG fetal signals data and a calculated fetal heart rate for a plurality of time points over a particular time interval from filtered PCG outputs;
  ii. determining the score of the calculated fetal heart rate for the plurality of time points over the particular time interval for the filtered N-ECG fetal signals;
  iii. determining the score of the calculated fetal heart rate for the plurality of time points over the particular time interval for the filtered PCG outputs;
  iv. based on the calculated fetal heart rate and score for a plurality of time points over a particular time interval from filtered N-ECG fetal signals data, and the calculated fetal heart rate and score for a plurality of time points over a particular time interval from filtered PCG outputs, determining a consolidated fetal heart rate and score for the plurality of time points over the particular time interval,
     wherein the consolidated fetal heart rate and score for an individual time point within the plurality of time points is determined as one of the four options selected from the group consisting of:
     1. the weighted average of the calculated heart rate from the filtered N-ECG fetal signals data and the filtered PCG outputs for the individual time point, if the calculated heart rate from the filtered N-ECG fetal signals data and the filtered PCG outputs for the individual time point differs by 10 beats per minute or less, and if the scores of the calculated fetal heart rate for the individual time point for both the filtered N-ECG fetal signals data and the filtered PCG outputs are valid, determining;
2. the calculated heart rate having the lower score, if the calculated heart rate from the filtered N-ECG fetal signals data and the filtered PCG outputs for the individual time point differs by more than 10 beats per minute, and if the scores of the calculated fetal heart rate for the individual time point for both the filtered N-ECG fetal signals data and the filtered PCG outputs are valid;
3. the calculated heart rate that has the valid score; and
4. no consolidated fetal heart rate and score, if neither the calculated heart rate from the filtered N-ECG fetal signals data or the filtered PCG outputs has a valid score;

v. based on the consolidated heart rate and scores for the plurality of time points over the particular time interval, generating, by the at least one computer processor, a fetal heart rate probability mesh;

vi. based on the fetal heart rate probability mesh, generating, by the at least one computer processor, an estimated fetal heart rate over the particular time interval,
wherein the estimated fetal heart rate over the particular time interval is calculated based on (1) cost representing fetal heart probability mesh values at each point of the estimated fetal heart rate over the particular time interval; and (2) cost representing the overall tortuosity of the estimated fetal heart rate over the particular time interval.

In one embodiment, the present invention provides a system for generating an estimation of fetal cardiac activity that includes:
a) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations:
i. receiving a calculated fetal heart rate for a plurality of time points over a particular time interval from filtered N-ECG fetal signals data and a calculated fetal heart rate for a plurality of time points over a particular time interval from filtered PCG outputs;
ii. determining the score of the calculated fetal heart rate for the plurality of time points over the particular time interval for the filtered N-ECG fetal signals;
iii. determining the score of the calculated fetal heart rate for the plurality of time points over the particular time interval for the filtered PCG outputs;
iv. based on the calculated fetal heart rate and score for a plurality of time points over a particular time interval from filtered N-ECG fetal signals data, and the calculated fetal heart rate and score for a plurality of time points over a particular time interval from filtered PCG outputs, determining a consolidated fetal heart rate and score for the plurality of time points over the particular time interval,
wherein the consolidated fetal heart rate and score for an individual time point within the plurality of time points is determined as one of the four options selected from the group consisting of:
1. the weighted average of the calculated heart rate from the filtered N-ECG fetal signals data and the filtered PCG outputs for the individual time point, if the calculated heart rate from the filtered N-ECG fetal signals data and the filtered PCG outputs for the individual time point differs by 10 beats per minute or less, and if the scores of the calculated fetal heart rate for the individual time point for both the filtered N-ECG fetal signals data and the filtered PCG outputs are valid;
2. the calculated heart rate having the lower score, if the calculated heart rate from the filtered N-ECG fetal signals data and the filtered PCG outputs for the individual time point differs by more than 10 beats per minute, and if the scores of the calculated fetal heart rate for the individual time point for both the filtered N-ECG fetal signals data and the filtered PCG outputs are valid;
3. the calculated heart rate that has the valid score; and
4. no consolidated fetal heart rate and score, if neither the calculated heart rate from the filtered N-ECG fetal signals data or the filtered PCG outputs has a valid score;

v. based on the consolidated heart rate and scores for the plurality of time points over the particular time interval, generating, by the at least one computer processor, a fetal heart rate probability mesh;

vi. based on the fetal heart rate probability mesh, generating, by the at least one computer processor, an estimated fetal heart rate over the particular time interval,
wherein the estimated fetal heart rate over the particular time interval is calculated based on (1) cost representing fetal heart probability mesh values at each point of the estimated fetal heart rate over the particular time interval; and (2) cost representing the overall tortuosity of the estimated fetal heart rate over the particular time interval.

In one embodiment, cost representing fetal heart probability mesh values at each point of the estimated fetal heart rate over the particular time interval; and cost representing the overall tortuosity of the estimated fetal heart rate over the particular time interval is performed, by the at least one computer processor, using dynamic programming, where each value of the accumulated cost mesh is calculated as a sum of the fetal heart rate probability mesh value at that point and of the minimal path in its neighborhood in the previous step, based on:

$$E(i,j)=e(i,j)+\min(E(i-1,j-k)); k=-4:4$$

where:
e is the value of the fetal heart rate probability mesh.
E is the accumulated cost.
i represents time, j represents heart rate values in neighborhood, +/-4 bpm/second.

In one embodiment, cost representing fetal heart probability mesh values at each point of the estimated fetal heart rate over the particular time interval; and cost representing the overall tortuosity of the estimated fetal heart rate over the particular time interval is performed, by the at least one computer processor, using an exhaustive search.

In one embodiment, the present invention provides a computer implemented method that includes:
a) receiving raw Electrocardiogram (ECG) signals data from the at least one pair of ECG sensors; wherein the at least one pair of ECG sensors is positioned in on an abdomen of a pregnant human subject; wherein the raw ECG signals data comprise data representative of a N number of raw ECG signals (raw N-ECG signals data) which are being acquired in real-time from the at least one pair of ECG sensors; digital signal filtering the raw ECG signals data to form filtered N-ECG signals data having filtered N-ECG signals; detecting maternal heart peaks in each of the filtered N-ECG signal in the filtered N-ECG signals data; subtracting, from each of the filtered N-ECG signal of the filtered N-ECG signals data, the maternal ECG signal, by utilizing at least one non-linear subtraction procedure to obtain corrected ECG signals data which comprise data representative of a N number of corrected ECG signals (corrected N-ECG signals data), wherein the at least one non-linear subtraction procedure comprises: iteratively performing: i) dividing each filtered N-ECG signal of N-ECG signals of the filtered N-ECG signals data into a second plurality of ECG signal segments,) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) modifying each of the plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being; 2) setting a set of tentative values for a local template for each filtered N-ECG signal segment; and 3) utilizing at least one optimization scheme to determine an adaptive template for each filtered N-ECG signal segment based on the local template being matched to the global template within a pre-determined similarity value; and iii) eliminating the modified segments from each of the filtered N-ECG signals, by subtracting the adaptive template from the filtered N-ECG signal thereby generating each corrected ECG signal; extracting raw fetal ECG signals data from the filtered N-ECG signals data based on the corrected ECG signals data, wherein the raw fetal ECG signals data comprises a N number of fetal ECG signals (raw N-ECG fetal signals data); processing the raw N-ECG fetal signals data to improve a signal-to-noise ratio of the N-ECG fetal signals to form filtered N-ECG fetal signals data; detecting fetal heart peaks in the filtered N-ECG fetal signals data; calculating, based on detected fetal heart peaks, at least one of: i) fetal heart rate, ii) fetal heart curve, iii) beat-2-beat fetal heart rate, or iv) fetal heart rate variability; and outputting a result of the calculating operation;

b) receiving, by at least one computer processor executing specific programmable instructions configured for the method, a plurality of Phonocardiogram (PCG) signals data inputs from a plurality of acoustic sensors; digital signal filtering, by the at least one computer processor, utilizing a plurality of bandpass filters, the plurality of PCG signals data inputs to form a plurality of filtered PCG outputs, wherein the plurality of bandpass filters comprises a L number of bandpass filters, wherein each bandpass filter outputs a K number of filtered PCG outputs; wavelet denoising, by the at least one computer processor, a first subset of filtered PCG outputs of the plurality of filtered PCG outputs to form a M number of denoised filtered PCG outputs, wherein M is equal to L multiply by K; transforming, by the at least one computer processor, utilizing an Independent-Component-Analysis (ICA), a second subset of filtered PCG outputs of the plurality of filtered PCG outputs to form the M number of filtered ICA transforms; transforming, by the at least one computer processor, utilizing the Independent-Component-Analysis (ICA), a first portion of the second subset of denoised filtered PCG outputs to form the M number of denoised filtered ICA transforms; compiling, by the at least one computer processor, a S number of a plurality of detection heartbeat (DH) inputs, comprising: i) the M number of filtered PCG outputs, ii) the M number of the denoised filtered PCG outputs, iii) the M number of the filtered ICA transforms, and iv) the M number of the denoised filtered ICA transforms; detecting, by the at least one computer processor, beat locations of beats in each of DH inputs; calculating, by the at least one computer processor, a confidence score that describes a probability that the beats in each DH input of the plurality of DH inputs represent actual heartbeats and not a noise; dividing, by the at least one computer processor, the plurality of DH inputs into at least two groups: i) a first group of DH inputs containing fetal heartbeats, ii) a second group of DH inputs containing maternal heartbeats; selecting, by the at least one computer processor, from the first group of DH inputs, at least one particular fetal DH input that contains the fetal heartbeat based on a first confidence score of the at least one particular fetal DH input; and selecting, by the at least one computer processor, from the second group of DH inputs, at least one particular maternal DH input that contains the maternal heartbeat, based on a second confidence score of the at least one particular maternal DH input;

c) performing the following operations on the results of step a and b:
  i. receiving a calculated fetal heart rate for a plurality of time points over a particular time interval from filtered N-ECG fetal signals data and a calculated fetal heart rate for a plurality of time points over a particular time interval from filtered PCG outputs;
  ii. determining the score of the calculated fetal heart rate for the plurality of time points over the particular time interval for the filtered N-ECG fetal signals;
  iii. determining the score of the calculated fetal heart rate for the plurality of time points over the particular time interval for the filtered PCG outputs;
  iv. based on the calculated fetal heart rate and score for a plurality of time points over a particular time interval from filtered N-ECG fetal signals data, and the calculated fetal heart rate and score for a plurality of time points over a particular time interval from filtered PCG outputs, determining a consolidated fetal heart rate and score for the plurality of time points over the particular time interval, wherein the consolidated fetal heart rate and score for an individual time point within the plurality of time points is determined as one of the four options selected from the group consisting of:
    1. the weighted average of the calculated heart rate from the filtered N-ECG fetal signals data and the filtered PCG outputs for the individual time point, if the calculated heart rate from the filtered N-ECG fetal signals data and the filtered PCG outputs for the individual time point differs by 10 beats per minute or less, and if the scores of the calculated fetal heart rate for the individual time point for both the filtered N-ECG fetal signals data and the filtered PCG outputs are valid;

2. the calculated heart rate having the lower score, if the calculated heart rate from the filtered N-ECG fetal signals data and the filtered PCG outputs for the individual time point differs by more than 10 beats per minute, and if the scores of the calculated fetal heart rate for the individual time point for both the filtered N-ECG fetal signals data and the filtered PCG outputs are valid;

3. the calculated heart rate that has the valid score; and 4. no consolidated fetal heart rate and score, if neither the calculated heart rate from the filtered N-ECG fetal signals data or the filtered PCG outputs has a valid score;

v. based on the consolidated heart rate and scores for the plurality of time points over the particular time interval, generating, by the at least one computer processor, a fetal heart rate probability mesh;

vi. based on the fetal heart rate probability mesh, generating, by the at least one computer processor, an estimated fetal heart rate over the particular time interval, wherein the estimated fetal heart rate over the particular time interval is calculated based on (1) cost representing fetal heart probability mesh values at each point of the estimated fetal heart rate over the particular time interval; and (2) cost representing the overall tortuosity of the estimated fetal heart rate over the particular time interval.

In one embodiment, the present invention provides a computer implemented method that includes:

a) receiving a calculated fetal heart rate for a plurality of time points over a particular time interval from filtered N-ECG fetal signals data and a calculated fetal heart rate for a plurality of time points over a particular time interval from filtered PCG outputs;

b) determining the score of the calculated fetal heart rate for the plurality of time points over the particular time interval for the filtered N-ECG fetal signals;

c) determining the score of the calculated fetal heart rate for the plurality of time points over the particular time interval for the filtered PCG outputs;

d) based on the calculated fetal heart rate and score for a plurality of time points over a particular time interval from filtered N-ECG fetal signals data, and the calculated fetal heart rate and score for a plurality of time points over a particular time interval from filtered PCG outputs, determining a consolidated fetal heart rate and score for the plurality of time points over the particular time interval, wherein the consolidated fetal heart rate and score for an individual time point within the plurality of time points is determined as one of the four options selected from the group consisting of:

1. the weighted average of the calculated heart rate from the filtered N-ECG fetal signals data and the filtered PCG outputs for the individual time point, if the calculated heart rate from the filtered N-ECG fetal signals data and the filtered PCG outputs for the individual time point differs by 10 beats per minute or less, and if the scores of the calculated fetal heart rate for the individual time point for both the filtered N-ECG fetal signals data and the filtered PCG outputs are valid;

2. the calculated heart rate having the lower score, if the calculated heart rate from the filtered N-ECG fetal signals data and the filtered PCG outputs for the individual time point differs by more than 10 beats per minute, and if the scores of the calculated fetal heart rate for the individual time point for both the filtered N-ECG fetal signals data and the filtered PCG outputs are valid;

3. the calculated heart rate that has the valid score; and 4. no consolidated fetal heart rate and score, if neither the calculated heart rate from the filtered N-ECG fetal signals data or the filtered PCG outputs has a valid score;

e) based on the consolidated heart rate and scores for the plurality of time points over the particular time interval, generating, by the at least one computer processor, a fetal heart rate probability mesh;

f) based on the fetal heart rate probability mesh, generating, by the at least one computer processor, an estimated fetal heart rate over the particular time interval, wherein the estimated fetal heart rate over the particular time interval is calculated based on (1) cost representing fetal heart probability mesh values at each point of the estimated fetal heart rate over the particular time interval; and (2) cost representing the overall tortuosity of the estimated fetal heart rate over the particular time interval.

In one embodiment, cost representing fetal heart probability mesh values at each point of the estimated fetal heart rate over the particular time interval; and cost representing the overall tortuosity of the estimated fetal heart rate over the particular time interval is performed, by the at least one computer processor, using dynamic programming, where each value of the accumulated cost mesh is calculated as a sum of the fetal heart rate probability mesh value at that point and of the minimal path in its neighborhood in the previous step, based on:

$$E(i,j)=e(i,j)+\min(E(i-1,j-k)); k=-4:4$$

where:
e is the value of the fetal heart rate probability mesh.
E is the accumulated cost.
i represents time, j represents heart rate values in neighborhood, +/−4 bpm/second.

In one embodiment, cost representing fetal heart probability mesh values at each point of the estimated fetal heart rate over the particular time interval; and cost representing the overall tortuosity of the estimated fetal heart rate over the particular time interval is performed, by the at least one computer processor, using an exhaustive search.

BRIEF DESCRIPTION OF THE DRAWINGS

FIG. 10 shows a micrograph of electrically conductive fabric suitable as a cutaneous contact according to some embodiments of the present invention.

FIG. 14 shows a micrograph of electrically conductive fabric suitable as a cutaneous contact according to some embodiments of the present invention.

FIGS. 39A and 39B show flow charts of a signal denoising algorithm according to some embodiments of the present invention.

DETAILED DESCRIPTION

For clarity of disclosure, and not by way of limitation, the detailed description of the invention is divided into the following subsections that describe or illustrate certain features, embodiments or applications of the present invention.

As used herein the term "contact region" encompasses the contact area between the skin of a pregnant human subject and cutaneous contact i.e. the surface area through which current flow can pass between the skin of the pregnant human subject and the cutaneous contact.

The System According to Some Embodiments of the Present Invention:

This invention relates to apparatuses, systems and methods for continuous, non-invasive monitoring of a fetus and/or mother using from multiple electrocardiogram sensors that collect maternal and fetal electrical cardiac signals data and/or acoustic sensors that collect maternal and fetal acoustic cardiac signals data.

Figure 1:
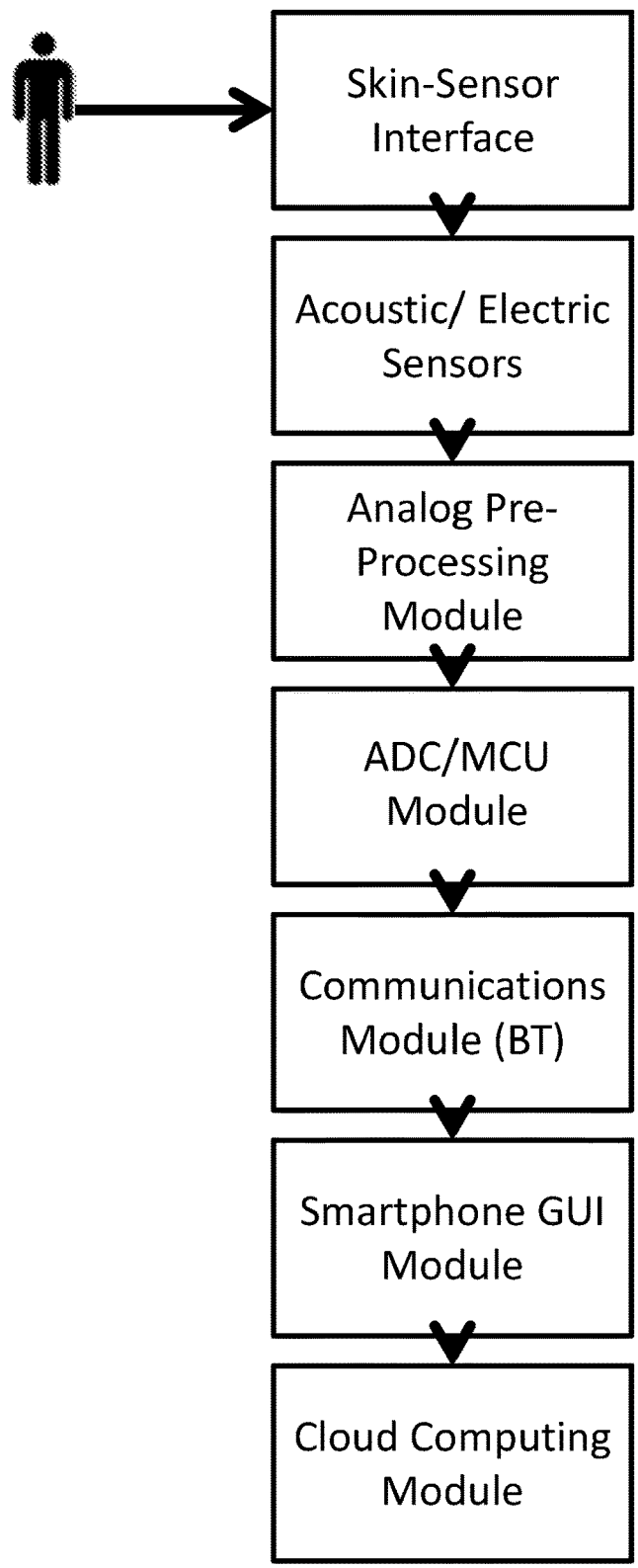
FIG. 1 shows a representation of a system suitable for use in fetal heart rate monitoring systems according to some embodiments of the present invention.

Referring to FIG. 1, in some embodiments, the system for recording, detecting and analyzing fetal cardiac electrical activity comprises a skin-electrode interface, at least one electrode, an analog pre-processing module, an analog to digital converter/microcontroller (ADC/MCU) module, a communications module, a smartphone module, and a cloud computing module.

In some embodiments, the analog pre-processing module performs at least one function selected from the group consisting of: amplification of the recorded signals, and filtering the recorded signals.

In some embodiments, the ADC/MCU module performs at least one task selected from the group consisting of: converting analog signals to digital signals, converting the recorded signals to digital signals, compressing the data, digital filtering, and transferring the recorded electrocardiogram signals data to the transmitter.

In some embodiments, the communications module transmits the recorded signals to a wireless receiver.

In some embodiments, the system for recording, detecting and analyzing fetal cardiac electrical activity data regardless of sensor position, fetal orientation, fetal movement, or gestational age is the system disclosed in International Patent Application Serial No. PCT/IL2015/050407.

Without intending to be limited by any particular theory, cardiac activity produces both acoustic and electrical signals. While the acoustic and electrical signals produced by cardiac activity may differ, they can be used together because they emanate from the same source (i.e. the feral and/or maternal heart).

However, the accuracy of fetal cardiac activity can be affected by several factors, such as, for example, fetal movement, the position of the fetal heart with respect to the at least one ECG electrode and/or the at least one acoustic sensor, maternal muscular activity, maternal cardiac activity, maternal anatomy, placental position, and the like.

Without intending to be limited to any particular theory, the background signals can be, for example, scattered signals from the placenta, fetal and/or maternal gastric sounds, fetal and/or maternal skeletal muscle activity, endometrial muscle activity, and the like.

For example, without intending to be limited to any particular theory, in some embodiments, the at least one ECG sensor and the at least one acoustic sensor are in fixed positions. The fetus moves freely within the womb of the pregnant human subject, and is rarely in a fixed position with respect to the sensors. This, together with the small size of the fetal heart, can (i) create artifacts in the signals data that is recorded, and (ii) require sensitive sensors and signal processing to detect fetal signals from a constantly varying background signals.

Without intending to be limited to any particular theory, electrical signals, such as fetal and maternal ECG signals and acoustic signals, such as fetal and maternal cardiac activity propagate differently. For instance, acoustic signals propagate well in fluid environments, such as, for example, the amniotic fluid, with minimal scattering. As another example, acoustic signals frequently have a lower signal to noise ratio, compared to ECG signals, possibly due to a lesser contribution of noise interference in ECG signals.

Thus, depending on the position of the fetus, the signal to noise ratio of the ECG signals and/or the acoustic signals may vary to a greater or lesser extent. For example, at one individual time point in a particular time frame, the acoustic signal may be absent, whilst the ECG signal is present. Thus, in some embodiments, the system of the present invention is capable of estimating fetal heart rate from either both fetal ECG signals data and fetal acoustic cardiac signals data, or just fetal ECG signals data, or just fetal acoustic cardiac signals data.

In the embodiments where the system of the present invention estimates fetal heart rate from both fetal ECG signals data and fetal acoustic cardiac signals data, the relative contribution of either the fetal ECG signals data or the fetal acoustic cardiac signals data may be equal, or unequal.

In some embodiments, the system of the present invention is able to continuously monitor fetal and maternal cardiac activity.

In some embodiments, the system of the present invention is used in a hospital setting. Alternatively, in some embodiments, the system of the present invention is used in a non-hospital setting.

In some embodiments, the system of the present invention, ECG signals data and or acoustic cardiac activity signals data is collected and analyzed from a plurality of systems, to establish a database.

In some embodiments, the database is utilized in "big data analysis", wherein the signals data collected from the system of the present invention by the pregnant human subject is compared to signals data obtained from pregnant human subjects having particular demographic and/or geographic or other statistical properties. Without intending to be limited to any particular theory, the comparison can allow a medical practitioner to advise the pregnant human subject to adjust diet, activity, medications, for example.

In some embodiments, the database is used by a healthcare professional and/or the pregnant human subject to monitor fetal and/or maternal cardiac activity and well being. Alternatively, the database can be used by the healthcare professional and/or the pregnant human subject to detect potentially harmful conditions, complications, or diseases during pregnancy. In some embodiments, a system according to the present invention is capable of detecting potentially harmful conditions, complications, or diseases earlier than would be possible during routine check-ups during standard of care ante-natal practice.

In some embodiments, the system is used by the pregnant human subject to reduce pregnancy associated factors, such as, for example, stress and risks related to nutrition, physical activity or lack thereof, sleep and other life-style factors that may affect the pregnancy.

In some embodiments, the pregnant human subject has been diagnosed as a high-risk pregnancy, and the system of the present invention is used in conjunction with a therapeutic treatment to treat or manage the high risk pregnancy.

In some embodiments, the pregnant human subject has at least one disease or disorder selected from the group consisting of heart disease, hypotension, hypertension, low body weight, obesity, preeclampsia, gestational diabetes, thrombolytic complications and placental lesions, and the system of the present invention is used in conjunction with a therapeutic treatment to treat or manage the at least one disease or disorder.

In some embodiments, the pregnant human subject has factors that are associated with a high risk pregnancy, and the system of the present invention is used in conjunction with a therapeutic treatment to treat or manage the high risk pregnancy.

In some embodiments, the garment according to some embodiments is worn by the pregnant human subject, wherein the garment is configured to continuously monitor fetal and maternal cardiac activity. In some embodiments, the fetal and maternal cardiac activity signals data is transmitted to a remote system, where the fetal and maternal cardiac activity signals data is processed to output fetal and maternal heart rate.

In some embodiments, the system of the present invention is capable of receiving and processing additional data, such as, for example, maternal physical activity, fetal kicks, maternal dietary intake, maternal health information, mood, and the like. In some embodiments, the additional data is used, along with the fetal and maternal cardiac activity signals data to detect potentially harmful conditions, complications, or diseases during pregnancy.

In some embodiments, the additional data is used, along with the fetal and maternal cardiac activity signals data to reduce pregnancy associated factors, such as, for example, stress and risks related to nutrition, physical activity or lack thereof, sleep and other life-style factors that may affect the pregnancy.

Examples of fetal parameters according to some embodiments of the present invention is capable of monitoring include: cardiac activity, heart rate, cardiac vibro/acoustic sounds, pulse rate, heart rate variability, bradycardia event, tachycardia event, desaturation, fetal movement, fetal position/orientation, fetal sounds, fetal kicks, fetal brain activity, fetal temperature, glucose, sleeping state, blood flow, blood pressure, or activity level.

Examples of maternal parameters according to some embodiments of the present invention is capable of monitoring include: cardiac activity, ejection fraction, heart rate, heart sounds, breathing depth and duration, pulse rate, heart rate variability, bradycardia event, tachycardia event, desaturation, brain activity, temperature, glucose, inflammation level, uterus activity, sleeping stages, blood pressure, physical activity level, posture, or body position.

In some embodiments, the system of the present invention is worn by the pregnant human subject for an extended period of time. The extended period of time can be 24 hours or more. Alternatively, in some embodiments, the system of the present invention is worn by the pregnant human subject for 24 hours or less. Alternatively, in some embodiments, the system of the present invention is worn by the pregnant human subject for 24 hours. Alternatively, in some embodiments, the system of the present invention is worn by the pregnant human subject for 12 hours. Alternatively, in some embodiments, the system of the present invention is worn by the pregnant human subject for 11 hours. Alternatively, in some embodiments, the system of the present invention is worn by the pregnant human subject for 10 hours. Alternatively, in some embodiments, the system of the present invention is worn by the pregnant human subject for 9 hours. Alternatively, in some embodiments, the system of the present invention is worn by the pregnant human subject for 8 hours. Alternatively, in some embodiments, the system of the present invention is worn by the pregnant human subject for 7 hours. Alternatively, in some embodiments, the system of the present invention is worn by the pregnant human subject for 6 hours. Alternatively, in some embodiments, the system of the present invention is worn by the pregnant human subject for 5 hours. Alternatively, in some embodiments, the system of the present invention is worn by the pregnant human subject for 4 hours. Alternatively, in some embodiments, the system of the present invention is worn by the pregnant human subject for 3 hours. Alternatively, in some embodiments, the system of the present invention is worn by the pregnant human subject for 2 hours. Alternatively, in some embodiments, the system of the present invention is worn by the pregnant human subject for 1 hour.

In one embodiment, the present invention provides a system for monitoring maternal and fetal cardiac activity that includes:
a) at least one electrocardiogram sensor configured to contact the skin of the abdomen of a pregnant human subject and detect fetal and maternal cardiac electrical activity;
b) at least one acoustic sensor configured to contact the skin of the abdomen of a pregnant human subject and detect fetal and maternal cardiac electrical activity;
c) a garment configured to position and contact the at least one electrocardiogram sensor and the at least one acoustic sensor on the abdomen of the pregnant human subject;
d) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving raw Electrocardiogram (ECG) signals data from the at least one pair of ECG sensors; wherein the at least one pair of ECG sensors is positioned in on an abdomen of a pregnant human subject; wherein the raw ECG signals data comprise data representative of a N number of raw ECG signals (raw N-ECG signals data) which are being acquired in real-time from the at least one pair of ECG sensors; digital signal filtering the raw ECG signals data to form filtered N-ECG signals data having filtered N-ECG signals; detecting maternal heart peaks in each of the filtered N-ECG signal in the filtered N-ECG signals data; subtracting, from each of the filtered N-ECG signal of the filtered N-ECG signals data, the maternal ECG signal, by utilizing at least one non-linear subtraction procedure to obtain corrected ECG signals data which comprise data representative of a N number of corrected ECG signals (corrected N-ECG signals data), wherein the at least one non-linear subtraction procedure comprises: iteratively performing: i) dividing each filtered N-ECG signal of N-ECG signals of the filtered N-ECG signals data into a second plurality of ECG signal segments,) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) modifying each of the plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being; 2) setting a set of tentative values for a local template for each filtered N-ECG signal segment; and 3) utilizing at least one optimization scheme to determine an adaptive template for each filtered N-ECG signal segment based on the local template being matched to the global template within a pre-determined similarity value; and iii) eliminating the modified segments from each of the filtered N-ECG signals, by subtracting the adaptive template from the filtered N-ECG signal thereby generating each corrected ECG signal; extracting raw fetal ECG signals data from the filtered N-ECG signals data based on the corrected ECG signals data, wherein the raw fetal ECG signals data comprises a N number of fetal ECG signals (raw N-ECG fetal signals data); processing the raw N-ECG fetal signals data to improve a signal-to-noise ratio of the N-ECG fetal signals to form filtered N-ECG fetal signals data; detecting fetal heart peaks in the filtered N-ECG fetal signals data; calculating, based on detected fetal heart peaks, at least one of: i) fetal heart rate, ii) fetal heart curve, iii) beat-2-beat fetal heart rate, or iv) fetal heart rate variability; and outputting a result of the calculating operation;

e) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving, by at least one computer processor executing specific programmable instructions configured for the method, a plurality of Phonocardiogram (PCG) signals data inputs from a plurality of acoustic sensors; digital signal filtering, by the at least one computer processor, utilizing a plurality of bandpass filters, the plurality of PCG signals data inputs to form a plurality of filtered PCG outputs, wherein the plurality of bandpass filters comprises a L number of bandpass filters, wherein each bandpass filter outputs a K number of filtered PCG outputs; wavelet denoising, by the at least one computer processor, a first subset of filtered PCG outputs of the plurality of filtered PCG outputs to form a M number of denoised filtered PCG outputs, wherein M is equal to L multiply by K; transforming, by the at least one computer processor, utilizing an Independent-Component-Analysis (ICA), a second subset of filtered PCG outputs of the plurality of filtered PCG outputs to form the M number of filtered ICA transforms; transforming, by the at least one computer processor, utilizing the Independent-Component-Analysis (ICA), a first portion of the second subset of denoised filtered PCG outputs to form the M number of denoised filtered ICA transforms; compiling, by the at least one computer processor, a S number of a plurality of detection heartbeat (DH) inputs, comprising: i) the M number of filtered PCG outputs, ii) the M number of the denoised filtered PCG outputs, iii) the M number of the filtered ICA transforms, and iv) the M number of the denoised filtered ICA transforms; detecting, by the at least one computer processor, beat locations of beats in each of DH inputs; calculating, by the at least one computer processor, a confidence score that describes a probability that the beats in each DH input of the plurality of DH inputs represent actual heartbeats and not a noise; dividing, by the at least one computer processor, the plurality of DH inputs into at least two groups: i) a first group of DH inputs containing fetal heartbeats, ii) a second group of DH inputs containing maternal heartbeats; selecting, by the at least one computer processor, from the first group of DH inputs, at least one particular fetal DH input that contains the fetal heartbeat based on a first confidence score of the at least one particular fetal DH input; and selecting, by the at least one computer processor, from the second group of DH inputs, at least one particular maternal DH input that contains the maternal heartbeat, based on a second confidence score of the at least one particular maternal DH input;

f) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations:
i. receiving a calculated fetal heart rate for a plurality of time points over a particular time interval from filtered N-ECG fetal signals data and a calculated fetal heart rate for a plurality of time points over a particular time interval from filtered PCG outputs;
ii. determining the score of the calculated fetal heart rate for the plurality of time points over the particular time interval for the filtered N-ECG fetal signals;
iii. determining the score of the calculated fetal heart rate for the plurality of time points over the particular time interval for the filtered PCG outputs;
iv. based on the calculated fetal heart rate and score for a plurality of time points over a particular time interval from filtered N-ECG fetal signals data, and the calculated fetal heart rate and score for a plurality of time points over a particular time interval from filtered PCG outputs, determining a consolidated fetal heart rate and score for the plurality of time points over the particular time interval,
wherein the consolidated fetal heart rate and score for an individual time point within the plurality of time points is determined as one of the four options selected from the group consisting of:
1. the weighted average of the calculated heart rate from the filtered N-ECG fetal signals data and the filtered PCG outputs for the individual time point, if the calculated heart rate from the filtered N-ECG fetal signals data and the filtered PCG outputs for the individual time point differs by 10 beats per minute or less, and if the scores of the calculated fetal heart rate for the individual time point for both the filtered N-ECG fetal signals data and the filtered PCG outputs are valid;
2. the calculated heart rate having the lower score, if the calculated heart rate from the filtered N-ECG fetal signals data and the filtered PCG outputs for the individual time point differs by more than 10 beats per minute, and if the scores of the calculated fetal heart rate for the individual time point for both the filtered N-ECG fetal signals data and the filtered PCG outputs are valid;
3. the calculated heart rate that has the valid score; and
4. no consolidated fetal heart rate and score, if neither the calculated heart rate from the filtered N-ECG fetal signals data or the filtered PCG outputs has a valid score;

v. based on the consolidated heart rate and scores for the plurality of time points over the particular time interval, generating, by the at least one computer processor, a fetal heart rate probability mesh;

vi. based on the fetal heart rate probability mesh, generating, by the at least one computer processor, an estimated fetal heart rate over the particular time interval, wherein the estimated fetal heart rate over the particular time interval is calculated based on (1) cost representing fetal heart probability mesh values at each point of the estimated fetal heart rate over the particular time interval; and (2) cost representing the overall tortuosity of the estimated fetal heart rate over the particular time interval.

The Garment According to Some Embodiments of the Present Invention

In one embodiment, the present invention provides a garment that includes:

a) at least one electrocardiogram sensor configured to contact the skin of the abdomen of a pregnant human subject and detect fetal and maternal cardiac electrical activity;

b) at least one acoustic sensor configured to contact the skin of the abdomen of a pregnant human subject and detect fetal and maternal cardiac electrical activity; and c) a garment configured to position and contact the at least one electrocardiogram sensor and the at least one acoustic sensor on the abdomen of the pregnant human subject.

In one embodiment, the garment is further configured to include:

a) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving raw Electrocardiogram (ECG) signals data from the at least one pair of ECG sensors; wherein the at least one pair of ECG sensors is positioned in on an abdomen of a pregnant human subject; wherein the raw ECG signals data comprise data representative of a N number of raw ECG signals (raw N-ECG signals data) which are being acquired in real-time from the at least one pair of ECG sensors; digital signal filtering the raw ECG signals data to form filtered N-ECG signals data having filtered N-ECG signals; detecting maternal heart peaks in each of the filtered N-ECG signal in the filtered N-ECG signals data; subtracting, from each of the filtered N-ECG signal of the filtered N-ECG signals data, the maternal ECG signal, by utilizing at least one non-linear subtraction procedure to obtain corrected ECG signals data which comprise data representative of a N number of corrected ECG signals (corrected N-ECG signals data), wherein the at least one non-linear subtraction procedure comprises: iteratively performing: i) dividing each filtered N-ECG signal of N-ECG signals of the filtered N-ECG signals data into a second plurality of ECG signal segments,) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) modifying each of the plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being; 2) setting a set of tentative values for a local template for each filtered N-ECG signal segment; and 3) utilizing at least one optimization scheme to determine an adaptive template for each filtered N-ECG signal segment based on the local template being matched to the global template within a pre-determined similarity value; and iii) eliminating the modified segments from each of the filtered N-ECG signals, by subtracting the adaptive template from the filtered N-ECG signal thereby generating each corrected ECG signal; extracting raw fetal ECG signals data from the filtered N-ECG signals data based on the corrected ECG signals data, wherein the raw fetal ECG signals data comprises a N number of fetal ECG signals (raw N-ECG fetal signals data); processing the raw N-ECG fetal signals data to improve a signal-to-noise ratio of the N-ECG fetal signals to form filtered N-ECG fetal signals data; detecting fetal heart peaks in the filtered N-ECG fetal signals data; calculating, based on detected fetal heart peaks, at least one of: i) fetal heart rate, ii) fetal heart curve, iii) beat-2-beat fetal heart rate, or iv) fetal heart rate variability; and outputting a result of the calculating operation;

b) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations: receiving, by at least one computer processor executing specific programmable instructions configured for the method, a plurality of Phonocardiogram (PCG) signals data inputs from a plurality of acoustic sensors; digital signal filtering, by the at least one computer processor, utilizing a plurality of bandpass filters, the plurality of PCG signals data inputs to form a plurality of filtered PCG outputs, wherein the plurality of bandpass filters comprises a L number of bandpass filters, wherein each bandpass filter outputs a K number of filtered PCG outputs; wavelet denoising, by the at least one computer processor, a first subset of filtered PCG outputs of the plurality of filtered PCG outputs to form a M number of denoised filtered PCG outputs, wherein M is equal to L multiply by K; transforming, by the at least one computer processor, utilizing an Independent-Component-Analysis (ICA), a second subset of filtered PCG outputs of the plurality of filtered PCG outputs to form the M number of filtered ICA transforms; transforming, by the at least one computer processor, utilizing the Independent-Component-Analysis (ICA), a first portion of the second subset of denoised filtered PCG outputs to form the M number of denoised filtered ICA transforms; compiling, by the at least one computer processor, a S number of a plurality of detection heartbeat (DH) inputs, comprising: i) the M number of filtered PCG outputs, ii) the M number of the denoised filtered PCG outputs, iii) the M number of the filtered ICA transforms, and iv) the M number of the denoised filtered ICA transforms; detecting, by the at least one computer processor, beat locations of beats in each of DH inputs; calculating, by the at least one computer processor, a confidence score that describes a probability that the beats in each DH input of the plurality of DH inputs represent actual heartbeats and not a noise; dividing, by the at least one computer processor, the plurality of DH inputs into at least two groups: i) a first group of DH inputs containing fetal heartbeats, ii) a second group of DH inputs containing maternal heartbeats; selecting, by the at least one computer processor, from the first group of DH inputs, at least one particular fetal DH input that contains the fetal heartbeat based on a first confidence score of the at least one particular fetal DH input; and selecting, by the at least one computer processor, from the second group of DH inputs, at least one particular maternal DH input that contains the maternal heartbeat, based on a second confidence score of the at least one particular maternal DH input;

c) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations:
  i. receiving a calculated fetal heart rate for a plurality of time points over a particular time interval from filtered N-ECG fetal signals data and a calculated fetal heart rate for a plurality of time points over a particular time interval from filtered PCG outputs;
  ii. determining the score of the calculated fetal heart rate for the plurality of time points over the particular time interval for the filtered N-ECG fetal signals;
  iii. determining the score of the calculated fetal heart rate for the plurality of time points over the particular time interval for the filtered PCG outputs;
  iv. based on the calculated fetal heart rate and score for a plurality of time points over a particular time interval from filtered N-ECG fetal signals data, and the calculated fetal heart rate and score for a plurality of time points over a particular time interval from filtered PCG outputs, determining a consolidated fetal heart rate and score for the plurality of time points over the particular time interval,
    wherein the consolidated fetal heart rate and score for an individual time point within the plurality of time points is determined as one of the four options selected from the group consisting of:
      1. the weighted average of the calculated heart rate from the filtered N-ECG fetal signals data and the filtered PCG outputs for the individual time point, if the calculated heart rate from the filtered N-ECG fetal signals data and the filtered PCG outputs for the individual time point differs by 10 beats per minute or less, and if the scores of the calculated fetal heart rate for the individual time point for both the filtered N-ECG fetal signals data and the filtered PCG outputs are valid;
      2. the calculated heart rate having the lower score, if the calculated heart rate from the filtered N-ECG fetal signals data and the filtered PCG outputs for the individual time point differs by more than 10 beats per minute, and if the scores of the calculated fetal heart rate for the individual time point for both the filtered N-ECG fetal signals data and the filtered PCG outputs are valid;
      3. the calculated heart rate that has the valid score; and
      4. no consolidated fetal heart rate and score, if neither the calculated heart rate from the filtered N-ECG fetal signals data or the filtered PCG outputs has a valid score;
  v. based on the consolidated heart rate and scores for the plurality of time points over the particular time interval, generating, by the at least one computer processor, a fetal heart rate probability mesh;
  vi. based on the fetal heart rate probability mesh, generating, by the at least one computer processor, an estimated fetal heart rate over the particular time interval,
    wherein the estimated fetal heart rate over the particular time interval is calculated based on (1) cost representing fetal heart probability mesh values at each point of the estimated fetal heart rate over the particular time interval; and (2) cost representing the overall tortuosity of the estimated fetal heart rate over the particular time interval.

In some embodiments, the system of the present invention can includes at least one additional maternal or fetal cardiac sensing modality. Such modality can also replace the said electric or acoustic cardiac sensing modality. This can be an active or passive sensing modality, selected from the group consisting of: ultrasound, Doppler, ultrasound/Doppler (which may be described as high frequency acoustic signals with sensors using Doppler technology), PAT (which stands for Peripheral Arterial Tone) optical sensor which observes maternal heart rate from skin color changes and FNIRS (which stands for functional near infra-red spectroscopy).

In some embodiments, the acoustic sensor can be a vibro-acoustic sensor which senses the acoustic signal of the closure of the valves and also senses the cardiac vibrations of the contractions of the heart muscle.

In some embodiments, the garment is configured to allow the system to be ambulatory and operable by the pregnant human subject in any setting, such as, for example, at home. For example, referring to FIG. 2-FIG. 4, the garment (1) is incorporated with at least one ECG sensor (3), at least one acoustic sensor (2) and a transmitter (4) for communicating the output of the one or more processors to a remote server via at least one of low emission Bluetooth (Bluetooth Low Energy) for communication of an output of the processor to a remote server.

In some embodiments, the garment is washable. In some embodiments, wiring necessary for the operation of the system is waterproof, and hidden.

In some embodiments, the garment is made from a non-irritating material.

Figure 2:
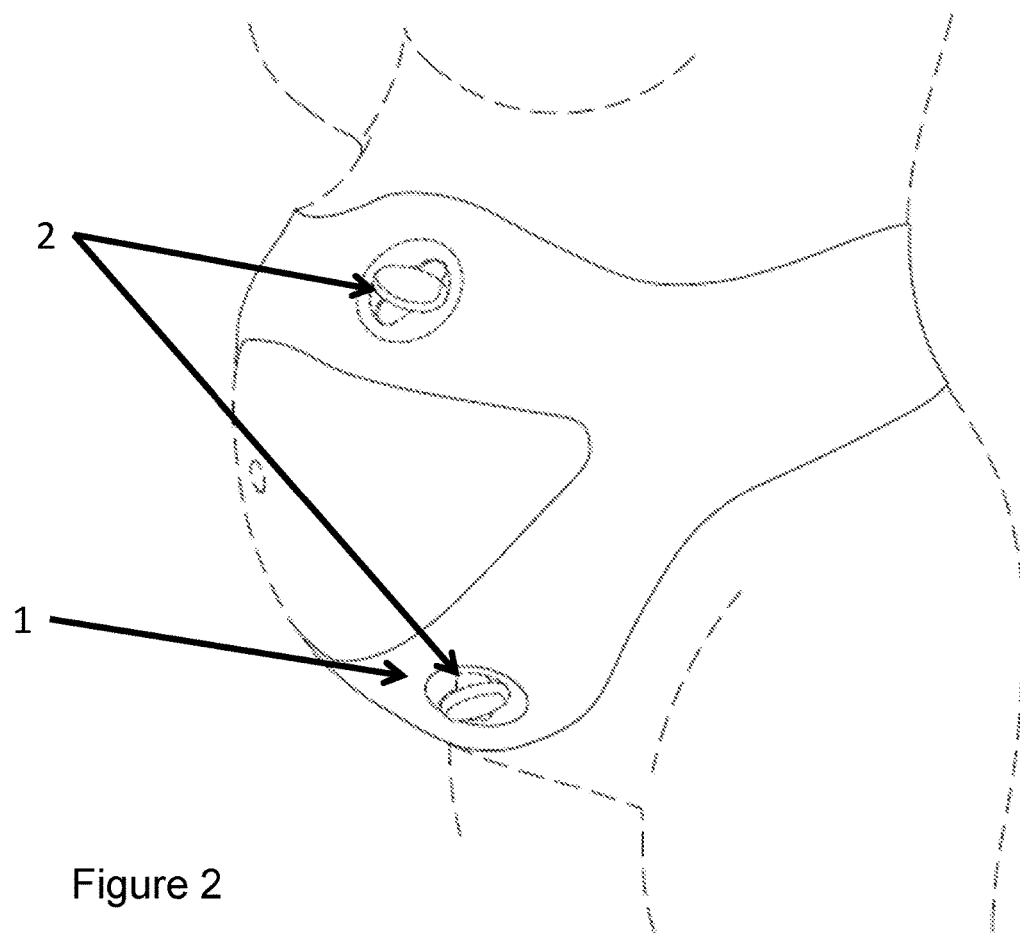
FIG. 2 shows a first view of a garment according to some embodiments of the present invention being worn by a pregnant human subject.
Figure 3:
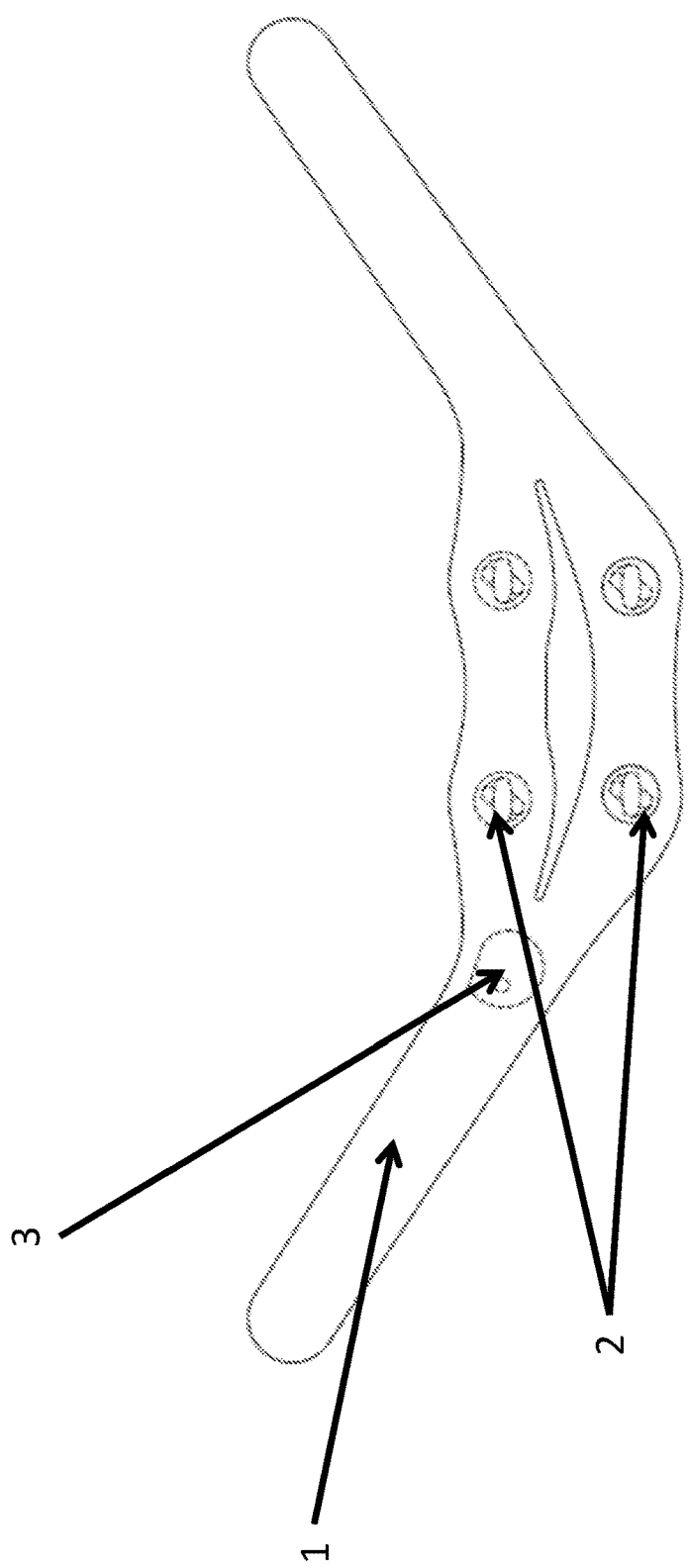
FIG. 3 shows a front view of a garment according to some embodiments of the present invention.
Figure 4:
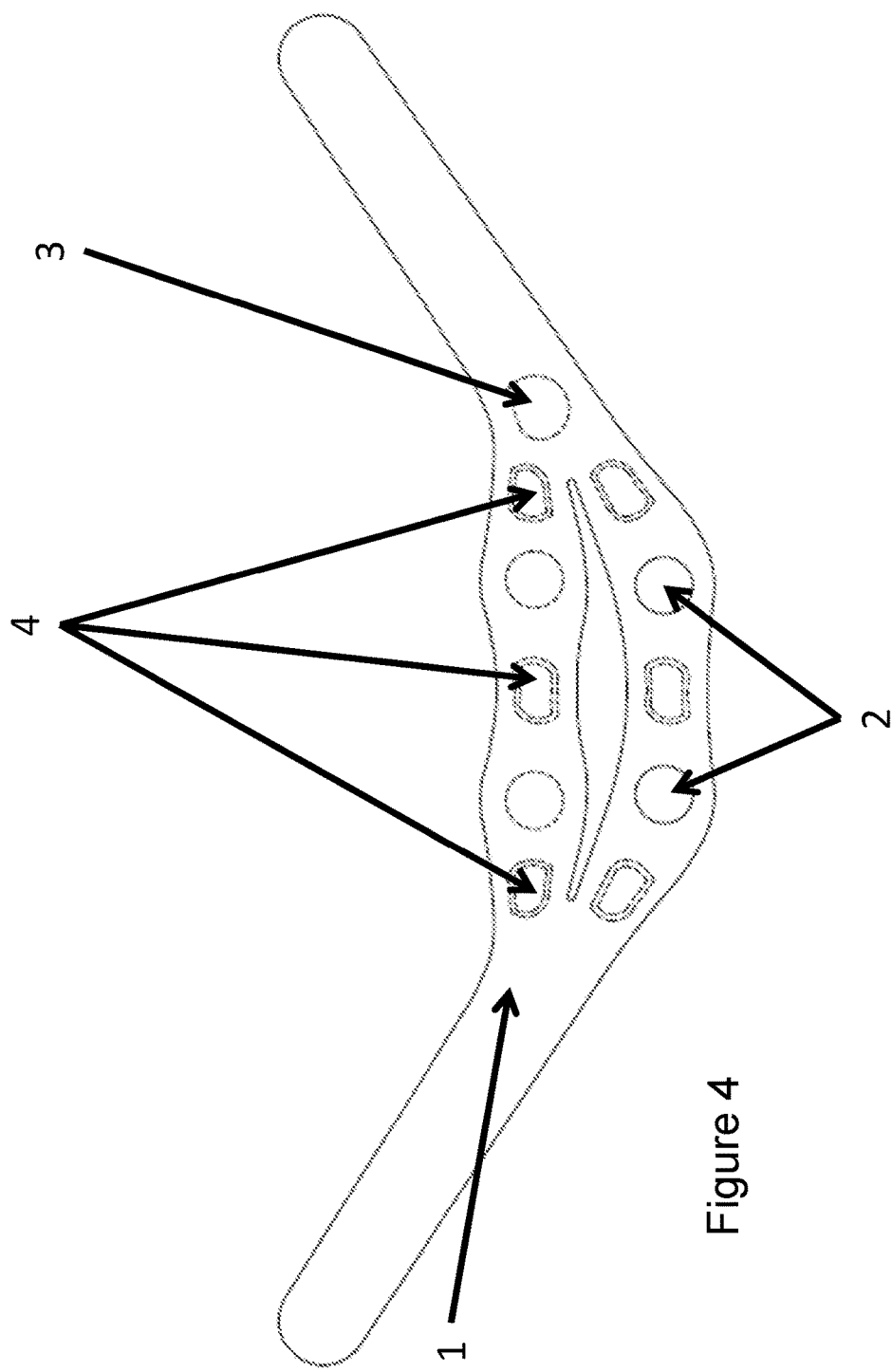
FIG. 4 shows a rear view of a garment according to some embodiments of the present invention.

In the embodiment shown in FIG. 2-FIG. 4, the at least one acoustic sensor is removable. In alternate embodiments, the at least one acoustic sensor is removable. In alternate embodiments, the transmitter is removable.

In some embodiments, the garment further includes audio speakers.

In some embodiments, the garment further includes a power supply.

In some embodiments, the garment comprises the belt disclosed in U.S. Pat. No. 8,396,229 B2.

In some embodiments, the garment is manufactured from the materials disclosed in U.S. Pat. No. 8,396,229 B2.

In some embodiments, the garment is manufactured according to the methods disclosed in U.S. Pat. No. 8,396,229 B2.

ECG Sensors According to Some Embodiments of the Present Invention

In some embodiments, the present invention provides an ECG sensor configured to detect fetal electrocardiogram signals, comprising:
a) a cutaneous contact for sensing fetal electrocardiogram signals from a pregnant human subject;
b) a connector in electrical contact with the cutaneous contact for connection to a lead wire; and
c) a substructure for attachment to a human pregnant subject wherein, the cutaneous contact is configured on the substructure to allow a surface of the cutaneous contact to be in electrical communication with the skin of the pregnant human subject.

Without intending to be limited to any particular theory, in some embodiments, the three-dimensional shape of the ECG sensor affects the performance. For example, a curved profile without sharp angles is likely to prevent abrupt changes in the electrical field generated by the cutaneous contact, or flow of current from the cutaneous contact to the lead wire.

Figure 5:
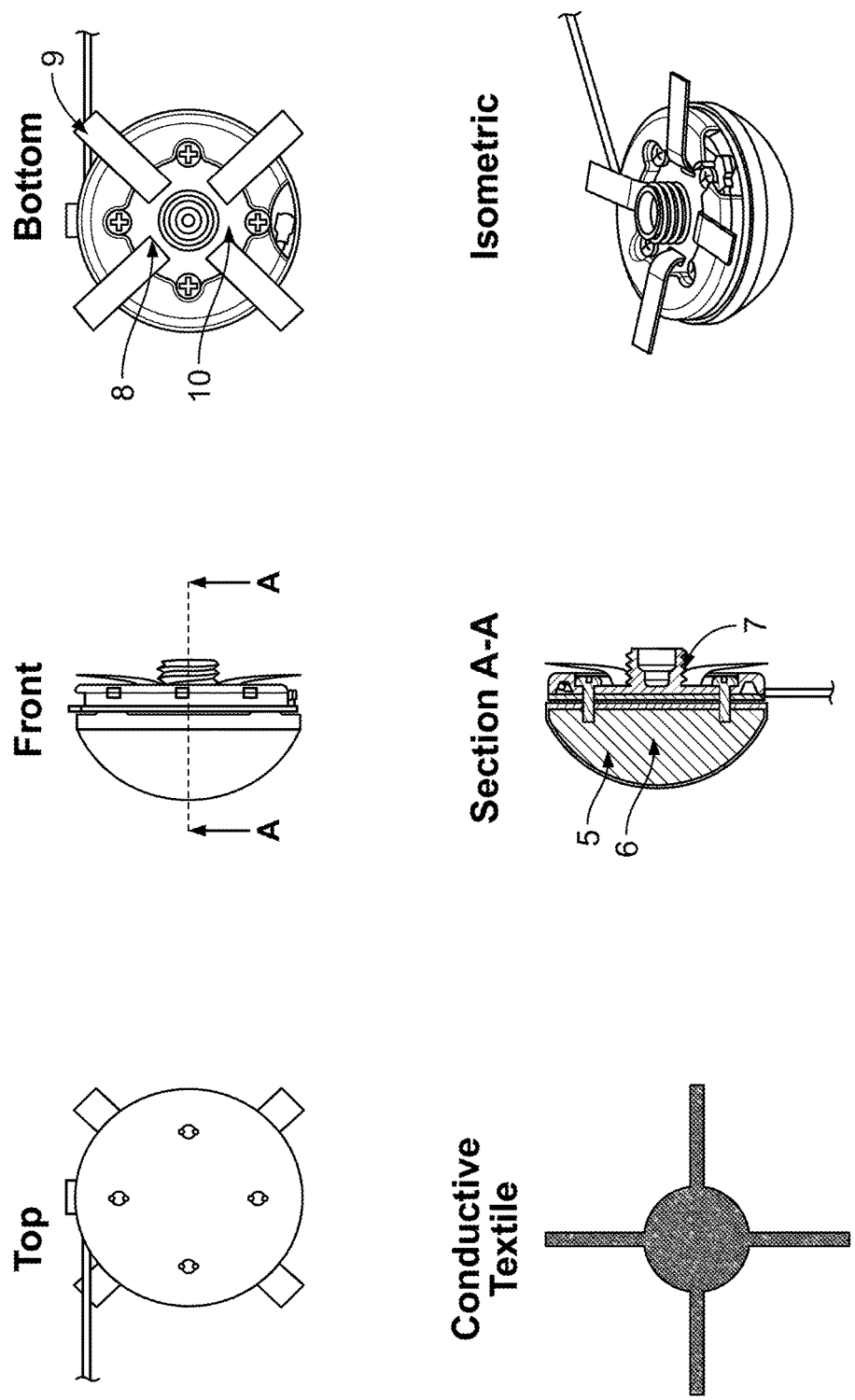
FIG. 5 shows an ECG sensor according to some embodiments of the present invention.

FIG. 5 shows a circular ECG sensor according to some embodiments of the present invention. In the embodiment shown in FIG. 5, the ECG sensor, as shown along the section A-A, comprises an electrically conductive fabric (5) attached over an elastomeric dome shaped circular structure (6), which is, in turn, attached to a circular foam backing. The foam backing is attached to a printed circuit board (8), which has one electrical connection (9) that outputs the sensed fetal electrocardiogram signals, and at least one electrical connection (10) that connects the electrically conductive fabric to the printed circuit board (8).

In some embodiments, the printed circuit board is configured to interface the cutaneous contact with the lead wire. Alternatively, in some embodiments, the printed circuit board is further configured to perform additional functions, such as, for example, signal filtering, or pre-amplification.

Figure 6:
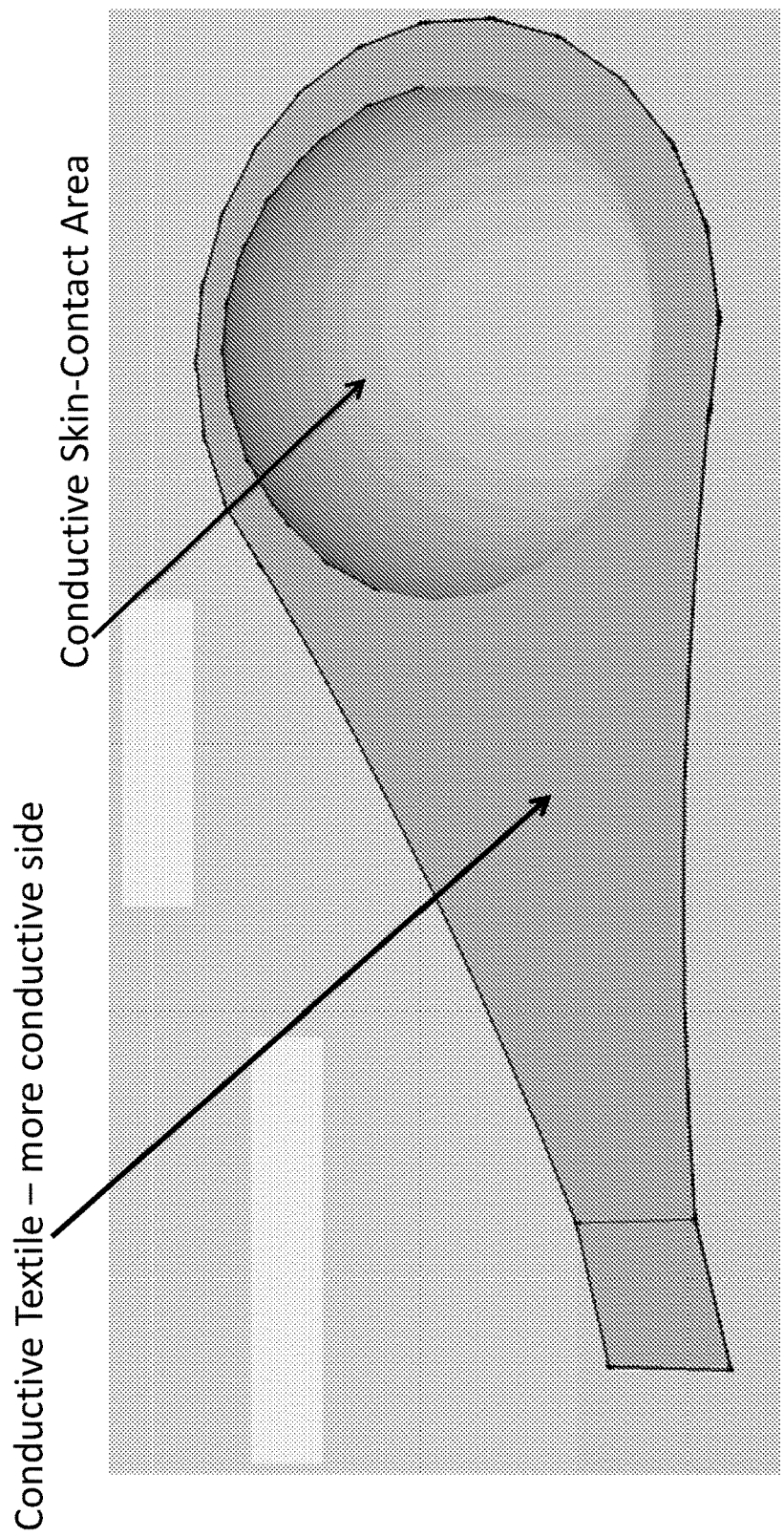
FIG. 6 shows an ECG sensor according to some embodiments of the present invention.

FIG. 6 shows an ECG sensor according to some embodiments of the present invention. In the embodiment shown, the ECG sensor consists of a teardrop-shaped electrically conductive fabric, with a flat portion that terminates at one end with a connection to a printed circuit board, and a dome-shaped structure that forms a skin contact at the opposite end. In the embodiment shown, only the dome-shaped structure would be exposed and touch the skin of the pregnant human subject.

Figure 7:
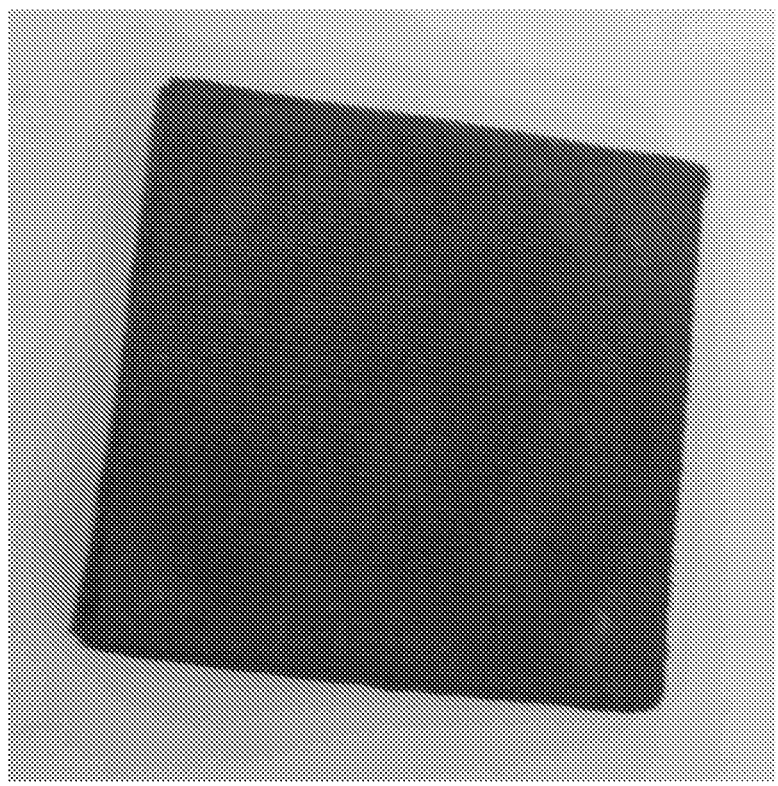
FIG. 7 shows an ECG sensor according to some embodiments of the present invention.
Figure 8:
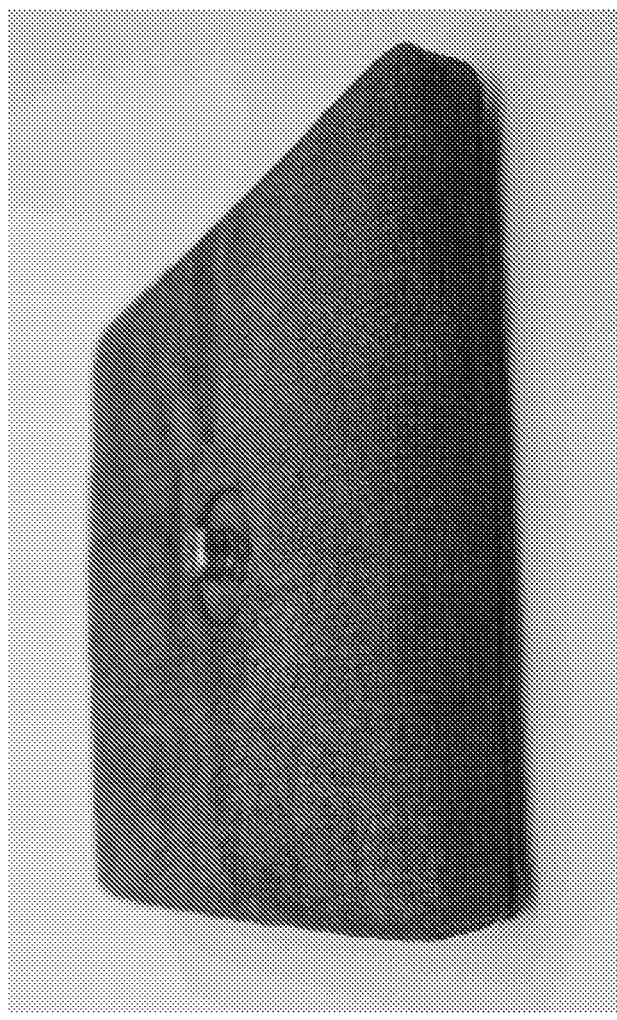
FIG. 8 shows an ECG sensor according to some embodiments of the present invention.

FIGS. 7 and 8 show alternate embodiments of ECG sensors according to the present invention comprising a planar cutaneous contact.

In the embodiment shown in FIG. 5, the elastomeric dome shaped circular structure is configured to maximize contact between the cutaneous contact and the skin of the pregnant human subject under a all possible attachment angles.

In the embodiment shown in FIG. 5, the elastomeric dome shaped circular structure is configured to generate a profile without sharp angles which are likely to affect performance of the ECG sensor.

In some embodiments, the elastomeric dome shaped circular structure has a diameter ranging from 20 to 50 mm. In some embodiments, the elastomeric dome shaped circular structure has a diameter of 20 mm. In some embodiments, the elastomeric dome shaped circular structure has a diameter of 25 mm. In some embodiments, the elastomeric dome shaped circular structure has a diameter of 30 mm. In some embodiments, the elastomeric dome shaped circular structure has a diameter of 35 mm. In some embodiments, the elastomeric dome shaped circular structure has a diameter of 40 mm. In some embodiments, the elastomeric dome shaped circular structure has a diameter of 45 mm. In some embodiments, the elastomeric dome shaped circular structure has a diameter of 50 mm.

In some embodiments, the elastomeric dome shaped circular structure has an un-deformed height (i.e. a height before pressure is applied) ranging from 5 to 15 mm. In some embodiments, the elastomeric dome shaped circular structure has an un-deformed height of 5 mm. In some embodiments, the elastomeric dome shaped circular structure has an un-deformed height of 10 mm. In some embodiments, the elastomeric dome shaped circular structure has an un-deformed height of 15 mm.

In some embodiments, the circular foam backing has a thickness ranging from 0.3 to 5 mm. In some embodiments, the circular foam backing has a thickness of 0.3 mm. In some embodiments, the circular foam backing has a thickness of 0.5 mm. In some embodiments, the circular foam backing has a thickness of 1 mm. In some embodiments, the circular foam backing has a thickness of 1.5 mm. In some embodiments, the circular foam backing has a thickness of 2 mm. In some embodiments, the circular foam backing has a thickness of 2.5 mm. In some embodiments, the circular foam backing has a thickness of 3 mm. In some embodiments, the circular foam backing has a thickness of 3.5 mm. In some embodiments, the circular foam backing has a thickness of 4 mm. In some embodiments, the circular foam backing has a thickness of 4.5 mm. In some embodiments, the circular foam backing has a thickness of 5 mm.

In the embodiment shown in FIG. 6, the elastomeric dome shaped circular structure is configured to generate a profile without sharp angles which are likely affect performance of the ECG sensor. In some embodiments, the elastomeric dome shaped circular structure has a diameter ranging from 15 to 38 mm. In some embodiments, the elastomeric dome shaped circular structure has a diameter of 15 mm. In some embodiments, the elastomeric dome shaped circular structure has a diameter of 20 mm. In some embodiments, the elastomeric dome shaped circular structure has a diameter of 25 mm. In some embodiments, the elastomeric dome shaped circular structure has a diameter of 30 mm. In some embodiments, the elastomeric dome shaped circular structure has a diameter of 35 mm. In some embodiments, the elastomeric dome shaped circular structure has a diameter of 38 mm.

In some embodiments, the elastomeric dome shaped circular structure has an un-deformed height (i.e. a height before pressure is applied) ranging from 5 to 15 mm. In some embodiments, the elastomeric dome shaped circular structure has an un-deformed height of 5 mm. In some embodiments, the elastomeric dome shaped circular structure has an un-deformed height of 10 mm. In some embodiments, the elastomeric dome shaped circular structure has an un-deformed height of 15 mm.

Without intending to be limited to any particular theory, the skin-ECG sensor impedance varies with the pressure at which the ECG sensor contacts the skin of the pregnant human subject. In some embodiments, the skin-ECG sensor impedance decreases as the pressure at which the ECG sensor contacts the skin of the pregnant human subject increases.

In some embodiments, the elastomeric dome is configured to deform when placed on the abdomen of the pregnant human subject and pressure is applied to the ECG sensor. In some embodiments, the elastomeric dome is configured to deform when placed on the abdomen of the pregnant human subject and pressure applied to create a skin-ECG sensor impedance suitable for sensing fetal electrocardiogram signals from a pregnant human subject.

In some embodiments, the deformation of the elastomeric dome increases the surface area of the cutaneous contact that contacts the skin of the pregnant human subject. In some embodiments, 100% of the surface area of the cutaneous contact contacts the skin of the pregnant human subject. In an alternate embodiment, 90% of the surface area of the cutaneous contact contacts the skin of the pregnant human subject. In an alternate embodiment, 80% of the surface area of the cutaneous contact contacts the skin of the pregnant human subject. In an alternate embodiment, 70% of the surface area of the cutaneous contact contacts the skin of the pregnant human subject. In an alternate embodiment, 60% of the surface area of the cutaneous contact contacts the skin of the pregnant human subject. In an alternate embodiment, 50% of the surface area of the cutaneous contact contacts the skin of the pregnant human subject. In an alternate embodiment, 40% of the surface area of the cutaneous contact contacts the skin of the pregnant human subject. In an alternate embodiment, 30% of the surface area of the cutaneous contact contacts the skin of the pregnant human subject. In an alternate embodiment, 20% of the surface area of the cutaneous contact contacts the skin of the pregnant human subject. In an alternate embodiment, 10% of the surface area of the cutaneous contact contacts the skin of the pregnant human subject. In an alternate embodiment, 75% of the surface area of the cutaneous contact contacts the skin of the pregnant human subject.

In some embodiments, the pressure applied is equivalent to a mass ranging between 0.2 kg to 5 kg. In some embodiments, the pressure applied is equivalent to a mass of 0.2 kg. In some embodiments, the pressure applied is equivalent to a mass of 0.2 kg. In some embodiments, the pressure applied is equivalent to a mass of 0.3 kg. In some embodiments, the pressure applied is equivalent to a mass of 0.4 kg. In some embodiments, the pressure applied is equivalent to a mass of 0.5 kg. In some embodiments, the pressure applied is equivalent to a mass of 0.6 kg. In some embodiments, the pressure applied is equivalent to a mass of 0.7 kg. In some embodiments, the pressure applied is equivalent to a mass of 0.8 kg. In some embodiments, the pressure applied is equivalent to a mass of 0.9 kg. In some embodiments, the pressure applied is equivalent to a mass of 1 kg. In some embodiments, the pressure applied is equivalent to a mass of 1.5 kg. In some embodiments, the pressure applied is equivalent to a mass of 2 kg. In some embodiments, the pressure applied is equivalent to a mass of 2.5 kg. In some embodiments, the pressure applied is equivalent to a mass of 3 kg. In some embodiments, the pressure applied is equivalent to a mass of 3.5 kg. In some embodiments, the pressure applied is equivalent to a mass of 4 kg. In some embodiments, the pressure applied is equivalent to a mass of 4.5 kg. In some embodiments, the pressure applied is equivalent to a mass of 5 kg.

In some embodiments, the pressure is applied using a garment, such as a belt.

In some embodiments, the suitable skin-ECG sensor impedance is between 100 and 650 kΩ. In some embodiments, the suitable skin-ECG sensor impedance is 602 kΩ. In some embodiments, the suitable skin-ECG sensor impedance is less than 150 kΩ. In some embodiments, the suitable skin-ECG sensor impedance is 227 kΩ. In some embodiments, the suitable skin-ECG sensor impedance is 135 kΩ.

In some embodiments, the cutaneous contact is configured to have skin-ECG sensor impedance of greater than 150 kΩ.

In some embodiments, the cutaneous contact is configured to have skin-ECG sensor impedance of less than 150 kΩ.

In some embodiments, the cutaneous contact is configured to have skin-ECG sensor impedance of between 5 to 150 kΩ. In some embodiments, the cutaneous contact is configured to have skin-ECG sensor impedance of between 10 to 150 kΩ. In some embodiments, the cutaneous contact is configured to have skin-ECG sensor impedance of between 20 to 150 kΩ. In some embodiments, the cutaneous contact is configured to have skin-ECG sensor impedance of between 30 to 150 kΩ. In some embodiments, the cutaneous contact is configured to have skin-ECG sensor impedance of between 40 to 150 kΩ. In some embodiments, the cutaneous contact is configured to have skin-ECG sensor impedance of between 50 to 150 kΩ. In some embodiments, the cutaneous contact is configured to have skin-ECG sensor impedance of between 60 to 150 kΩ. In some embodiments, the cutaneous contact is configured to have skin-ECG sensor impedance of between 70 to 150 kΩ. In some embodiments, the cutaneous contact is configured to have skin-ECG sensor impedance of between 80 to 150 kΩ. In some embodiments, the cutaneous contact is configured to have skin-ECG sensor impedance of between 90 to 150 kΩ. In some embodiments, the cutaneous contact is configured to have skin-ECG sensor impedance of between 100 to 150 kΩ. In some embodiments, the cutaneous contact is configured to have skin-ECG sensor impedance of between 110 to 150 kΩ. In some embodiments, the cutaneous contact is configured to have skin-ECG sensor impedance of between 120 to 150 kΩ. In some embodiments, the cutaneous contact is configured to have skin-ECG sensor impedance of between 130 to 150 kΩ. In some embodiments, the cutaneous contact is configured to have skin-ECG sensor impedance of between 140 to 150 kΩ.

In some embodiments, the cutaneous contact is attached to an elastomeric structure that is configured to deform when placed on the abdomen of the pregnant human subject to create a skin-ECG sensor impedance of less than 150 kΩ.

In some embodiments, the cutaneous contact is attached to an elastomeric structure that is configured to deform when placed on the abdomen of the pregnant human subject to create a skin-ECG sensor impedance of between 5 to 150 kΩ. In some embodiments, the cutaneous contact is attached to an elastomeric structure that is configured to deform when placed on the abdomen of the pregnant human subject to create a skin-ECG sensor impedance of between 10 to 150 kΩ. In some embodiments, the cutaneous contact is attached to an elastomeric structure that is configured to deform when placed on the abdomen of the pregnant human subject to create a skin-ECG sensor impedance of between 20 to 150 kΩ. In some embodiments, the cutaneous contact is attached to an elastomeric structure that is configured to deform when placed on the abdomen of the pregnant human subject to create a skin-ECG sensor impedance of between 30 to 150 kΩ. In some embodiments, the cutaneous contact is attached to an elastomeric structure that is configured to deform when placed on the abdomen of the pregnant human subject to create a skin-ECG sensor impedance of between 40 to 150 kΩ. In some embodiments, the cutaneous contact is attached to an elastomeric structure that is configured to deform when placed on the abdomen of the pregnant human subject to create a skin-ECG sensor impedance of between 50 to 150 kΩ. In some embodiments, the cutaneous contact is attached to an elastomeric structure that is configured to deform when placed on the abdomen of the pregnant human subject to create a skin-ECG sensor impedance of between 60 to 150 kΩ. In some embodiments, the cutaneous contact is attached to an elastomeric structure that is configured to deform when placed on the abdomen of the pregnant human subject to create a skin-ECG sensor impedance of between 70 to 150 kΩ. In some embodiments, the cutaneous contact is attached to an elastomeric structure that is configured to deform when placed on the abdomen of the pregnant human subject to create a skin-ECG sensor impedance of between 80 to 150 kΩ. In some embodiments, the cutaneous contact is attached to an elastomeric structure that is configured to deform when placed on the abdomen of the pregnant human subject to create a skin-ECG sensor impedance of between 90 to 150 kΩ. In some embodiments, the cutaneous contact is attached to an elastomeric structure that is configured to deform when placed on the abdomen of the pregnant human subject to create a skin-ECG sensor impedance of between 100 to 150 kΩ. In some embodiments, the cutaneous contact is attached to an elastomeric structure that is configured to deform when placed on the abdomen of the pregnant human subject to create a skin-ECG sensor impedance of between 110 to 150 kΩ. In some embodiments, the cutaneous contact is attached to an elastomeric structure that is configured to deform when placed on the abdomen of the pregnant human subject to create a skin-ECG sensor impedance of between 120 to 150 kΩ. In some embodiments, the cutaneous contact is attached to an elastomeric structure that is configured to deform when placed on the abdomen of the pregnant human subject to create a skin-ECG sensor impedance of between 130 to 150 kΩ. In some embodiments, the cutaneous contact is attached to an elastomeric structure that is configured to deform when placed on the abdomen of the pregnant human subject to create a skin-ECG sensor impedance of between 140 to 150 kΩ.

In some embodiments, the ECG sensor is configured to have a surface resistance suitable for sensing fetal electrocardiogram signals from a pregnant human subject. In some embodiments, the cutaneous contact is configured to have a surface resistance of less than 1 Ω/square. In some embodiments, the cutaneous contact is configured to have a surface resistance between 0.01 and 1 Ω/square.

In some embodiments, the cutaneous contact is configured to have a surface resistance of 0.01 Ω/square. In some embodiments, the cutaneous contact is configured to have a surface resistance of 0.02 Ω/square. In some embodiments, the cutaneous contact is configured to have a surface resistance of 0.03 Ω/square. In some embodiments, the cutaneous contact is configured to have a surface resistance of 0.04 Ω/square. In some embodiments, the cutaneous contact is configured to have a surface resistance of 0.05 Ω/square. In some embodiments, the cutaneous contact is configured to have a surface resistance of 0.06 Ω/square. In some embodiments, the cutaneous contact is configured to have a surface resistance of 0.07 Ω/square. In some embodiments, the cutaneous contact is configured to have a surface resistance of 0.08 Ω/square. In some embodiments, the cutaneous contact is configured to have a surface resistance of 0.09 Ω/square. In some embodiments, the cutaneous contact is configured to have a surface resistance of 0.1 Ω/square. In some embodiments, the cutaneous contact is configured to have a surface resistance of 0.2 Ω/square. In some embodiments, the cutaneous contact is configured to have a surface resistance of 0.3 Ω/square. In some embodiments, the cutaneous contact is configured to have a surface resistance of 0.4 Ω/square. In some embodiments, the cutaneous contact is configured to have a surface resistance of 0.5 Ω/square. In some embodiments, the cutaneous contact is configured to have a surface resistance of 0.6 Ω/square. In some embodiments, the cutaneous contact is configured to have a surface resistance of 0.7 Ω/square. In some embodiments, the cutaneous contact is configured to have a surface resistance of 0.8 Ω/square. In some embodiments, the cutaneous contact is configured to have a surface resistance of 0.9 Ω/square. In some embodiments, the cutaneous contact is configured to have a surface resistance of 1 Ω/square.

In some embodiments, the ECG sensor is configured to have a capacitance suitable for sensing fetal electrocardiogram signals from a pregnant human subject. In some embodiments, the capacitance is from 1 nF to 0.5 μF. In some embodiments, the capacitance is 5 nF. In some embodiments, the capacitance is 10 nF. In some embodiments, the capacitance is 15 nF. In some embodiments, the capacitance is 20 nF. In some embodiments, the capacitance is 25 nF. In some embodiments, the capacitance is 30 nF. In some embodiments, the capacitance is 35 nF. In some embodiments, the capacitance is 40 nF. In some embodiments, the capacitance is 45 nF. In some embodiments, the capacitance is 50 nF. In some embodiments, the capacitance is 60 nF. In some embodiments, the capacitance is 70 nF. In some embodiments, the capacitance is 80 nF. In some embodiments, the capacitance is 90 nF. In some embodiments, the capacitance is 80 nF. In some embodiments, the capacitance is 0.1 μF. In some embodiments, the capacitance is 80 nF. In some embodiments, the capacitance is 0.2 μF. In some embodiments, the capacitance is 80 nF. In some embodiments, the capacitance is 0.3 μF. In some embodiments, the capacitance is 80 nF. In some embodiments, the capacitance is 0.4 μF. In some embodiments, the capacitance is 80 nF. In some embodiments, the capacitance is 0.5 μF.

Without intending to be limited to any particular theory, the capacitance of the ECG sensors increases as the surface area of the cutaneous contact that contacts the skin of the pregnant human subject increases. Additionally, without intending to be limited to any particular theory, the capacitance of the ECG sensors decreases as the pressure applied to the cutaneous contact increases.

In some embodiments, the ECG sensor is configured to detect a fetal electrocardiogram signal having a signal to noise ratio between −20 dB and 50 dB. In some embodiments, the ECG sensor is configured to detect a fetal electrocardiogram signal having a signal to noise ratio between 0 dB and 50 dB. In some embodiments, the ECG sensor is configured to detect a fetal electrocardiogram signal having a signal to noise ratio less than 50 dB.

The Cutaneous Contact

In some embodiments, the cutaneous contact is an electrically conductive fabric. Electrically conductive fabrics can be made with conductive fibers, such as, for example, metal strands woven into the construction of the fabric. Examples of electrically conductive fabrics suitable for use in ECG sensors according to some embodiments of the present invention include, but are not limited to, the textile ECG sensors disclosed in *Sensors,* 12 16907-16919, 2012. Another example of electrically conductive fabrics suitable for use in ECG sensors according to some embodiments of the present invention include, but are not limited to, the textile ECG sensors disclosed in *Sensors,* 14 11957-11992, 2014.

The electrically conductive fabric may be stretchable. Alternatively, the electrically conductive fabric may not be stretchable. The electrically conductive fabric may be capable of stretching up to 50%, alternatively, 40%, alternatively, 30%, alternatively 20%, alternatively 20%, alternatively, 10%, alternatively, 9%, alternatively, 8%, alternatively, 7%, alternatively, 6%, alternatively, 5%, alternatively, 4%, alternatively, 3%, alternatively, 2%, alternatively, 1%.

In some embodiments, the electrically conductive fabric is anisotropic. In some embodiments, the anisotropy is from 50% to 100%. As used herein, the term anisotropy refers to the difference in resistance of the electrically conductive fabric measured in the main direction, compared to the direction perpendicular to the main direction. As used herein, the term "main direction refers to the direction that the fabric was woven. In some embodiments, the anisotropy of the electrically conductive fabric is configured to have an anisotropy suitable for sensing fetal electrocardiogram signals from a pregnant human subject. In some embodiments, the anisotropy is 62%.

In some embodiments, the electrically conductive fabric is configured to be oriented so the current recorded is the electrical activity that is generated by the fetal and/or maternal heart, and flows along the main direction of the fabric to the lead wire. In some embodiments, the electrically conductive fabric is configured to be oriented so the current recorded is the electrical activity that is generated by the fetal and/or maternal heart, and flows along the direction of the fabric having the least resistance to the lead wire.

In some embodiments, the conductivity of one side of the electrically conductive fabric is greater than the other. In some embodiments, the side of the electrically conductive fabric with the greater conductivity forms cutaneous contact.

In some embodiments, the electrically conductive fabric has a thickness between 0.3 and 0.5 mm. In some embodiments, the thickness of the electrically conductive fabric is 0.3 mm. In some embodiments, the thickness of the electrically conductive fabric is 0.4 mm. In some embodiments, the thickness of the electrically conductive fabric is 0.5 mm.

Figure 9:
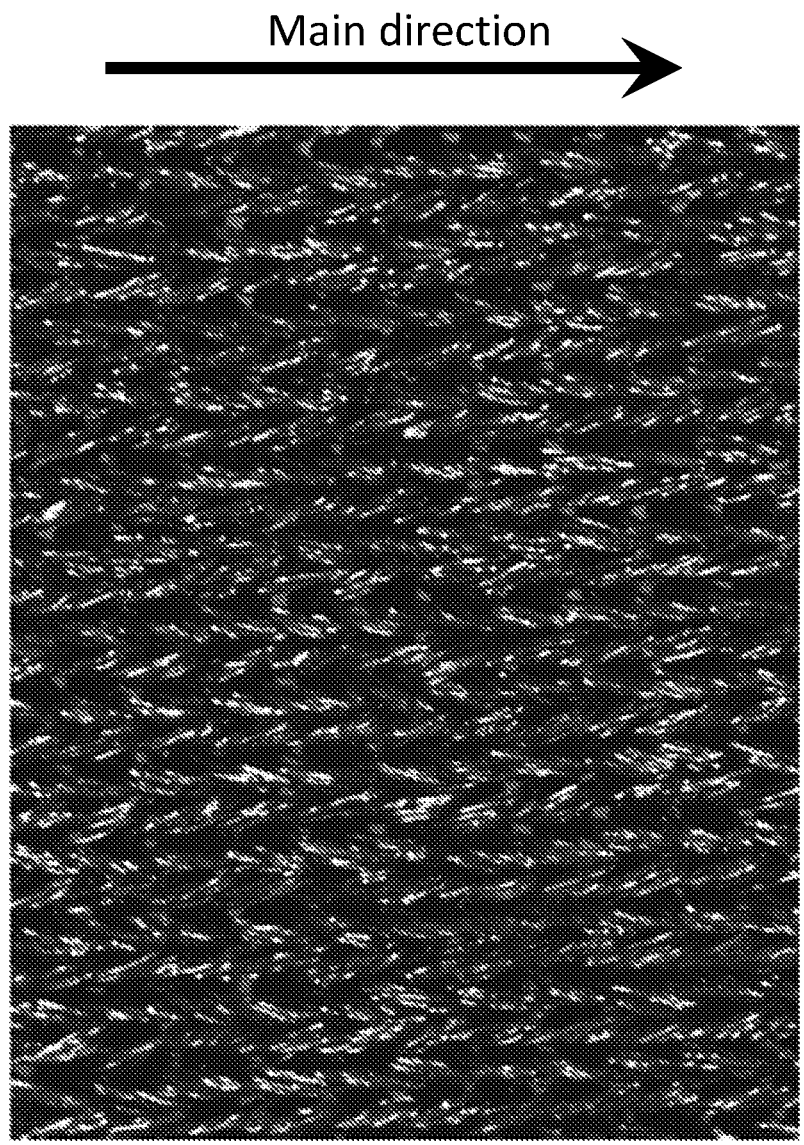
FIG. 9 shows a micrograph of electrically conductive fabric suitable as a cutaneous contact according to some embodiments of the present invention.

In some embodiments, the electrically conductive fabric is the silver-based conductive fabric sold under the tradename ORANGE IT. An example of this electrically conductive fabric is shown in FIG. 9.

In some embodiments, the electrically conductive fabric is the silver-based conductive fabric sold under the tradename C+, sold by Clothing+, St. Petersburg, Fla., USA. An example of this electrically conductive fabric is shown in FIG. 10.

Figure 11:
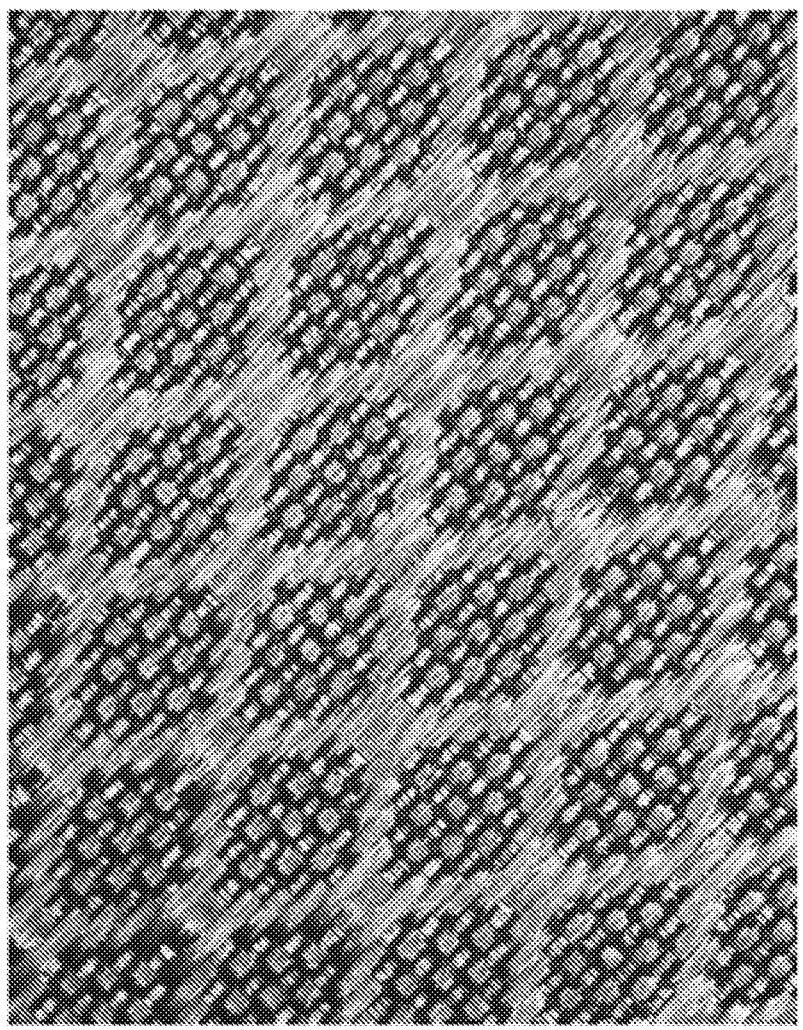
FIG. 11 shows a micrograph of electrically conductive fabric suitable as a cutaneous contact according to some embodiments of the present invention.

In some embodiments, the electrically conductive fabric is the silver-based conductive fabric sold under the tradename SHAOXING17, sold by Shaoxing Yunjia Textile Product Co. Ltd., Zhejiang, China. An example of this electrically conductive fabric is shown in FIG. 11.

Figure 12:
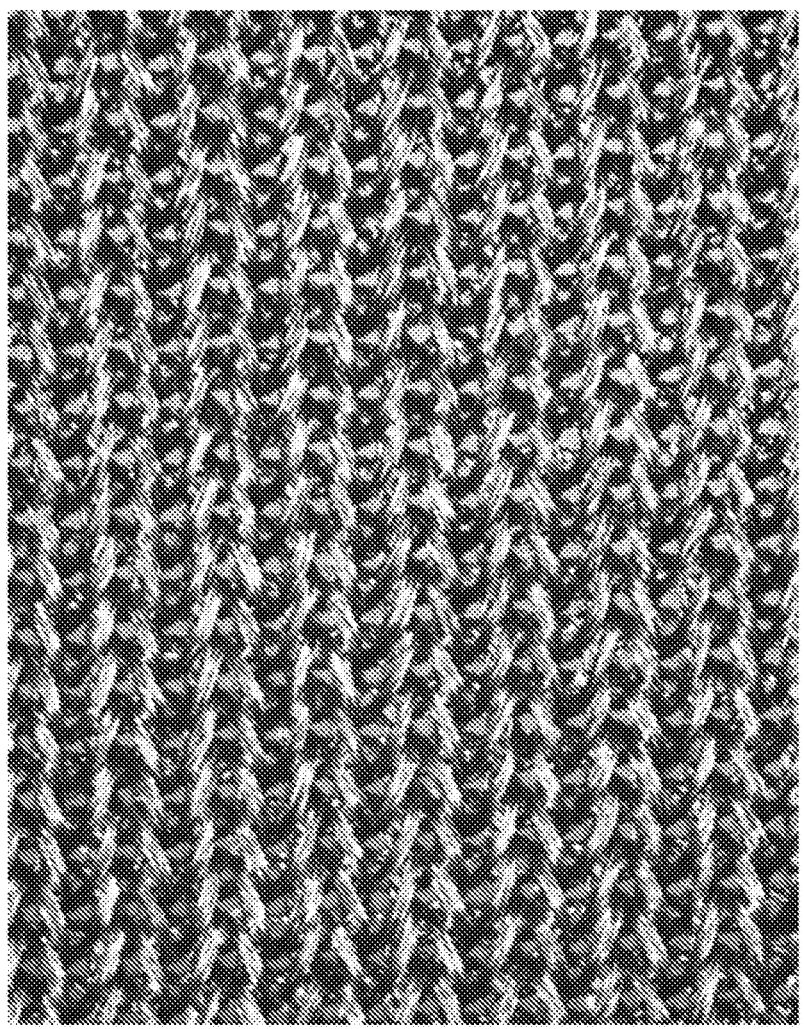
FIG. 12 shows a micrograph of electrically conductive fabric suitable as a cutaneous contact according to some embodiments of the present invention.

In some embodiments, the electrically conductive fabric is the silver-based conductive fabric sold under the tradename SHAOXING27, sold by Shaoxing Yunjia Textile Product Co. Ltd., Zhejiang, China. An example of this electrically conductive fabric is shown in FIG. 12.

Figure 13:
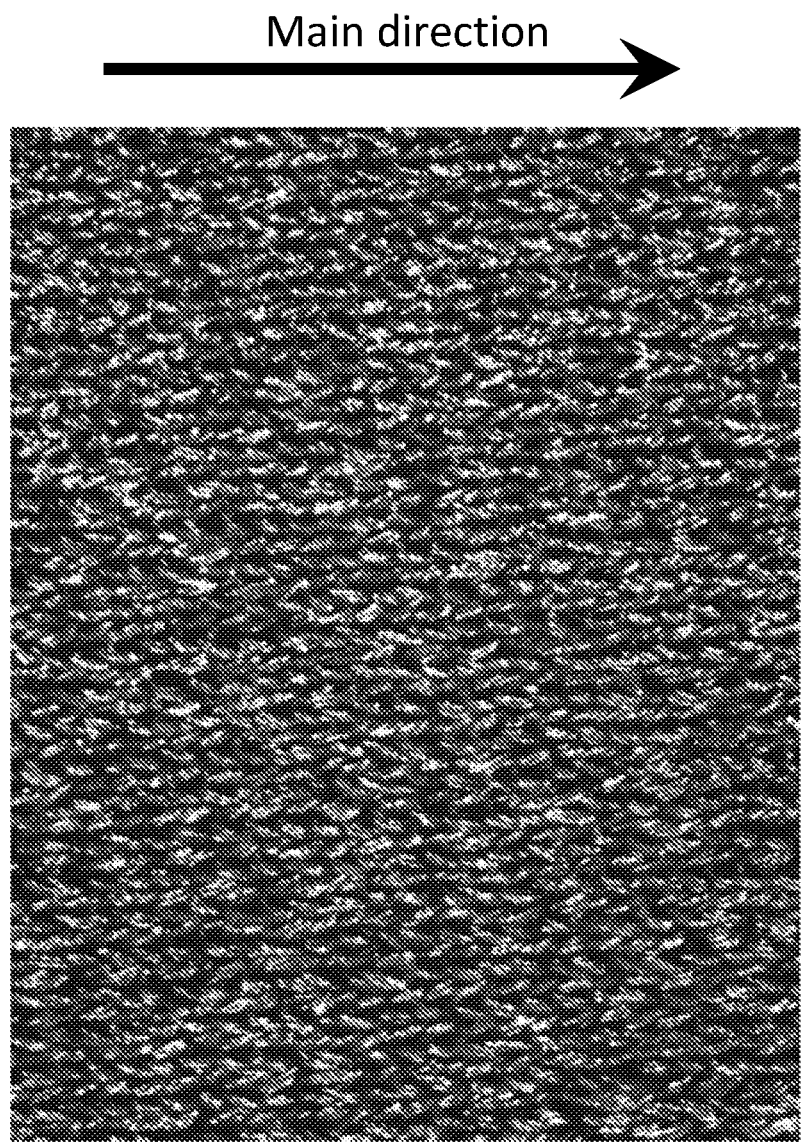
FIG. 13 shows a micrograph of electrically conductive fabric suitable as a cutaneous contact according to some embodiments of the present invention.
Figure 15:
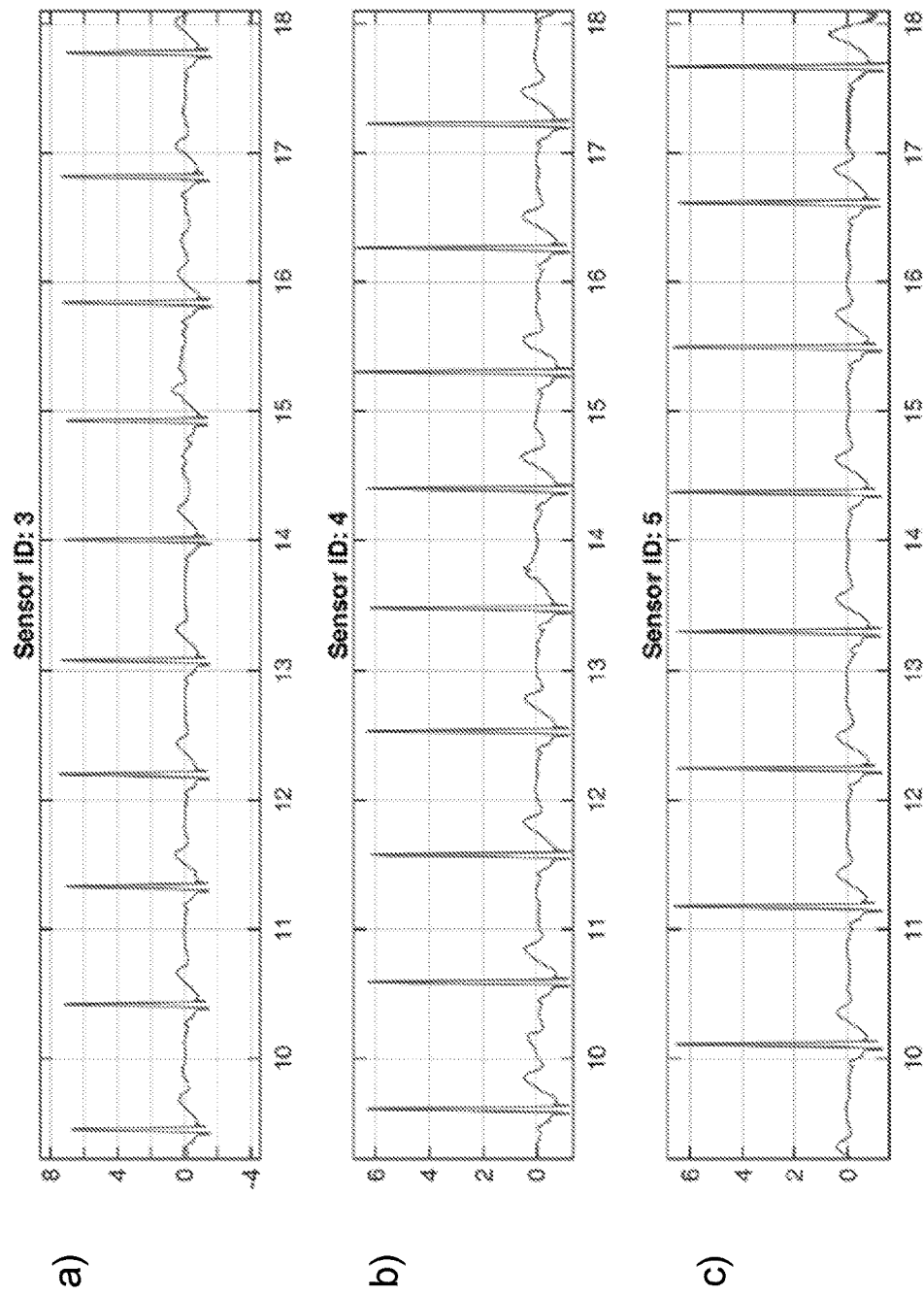
FIG. 15, panels a-c show recorded ECG signals data using electrode serial nos. 3-5 respectively.

In some embodiments, the electrically conductive fabric is the silver-based conductive fabric sold under the tradename SHIELDEX TECHNIK-TEX P130-B, sold by Shieldex Trading USA, Palmyra, N.Y., USA. An example of this electrically conductive fabric is shown in FIG. 13.

In some embodiments, the electrically conductive fabric is the silver-based conductive fabric sold under the tradename SILVER30, sold by Shaoxing Yunjia Textile Product Co. Ltd., Zhejiang, China. An example of this electrically conductive fabric is shown in FIG. 14.

Acoustic Sensors According to Some Embodiments of the Present Invention

In one embodiment, the present invention provides an acoustic sensor configured to detect fetal cardiac activity signals, comprising:

a) a body formed of a solid integral mass having a circular apron with two opposite major side walls,
  a. one side wall being concave in configuration and the other side wall having a rearwardly facing portion coaxially formed thereon, the rearwardly facing portion defining an attachment for a microphone;
  b. an opening coaxially formed through the rearwardly facing portion; and
  c. an annular edge connecting the periphery of the side walls;
b) a microphone, attached to the rearwardly facing portion, wherein the microphone is configured to produce electrical signals in response to acoustic signals transmitted from an abdomen of a pregnant subject;
c) a flexible membrane covering the one side wall, wherein the edge of the flexible membrane covers the annular edge of the one side wall,
  wherein the flexible membrane is configured to contact the skin of the human pregnant subject,
  wherein the flexible membrane is configured to transduce transmitted acoustic signals to the body; and
  wherein the body is configured to transmit the transduced acoustic signals to the microphone;
d) an electrical conductor electrically connected to the microphone; and
e) a connector in electrical contact with the electrical conductor for connection to a lead wire.

In some embodiments, the acoustic sensor is configured to compensate for the changes in sound propagation caused by the skin-air interface. Acoustic signals comprise sound waves or vibrations that propagate as a mechanical wave of pressure and displacement, through a medium such as air, water, or the body. Without intending to be limited to any particular theory, the behavior of sound propagation can be affected by the relationship between the density and pressure of the medium though which the sound wave propagates. Also, the behavior of sound propagation can be affected by the motion of the medium though which the sound wave propagates. Furthermore, the behavior of sound propagation can be affected by the viscosity of the medium though which the sound wave propagates.

Without intending to be limited to any particular theory, during a normal cardiac contraction cycle, the hear produces the following sounds: $S_1$, which corresponds to the QRS complex of the cardiac electrical activity observed during a normal cardiac contraction cycle, and is caused by the block of reverse blood flow due to closure of the tricuspid and mitral (bicuspid) valves, at the beginning of ventricular contraction, or systole. $S_2$, which corresponds to the T wave of the cardiac electrical activity observed during a normal cardiac contraction cycle, and is caused by the closure of the aortic and pulmonary valves.

Figure 22:
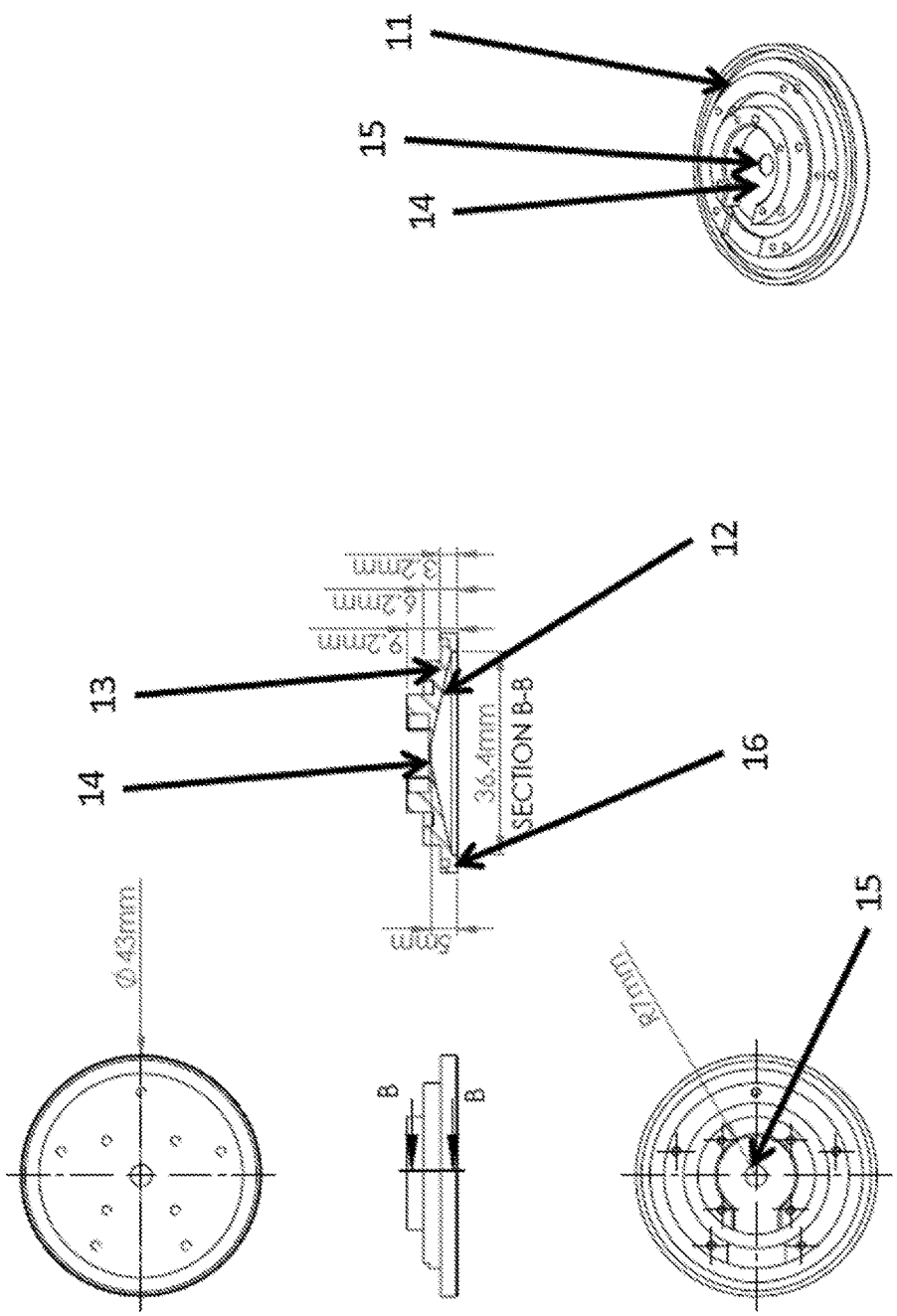
FIG. 22 shows a body of an acoustic sensor according to some embodiments of the present invention.
Figure 23:
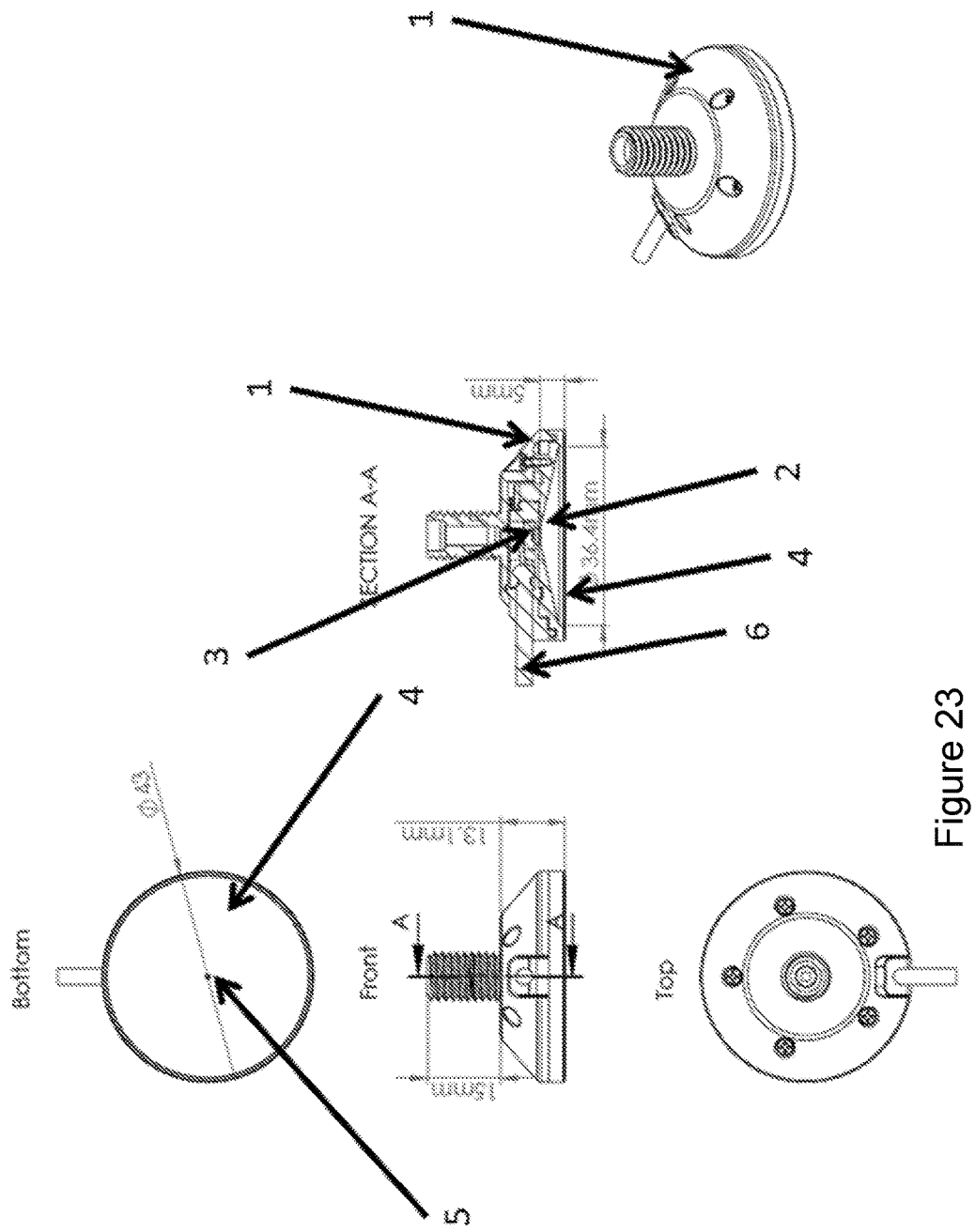
FIG. 23 shows a body of an acoustic sensor located within a housing according to some embodiments of the present invention.

Referring to FIG. 22 and FIG. 23, the at least one acoustic sensor comprises a body (11) formed of a solid integral mass having a circular apron with two opposite major side walls (12) and (13); one side wall (12) being concave in configuration and the other side wall (13) having a rearwardly facing portion (14) coaxially formed thereon, the rearwardly facing portion (14) defining an attachment for a microphone; an opening (15) coaxially formed through the rearwardly facing portion; and an annular edge (16) connecting the periphery of the side walls; a microphone (17), attached to the rearwardly facing portion (14), wherein the microphone (17) is configured to produce electrical signals in response to acoustic signals transmitted from an abdomen of a pregnant subject; a flexible membrane (18) covering the one side wall, wherein the edge of the flexible membrane (18) covers the annular edge (16) of the one side wall, wherein the flexible membrane (18) is configured to contact the skin of the human pregnant subject, wherein the flexible membrane (18) is configured to transduce transmitted acoustic signals to the body (11); and wherein the body (11) is configured to transmit the transduced acoustic signals to the microphone (17); an electrical conductor electrically connected to the microphone; and a connector in electrical contact with the electrical conductor for connection to a lead wire.

In some embodiments, the microphone (17) is lockingly engaged on the rearwardly facing portion (14) via friction. Alternative mechanisms to lockingly engage the microphone (17) on the rearwardly facing portion (14) include adhesive, screw threads, and the like.

Figure 24:
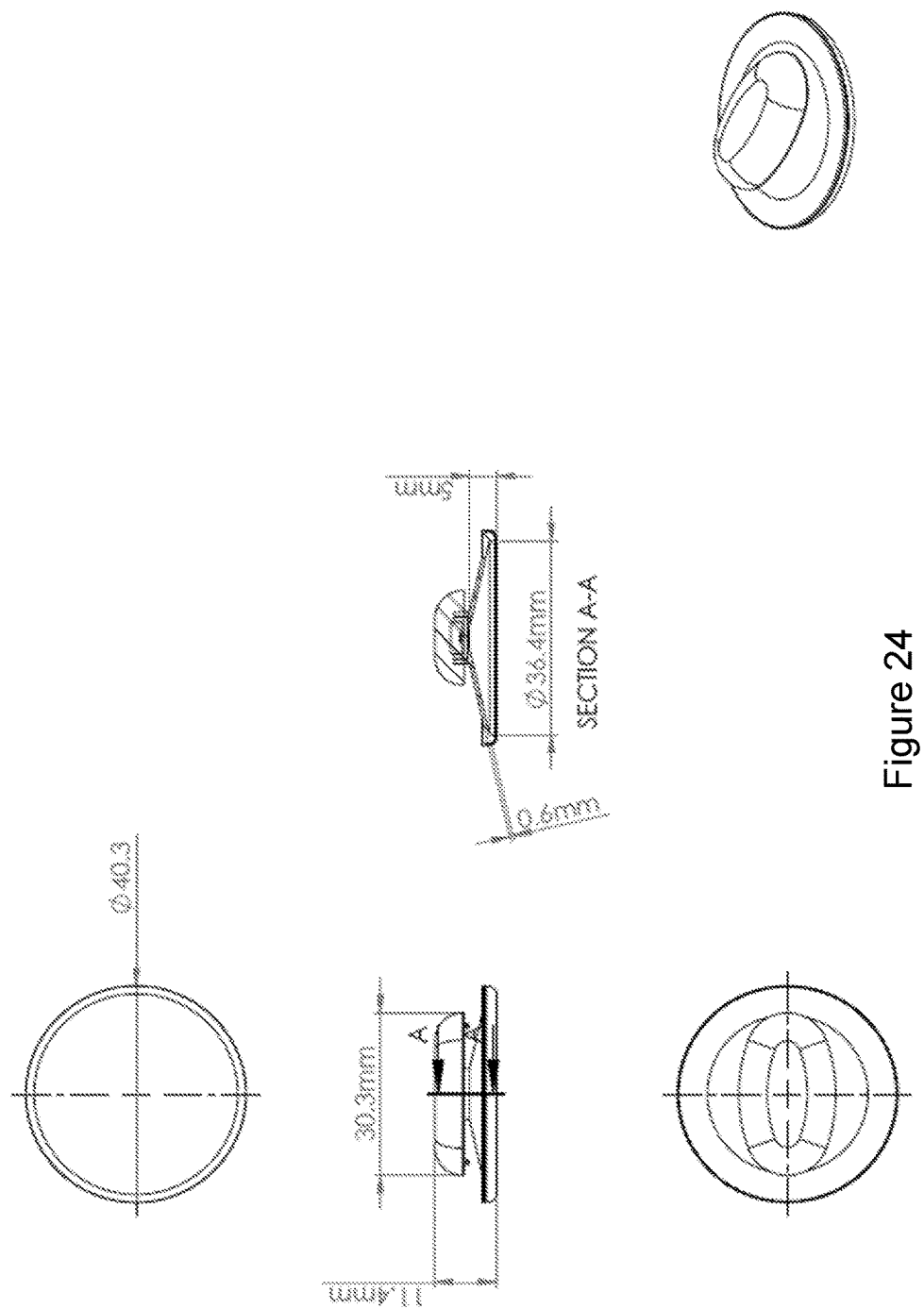
FIG. 24 shows another housing according to some embodiments of the present invention.

Referring to FIG. 24, in some embodiments, the microphone is lockingly engaged in a structure configured to isolate the microphone (17) from acoustic signals not from the abdomen of the pregnant human subject, and position the microphone (17) on the rearwardly facing portion (14). Examples of acoustic signals not from the abdomen of the pregnant human subject include, but are not limited to sounds caused by movement of the pregnant human subject, or environmental noise.

In some embodiments, the microphone (17) is lockingly engaged in the structure configured to isolate the microphone (17) from acoustic signals not from the abdomen of the pregnant human subject by friction. Alternative mechanisms to lockingly engage the microphone (17) in the structure configured to isolate the microphone (17) from acoustic signals not from the abdomen of the pregnant human subject include adhesive, screw threads, and the like.

In the embodiment shown in FIG. 23, the flexible membrane (18) has a hole (19). Alternatively, the flexible membrane (18) lacks a hole, and the flexible membrane (18) forms an air-tight chamber, defined by the body (11) and the flexible membrane (18).

In some embodiments, the present invention provides at least one acoustic sensor configured to detect fetal cardiac activity signals, comprising:
a) a body (11) formed of a solid integral mass having a circular apron with two opposite major side walls (12) and (13),
  i. one side wall (12) being concave in configuration and the other side wall (13) having a rearwardly facing portion (14) coaxially formed thereon, the rearwardly facing portion defining an attachment for a microphone;
  ii. an opening (15) coaxially formed through the rearwardly facing portion; and
  iii. an annular edge (16) connecting the periphery of the side walls (12) and (13);
b) a microphone (17), attached to the rearwardly facing portion (14),
  wherein the microphone (17) is configured to produce electrical signals in response to acoustic signals transmitted from an abdomen of a pregnant subject;
c) a flexible membrane (18) covering the one side wall, wherein the edge of the flexible membrane (18) covers the annular edge (16) of the one side wall,
  wherein the flexible membrane (18) is configured to contact the skin of the human pregnant subject,
  wherein the flexible membrane (18) is configured to transduce transmitted acoustic signals to the body (11); and
  wherein the body (11) is configured to transmit the transduced acoustic signals to the microphone (17);
d) an electrical conductor electrically connected to the microphone; and
e) a connector in electrical contact with the electrical conductor for connection to a lead wire.

In some embodiments, the at least one acoustic sensor is configured to reduce the acoustic impedance mismatch between skin and air, thereby improving the performance of the at least one sensor.

Without intending to be limited to any particular theory, the body (11) is configured to detect fetal cardiac activity, but isolate the microphone (17) from acoustic signals not from the abdomen of the pregnant human subject, and position the microphone (17) at the opening (15). Examples of acoustic signals not from the abdomen of the pregnant human subject include, but are not limited to sounds caused by movement of the pregnant human subject, or environmental noise. The sensitivity of the at least one acoustic sensor according to some embodiments of the present invention to fetal cardiac activity can be altered by varying one or more parameters selected from the group consisting of: the flexibility of the flexible membrane, the diameter of the body, the sensitivity of the microphone, the material of the body, the size of the body, the height of the cone defined by the concave configuration of the side wall (12), the material of the isolation structure, and the algorithm used to extract fetal cardiac activity data from acoustic signals.

Figure 25:
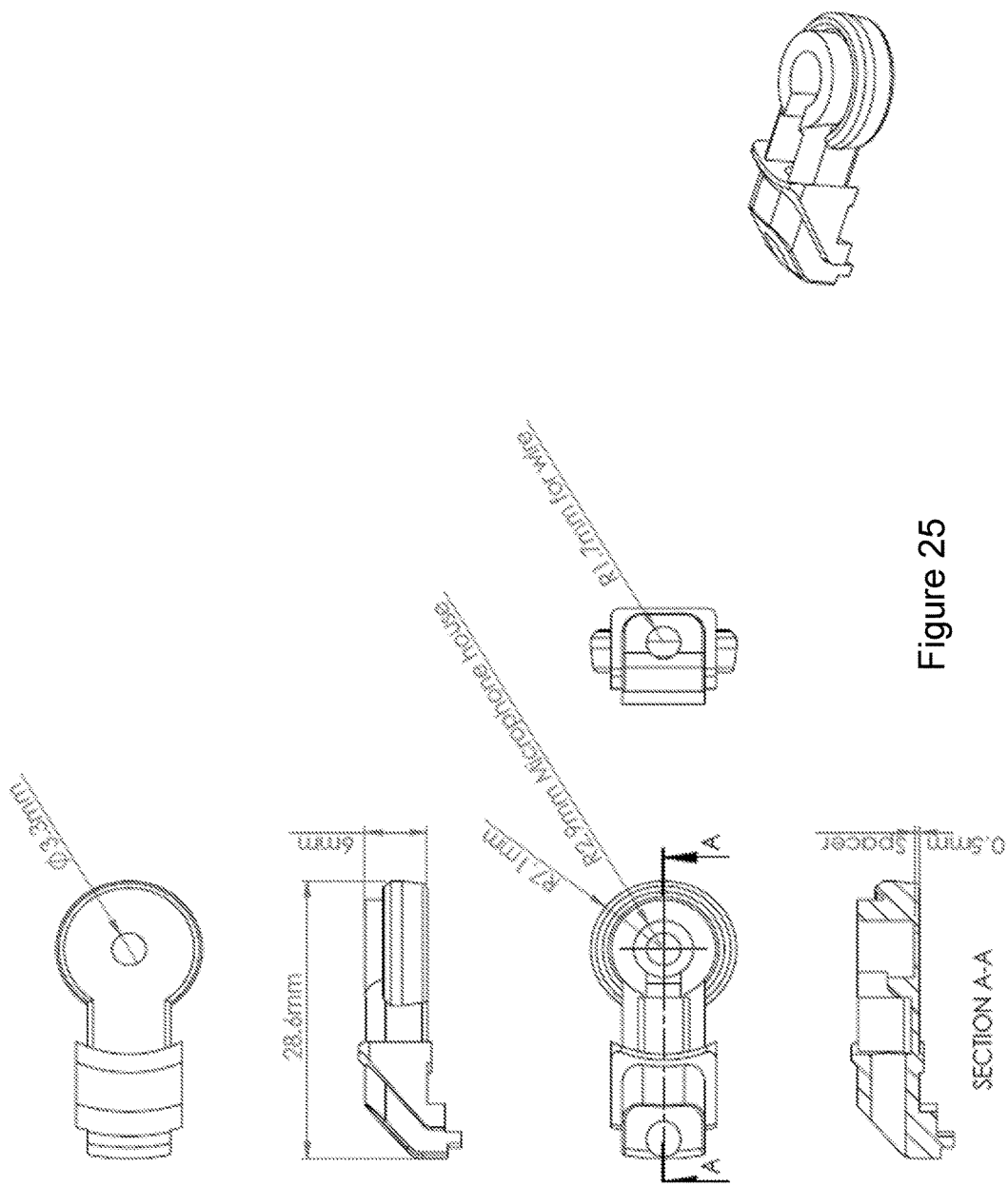
FIG. 25 shows a structure configured to isolate the microphone from acoustic signals not from the abdomen of the pregnant human subject.
Figure 26:
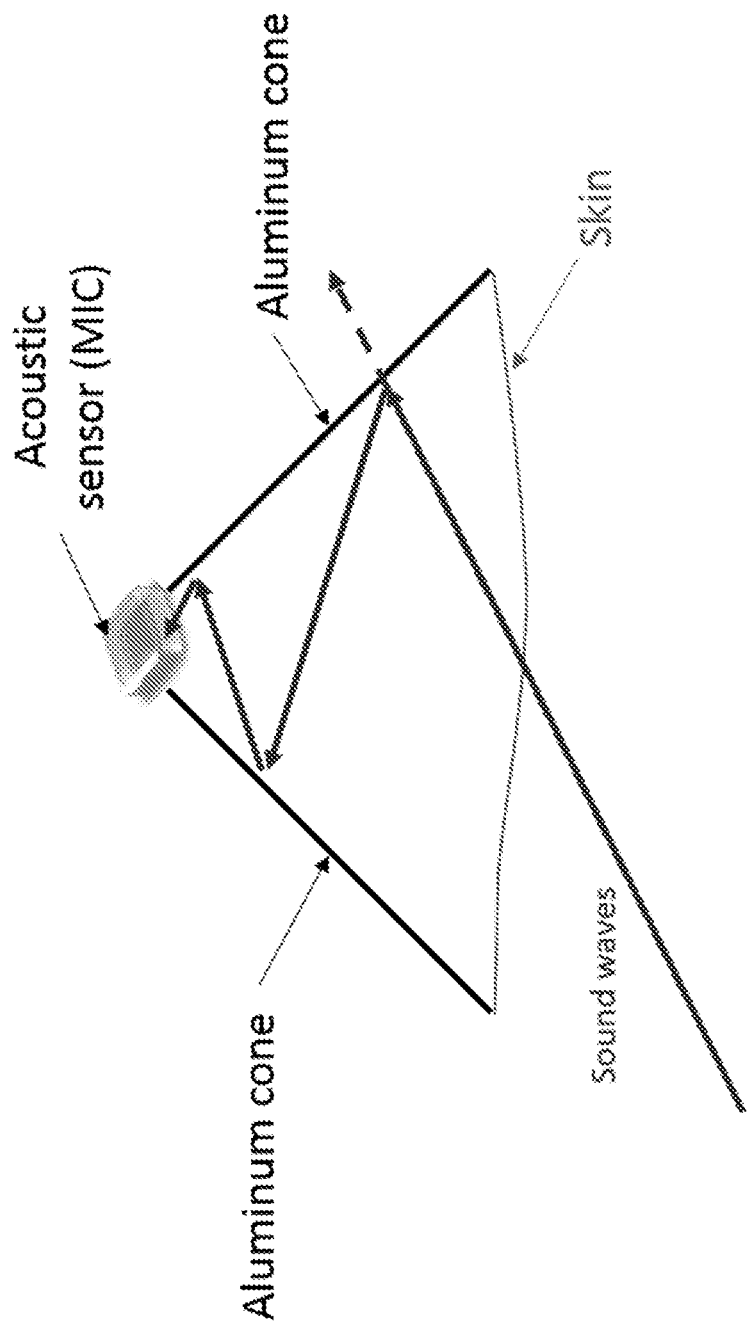
FIG. 26 shows a representation of the transduction of acoustic signals using an acoustic sensor according to some embodiments of the present invention.

For example, by way of illustration, a larger acoustic sensor would be able collect more acoustic signals than a smaller one. By way of another illustration, an aluminum body would reflect sound waves more efficiently (see, for example FIG. 25 than a plastic body.)

In some embodiments, the body (11) is circular, with an outer diameter configured to detect fetal cardiac activity. In some embodiments, the body (11) is circular, with an outer diameter of 20 mm to 60 mm. In some embodiments, body (11) is circular, with an outer diameter of 60 mm. In some embodiments, body (11) is circular, with an outer diameter of 50 mm. In some embodiments, body (11) is circular, with an outer diameter of 43 mm. In some embodiments, body (11) is circular, with an outer diameter of 40 mm. In some embodiments, body (11) is circular, with an outer diameter of 30 mm. In some embodiments, housing is body (11), with an outer diameter of 20 mm.

In some embodiments, the body (11) is non-circular in shape. Examples of non-circular shapes suitable for use according to some embodiments of the present invention include, but are not limited to, oval, square, rectangular, and the like.

In one embodiment, the distance between the two side walls (2) and (3) defines a thickness, wherein the thickness has a minimum value between 0.3 mm to 5 mm. In some embodiments, the thickness is configured to detect fetal cardiac activity. In some embodiments, the thickness is 5 mm. Alternatively, the thickness is 4 mm. Alternatively, the thickness is 3 mm. Alternatively, the thickness is 2 mm. Alternatively, the thickness is 1 mm. Alternatively, the thickness is 0.9 mm. Alternatively, the thickness is 0.8 mm. Alternatively, the thickness is 0.7 mm. Alternatively, the thickness is 0.6 mm. Alternatively, the thickness is 0.5 mm. Alternatively, the thickness is 0.4 mm. Alternatively, the thickness is 0.3 mm.

In some embodiments, the concave configuration of the side wall (12) defines a cone with a height from 1 mm to 15 mm. In some embodiments, the height of the cone is configured to detect fetal cardiac activity. In some embodiments, the height of the cone is 15 mm. Alternatively, in some embodiments, the height of the cone is 14 mm.

Alternatively, in some embodiments, the height of the cone is 13 mm. Alternatively, in some embodiments, the height of the cone is 12 mm. Alternatively, in some embodiments, the height of the cone is 11 mm. Alternatively, in some embodiments, the height of the cone is 10 mm. Alternatively, in some embodiments, the height of the cone is 9 mm. Alternatively, in some embodiments, the height of the cone is 8 mm. Alternatively, in some embodiments, the height of the cone is 7 mm. Alternatively, in some embodiments, the height of the cone is 6 mm. Alternatively, in some embodiments, the height of the cone is 5 mm. Alternatively, in some embodiments, the height of the cone is 4 mm. Alternatively, in some embodiments, the height of the cone is 3 mm. Alternatively, in some embodiments, the height of the cone is 2 mm. Alternatively, in some embodiments, the height of the cone is 1 mm.

In some embodiments, the height of the cone is less than or equal to ¼ the diameter of the base of the body (11).

In some embodiments, the body (11) is configured to have an acoustic gain of 50 dB. Alternatively, in some embodiments, the body (11) is configured to have an acoustic gain of 40 dB. Alternatively, in some embodiments, the body (11) is configured to have an acoustic gain of 30 dB. Alternatively, in some embodiments, the body (11) is configured to have an acoustic gain of 20 dB. Alternatively, in some embodiments, the body (11) is configured to have an acoustic gain of 10 dB.

In some embodiments, the acoustic gain is greater than the loss in transmission of the acoustic signal between skin and air as a result of the impedance mismatch.

In some embodiments, the loss in transmission is calculated using the equation:

$$\tau = 4 \frac{Z_{air} * Z_{skin}}{(Z_{air} + Z_{skin})^2}$$

$$\rightarrow \tau \cong -29 \text{ dB}$$

Where:
$Z_{air}$ is the equivalent acoustic impedance of air
$Z_{skin}$ is the equivalent acoustic impedance of skin In some embodiments, the minimum acoustic gain $G_{min}$ required to compensate the loss $\tau$ is approximated using the equation:

$$\propto \frac{A_{base}}{A_{hole}} = \left(\frac{D_{base}}{D_{hole}}\right)^2 = \left(\frac{R_{base}}{r_{hole}}\right)^2$$

$$G_{min} = 29 \text{ dB} = 10\log10\left(\left(\frac{R_{base}}{r_{hole}}\right)^2\right) = 20\log10\left(\frac{R_{base}}{r_{hole}}\right)$$

$$\rightarrow \frac{R_{base}}{r_{hole}} \geq 10^{\frac{29}{20}} = 28$$

Where:
$A_{base}$ is the space of the base
$A_{hole}$ is the space of the hole
$R_{base}$ is the radius of the base
$r_{hole}$ is the radius of the hole
$D_{base}$ is the diameter of the base
$D_{hole}$ is the diameter of the hole In some embodiments, the hole (15) has a diameter from 2 mm to 5 mm. In some embodiments, the hole (15) has a diameter of 5 mm. In some embodiments, the hole (15) has a diameter of 4 mm. In some embodiments, the hole (15) has a diameter of 3 mm. In some embodiments, the hole (15) has a diameter of 2 mm.

Referring to FIGS. 23 and 24, in some embodiments, microphone (17) is lockingly engaged within a structure configured to isolate the microphone (17) from acoustic signals not from the abdomen of the pregnant human subject, and wherein the structure is configured to locate the microphone over the hole (15). In some embodiments, the structure is has a spacer from 0.2 to 2 mm. In some embodiments, the spacer is 2 mm. In some embodiments, the spacer is 1.9 mm. In some embodiments, the spacer is 1.8 mm. In some embodiments, the spacer is 1.7 mm. In some embodiments, the spacer is 1.6 mm. In some embodiments, the spacer is 1.5 mm. In some embodiments, the spacer is 1.4 mm. In some embodiments, the spacer is 1.3 mm. In some embodiments, the spacer is 1.2 mm. In some embodiments, the spacer is 1.1 mm. In some embodiments, the spacer is 1.0 mm. In some embodiments, the spacer is 0.9 mm. In some embodiments, the spacer is 0.8 mm. In some embodiments, the spacer is 0.7 mm. In some embodiments, the spacer is 0.6 mm. In some embodiments, the spacer is 0.5 mm. In some embodiments, the spacer is 0.4 mm. In some embodiments, the spacer is 0.3 mm. In some embodiments, the spacer is 0.2 mm.

In some embodiments, the structure has a hole that transmits the acoustic signals from the body to the microphone (17). In some embodiments the structure is configured to lockingly engage the microphone (17). In some embodiments, the microphone is lockingly engaged within the structure via an adhesive.

In some embodiments, the structure has a height configured to isolate the microphone (17) from acoustic signals not from the abdomen of the pregnant human subject. In some embodiments, the height is from 0.4 mm to 9 mm. In some embodiments, the height is 9 mm. In some embodiments, the height is 8 mm. In some embodiments, the height is 7 mm. In some embodiments, the height is 6 mm. In some embodiments, the height is 5.5 mm. In some embodiments, the height is 5 mm. In some embodiments, the height is 4.5 mm. In some embodiments, the height is 4 mm. In some embodiments, the height is 3.5 mm. In some embodiments, the height is 3 mm. In some embodiments, the height is 2.5 mm. In some embodiments, the height is 2 mm. In some embodiments, the height is 1.5 mm. In some embodiments, the height is 1 mm. In some embodiments, the height is 0.9 mm. In some embodiments, the height is 0.8 mm. In some embodiments, the height is 0.7 mm. In some embodiments, the height is 0.6 mm. In some embodiments, the height is 0.5 mm. In some embodiments, the height is 0.4 mm.

In some embodiments, the structure comprises a circular portion. In some embodiments, the circular portion is configured to lockingly engage with the rearwardly facing portion (14).

In some embodiments, the circular portion has an outer diameter configured to isolate the microphone (17) from acoustic signals not from the abdomen of the pregnant human subject. In some embodiments, the outer diameter is from 6 mm to 16 mm. In some embodiments, the outer diameter is 16 mm. In some embodiments, the outer diameter is 15 mm. In some embodiments, the outer diameter is 14 mm. In some embodiments, the outer diameter is 13 mm. In some embodiments, the outer diameter is 12 mm. In some embodiments, the outer diameter is 11 mm. In some embodiments, the outer diameter is 10 mm. In some embodiments, the outer diameter is 9 mm. In some embodiments, the outer diameter is 8 mm. In some embodiments, the outer diameter is 7.1 mm. In some embodiments, the outer diameter is 7 mm. In some embodiments, the outer diameter is 6 mm.

In some embodiments the circular portion has an inner diameter configured to house the microphone (17) and isolate the microphone from acoustic signals not from the abdomen of the pregnant human subject. In some embodiments, the inner diameter is from 4 mm to 8 mm. In some embodiments, the inner diameter is 8 mm. In some embodiments, the inner diameter is 7 mm. In some embodiments, the inner diameter is 6 mm. In some embodiments, the inner diameter is 5 mm. In some embodiments, the inner diameter is 4 mm.

In some embodiments, the body (11) is made from a material configured to detect fetal cardiac activity. In some embodiments, the body (11) is made from aluminum. In alternate embodiments, the body (11) is made from brass. In alternate embodiments, the body (11) is made from stainless steel. In alternate embodiments, the body (11) is made from plastic. In some embodiments, the plastic is nylon.

In some embodiments, the structure is made from a material configured to isolate the microphone (17) from acoustic signals not from the abdomen of the pregnant human subject. In some embodiments, the structure is made from Polyurethane 60 shore. In some embodiments, the structure is a resin. Examples of materials suitable for forming the structure include, but are not limited to rubber, Silicone, TPE, TPU, and the like. In some embodiments the Polyurethane's elasticity is from 20 to 80 shore.

In some embodiments, the flexible membrane (18) is attached to the body (11) by adhesive. Alternatively, in some embodiments, the flexible membrane (18) is attached to the body (11) by crimping a portion of the flexible membrane between the body (11) and a housing, by vacuum forming, followed by snapping.

As used herein, the term "flexible" refers to the property of a membrane to deform, both to conform to the skin of the pregnant human subject, but also to transduce acoustic signals with sufficient fidelity to the microphone.

In some embodiments, the size of the flexible membrane (18), the material comprising the flexible membrane (18), the thickness of the flexible membrane (18), or any combination thereof can alter the ability of the flexible membrane (18) to contact the skin of a human pregnant subject and to transduce the acoustic signals. In some embodiments, the flexible membrane (18) is configured to contact the skin of a human pregnant subject and to transduce the acoustic signals. In some embodiments, the flexible membrane (18) is further configured to comprise a hole (19).

In some embodiments, the thickness of the flexible membrane (18) is from 0.2 mm to 0.6 mm. In some embodiments, the thickness of the flexible membrane (18) is 0.6 mm. In some embodiments, the thickness of the flexible membrane (18) is 0.5 mm. In some embodiments, the thickness of the flexible membrane (18) is 0.4 mm. In some embodiments, the thickness of the flexible membrane (18) is 0.3 mm. In some embodiments, the thickness of the flexible membrane (18) is 0.2 mm.

In some embodiments, the density of the flexible membrane (18) is 900 kg/m$^3$ to 1900 kg/m3. In some embodiments, the density of the flexible membrane (18) is 1900 kg/m$^3$. In some embodiments, the density of the flexible membrane (18) is 1800 kg/m$^3$. In some embodiments, the density of the flexible membrane (18) is 1700 kg/m$^3$. In some embodiments, the density of the flexible membrane (18) is 1600 kg/m$^3$. In some embodiments, the density of the flexible membrane (18) is 1500 kg/m$^3$. In some embodiments, the density of the flexible membrane (18) is 1400 kg/m$^3$. In some embodiments, the density of the flexible membrane (18) is 1300 kg/m$^3$. In some embodiments, the density of the flexible membrane (18) is 1200 kg/m$^3$. In some embodiments, the density of the flexible membrane (18) is 1100 kg/m$^3$. In some embodiments, the density of the flexible membrane (18) is 1000 kg/m$^3$. In some embodiments, the density of the flexible membrane (18) is 900 kg/m$^3$.

In some embodiments, the flexible membrane (18) is circular, and has a diameter equal to the body. In some embodiments, the flexible membrane has same outer perimeter as the body (11).

In some embodiments, the flexible membrane (18) is circular, and has a diameter from 20 mm to 50 mm. In some embodiments, the flexible membrane (18) is circular, and has a diameter of 50 mm. In some embodiments, the flexible membrane (18) is circular, and has a diameter of 44 mm. In some embodiments, the flexible membrane (18) is circular, and has a diameter of 40 mm. In some embodiments, the flexible membrane (18) is circular, and has a diameter of 38 mm. In some embodiments, the flexible membrane (18) is circular, and has a diameter of 36 mm. In some embodiments, the flexible membrane (18) is circular, and has a diameter of 34 mm. In some embodiments, the flexible membrane (18) is circular, and has a diameter of 30 mm. In some embodiments, the flexible membrane (18) is circular, and has a diameter of 26 mm. In some embodiments, the flexible membrane (18) is circular, and has a diameter of 20 mm.

In some embodiments, the hole (19) has a diameter ranging from 0.4 mm to 1.2 mm. In some embodiments, the hole (19) has a diameter of 1 mm. In some embodiments, the hole (19) has a diameter of 0.8 mm. In some embodiments, the hole (19) has a diameter of 0.6 mm. In some embodiments, the hole (19) has a diameter of 0.4 mm. In some embodiments, the hole (19) is absent.

In some embodiments, the flexible membrane comprises PVC. In some embodiments the flexible membrane comprises Polyester, Polycarbonate. In some embodiments, the flexible membrane comprises a Phenoxy resin. In some embodiments, the flexible membrane comprises BoPET, such as, for example, the membrane sold under the trade name MYLAR®. In some embodiments, the flexible membrane comprises BoPET, such as, for example, the membrane sold under the trade name HOSTAPHAN®.

In some embodiments, the flexible membrane is the flexible membrane disclosed in U.S. Pat. No. 3,276,536.

In some embodiments, the microphone (17) is configured to detect fetal cardiac activity.

In some embodiments, the microphone (17) is a free air microphone. Alternatively, in some embodiments, the microphone (17) is a contact microphone. Alternatively, in some embodiments, the microphone (17) is a hybrid free air and contact microphone.

In some embodiments, the microphone (17) is configured to detect sub-ELF (extremely low frequency) signals. In some embodiments, the microphone is configured to have a flat response in the 5-150 Hz region.

In some embodiments, the microphone (17) is an electrostatic capacitor-based microphone. In some embodiments, the electrostatic capacitor-based microphone is a foil, or diaphragm type electrostatic capacitor-based microphone. In some embodiments, the electrostatic capacitor-based microphone is a back electret type electrostatic capacitor-based microphone. In some embodiments, the electrostatic capacitor-based microphone is a front electret type electrostatic capacitor-based microphone.

Referring to FIG. 2 to FIG. 4, an example of a garment according to some embodiments of the present invention is shown. In the embodiment shown, 4 acoustic sensors (2) are incorporated into a belt (1), wherein the belt, when worn, positions the acoustic sensors on the abdomen of the pregnant mother, such that the acoustic sensors contact the skin of the abdomen of the pregnant mother, and the acoustic sensors are positioned in a circumferential arrangement around the uterus. In the embodiments shown, the belt also contains additional sensors (4) and a transmitter (3).

In some embodiments, the additional sensors are ECG sensors.

Figure 29:
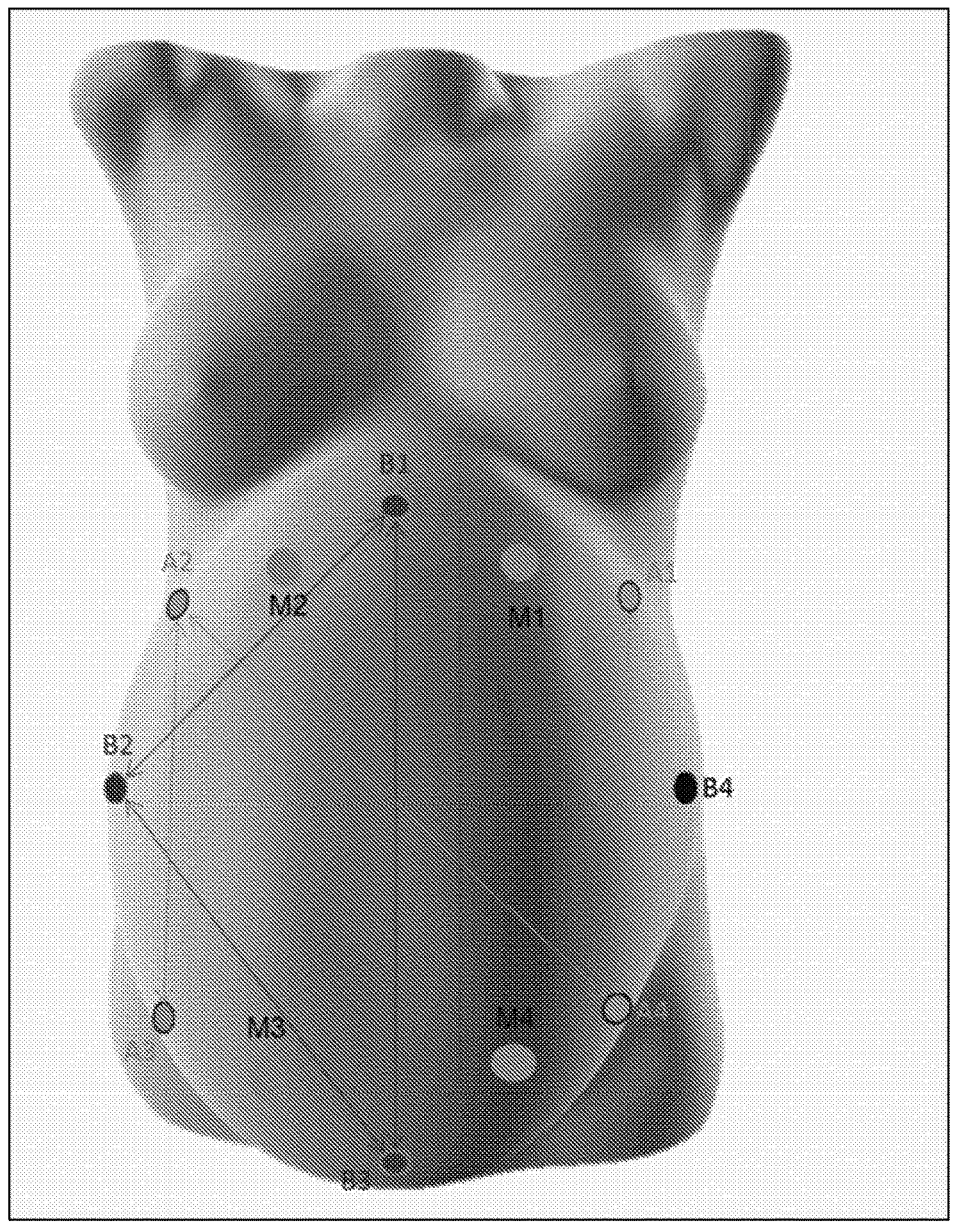
FIG. 29 shows the positions of the at least one ECG sensor (positions A1, A2, A3, A4, B1, B2, B3, B4) and the at least one acoustic sensor (positions M1, M2, M3 M4) on the abdomen of the pregnant human subject.

For example, as shown in FIG. 29, the exemplary inventive system of the present invention utilizes a set of four acoustic sensors (M1-M4) at respective exemplary positions. In some embodiments, the positioning of acoustic sensors can varies based, at least in part, on, for example, shape of mother's stomach, the stage of the pregnancy, physiological characteristics of the pregnant human subject and/or fetus(es), previous acoustic and/or other types of cardio recordings (e.g., Electrocardiogram (ECG) signal recordings and analysis, etc.), and other similarly suitable data.

Figure 27:
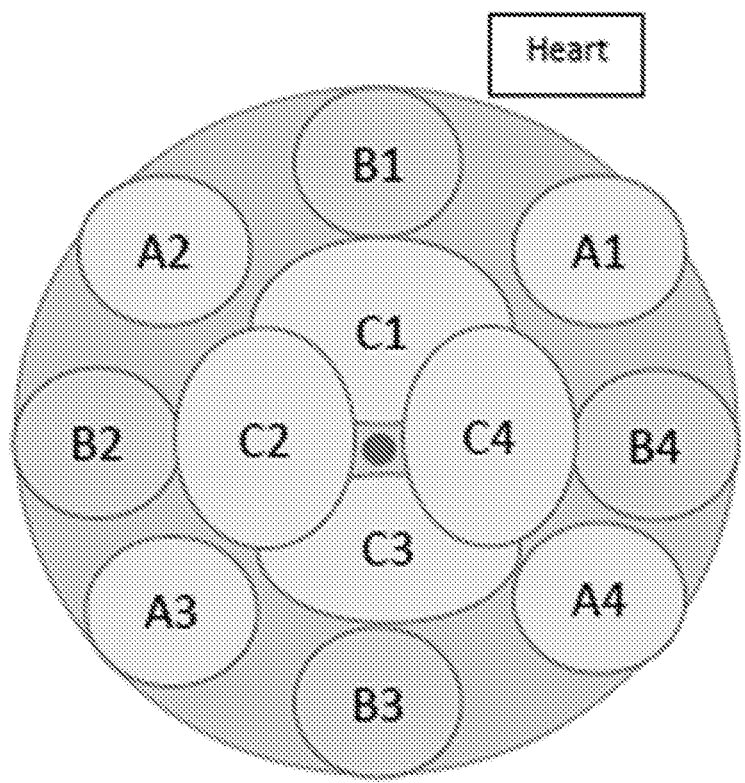
FIG. 27 shows the positions of the acoustic sensor (positions A1, A2, A3, A4, B1, B2, B3, B4, C1, C2, C3, C4) on the abdomen of the pregnant human subject according to some embodiments of the present invention.

An alternate positioning of the acoustic sensors is shown in FIG. 27.

In some embodiments, the acoustic sensors of the present invention record the internal sound produced inside the pregnant human subject with added noise from the environment. As detailed below, from these recordings the heartbeat sound of the fetus(es) and/or the pregnant human subject are extracted and the heart rate of each subject is calculated.

Figure 28:
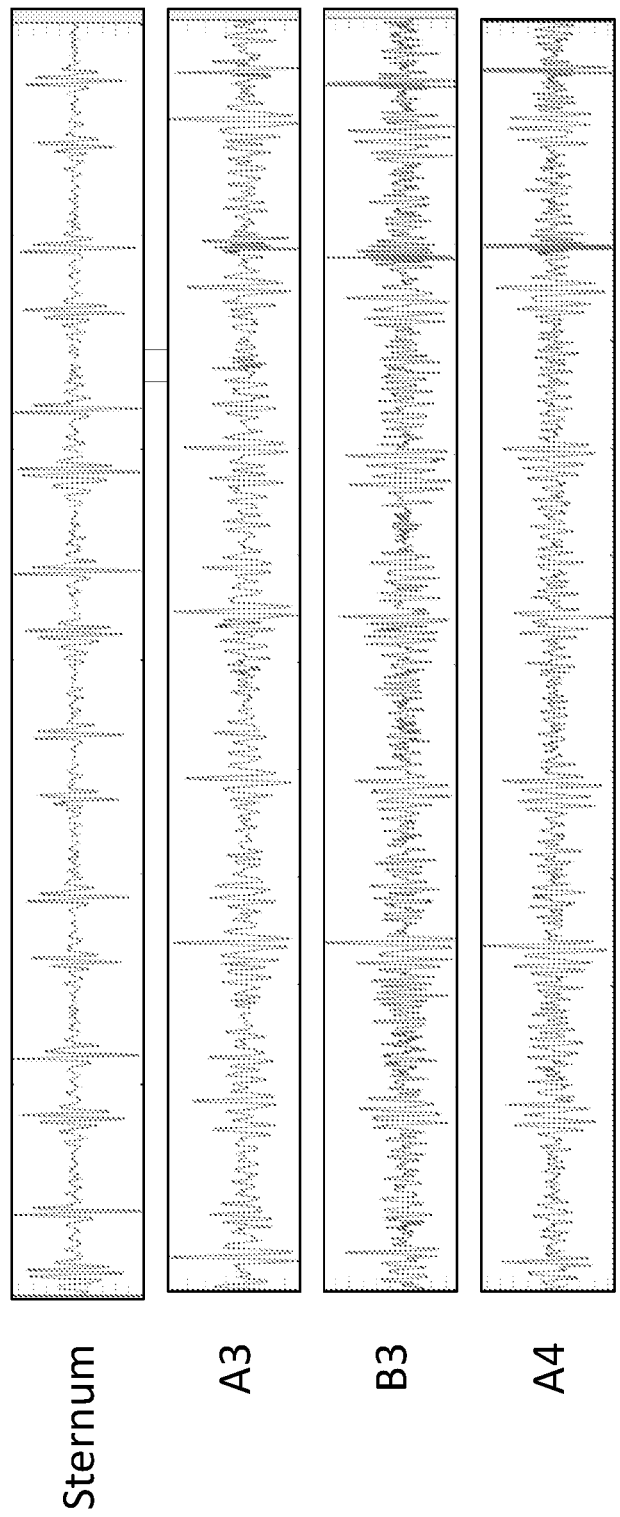
FIG. 28 shows maternal acoustic signals data received using an acoustic sensor according to some embodiments of the present invention.

In some embodiments, the level of detection by each acoustic sensor is independent of the other acoustic sensors (e.g, in FIG. 29, on other three acoustic sensors). Referring to FIG. 29, in some embodiments, it is determined that, typically, the fetal PCG signals are detected by the acoustic sensors in locations M3 and/or M4, while the maternal PCG signals are detected by the acoustic sensors in locations M1 and/or M2. In some embodiments, the maternal PCG signals can be detected by all four sensors (M1-M4) and have to be cleaned in order to detect the fetal heartbeats. In some embodiments, as detailed below, the cleaning process is performed using at least one Independent component analysis (ICA) algorithm of the present invention. For instance, in some embodiments, the inventive system of the present invention assumes that the interfering noises are audio sources which are not the fetal origin that thus are statistically independent from the fetal heart sounds. An example of maternal acoustic signals detected using an acoustic sensor according to some embodiments of the present invention is shown in FIG. 28.

ECG Signals Data Processing According to Some Embodiments of the Present Invention In some embodiments, ECG signals data is processed according to the methods described in U.S. patent application Ser. No. 14/921,489.

In some embodiments, the arrangement of the ECG sensors provides a system for recording, detecting and analyzing fetal cardiac electrical activity data regardless of sensor position, fetal orientation, fetal movement, or gestational age. In some embodiments, the ECG sensors are attached, or positioned, on the abdomen of the pregnant human subject in the configuration shown in FIG. 29. In some embodiments, the ECG sensors are divided into channels comprising a pair of ECG sensors, and cardiac electrical activity data is recorded simultaneously from the channels.

In some embodiments, the channels output the acquired signal data, corresponding to the recorded cardiac electrical activity data.

In some embodiments, at least one ECG sensor pair is used to obtain the acquired signal data. In some embodiments, the number of acquired signal data is referred to as "N". In some embodiments, the ability of the system to detect fetal cardiac electrical activity data is increased by increasing the value of N. For example, by way of a non-limiting illustration, in some embodiments, the channels are specified as follows:
1. B1-B3
2. B1-B2
3. B2-B3
4. A1-A4
5. A2-A3
6. A2-A4

In some embodiments, the signal data corresponding to fetal cardiac electrical activity data are extracted from the acquired signal data.

As used herein, in some embodiments, the term "N-ECG signals" refers to ECG signals data received from more than one, or N-ECG sensors.

In some embodiments the system of the present invention receives ECG signals from 1 electrode, comprising N-ECG patterns corresponding to N heart beats.

Figure 31:
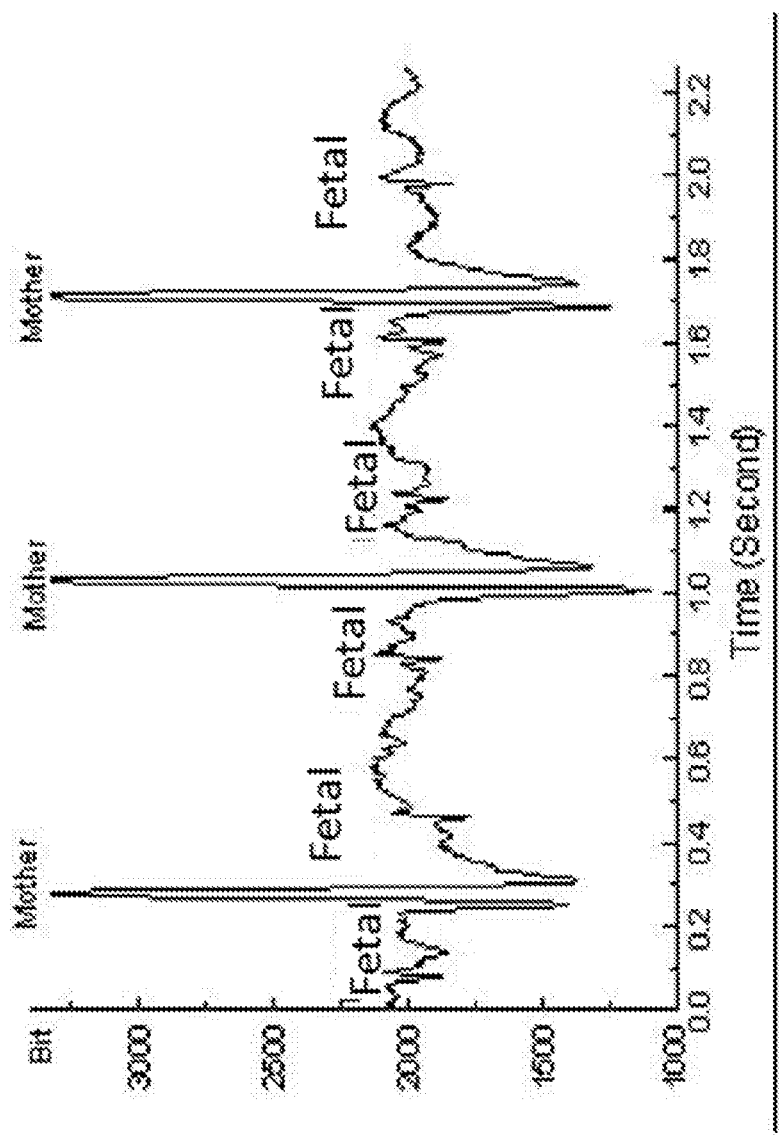
FIG. 31 shows an exemplary recording of cardiac electrical activity data according to some embodiments of the present invention.

Fetal cardiac activity elicits a semi-periodic electrical signal, typically from about 0.1 to 100 Hz. Frequently, signals corresponding to fetal cardiac activity are contaminated with other electrical signals, including maternal cardiac electrical activity. The signal elicited by maternal cardiac activity can be 10-fold greater than the fetal signal corresponding to fetal cardiac activity. See, for example, FIG. 31, showing an exemplary recording of cardiac electrical activity data, showing both maternal and fetal electrical activity combined.

In some embodiments, the fetal cardiac electrical activity data are extracted from the acquired signal data by a method comprising:
a) obtaining raw N-ECG signals data by recording electrical activity from the abdomen of a pregnant human subject carrying a fetus using at least one ECG sensor pair;
b) applying a set of linear and no-linear mathematical transformations to the raw N-ECG signals data, thereby obtaining transformed/corrected N-ECG signals data; and
c) finding features in the transformed/corrected N-ECG signals data that correlates to fetal or maternal cardiac electrical activity.

The term "transformations" as used herein refers to linear or non-linear mathematical transformations, which may include, inter alia, digital filtering, mathematical linear or non-linear decomposition, mathematical optimization.

Figure 30:
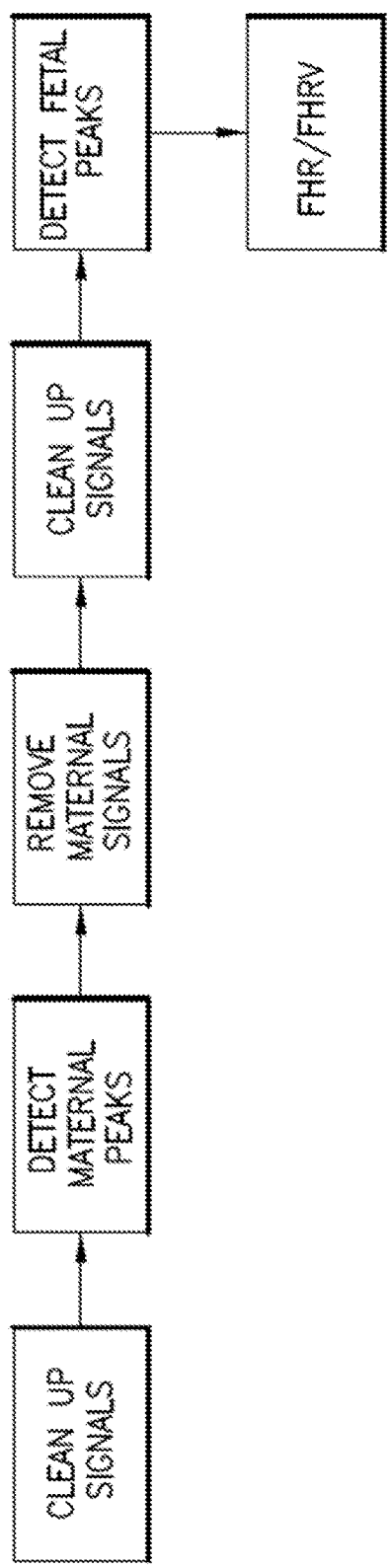
FIG. 30 shows a flow chart of an algorithm used to detect and analyze cardiac electrical activity data according to some embodiments of the present invention.

In some embodiments, the fetal cardiac electrical activity data are extracted from the acquired signal data using the algorithm shown in FIG. 30. Using the algorithm shown in FIG. 30, the recorded signal data are pre-processed to remove noise ("Clean up signals"), then the peaks of the maternal cardiac electrical activity are detected (Detect Maternal Peaks"), the maternal cardiac activity signal data is removed ("Remove Maternal Signals"), then the resulting data is processed to remove noise ("Clean up signals"), then the peaks of the fetal cardiac electrical activity are detected (Detect Fetal Peaks"), to detect fetal cardiac activity. The detected fetal activity data is then subsequently analyzed to calculate at least one of the parameters selected from the group consisting of: beat-to-beat fetal heart rate, fetal ECG, average fetal heart rate, and the variability of fetal heart rate.

In some embodiments, the present invention provides a computer-implemented method, comprising: receiving, by at least one computer processor executing specific programmable instructions configured for the method, raw Electrocardiogram (ECG) signals data from at least one pair of ECG sensors; wherein the at least one pair of ECG sensors are positioned in on an abdomen of a pregnant human subject; wherein the raw ECG signals data comprise data representative of a N number of raw ECG signals data (raw N-ECG signals data) which are being acquired in real-time from the at least one pair of ECG sensors; digital signal filtering, by the at least one computer processor, the raw N-ECG signals data to form filtered N-ECG signals data having filtered N-ECG signals; detecting, by the at least one computer processor, maternal heart peaks in each filtered ECG signal in the filtered N-ECG signals data; subtracting, by the at least one computer processor, from each of N-ECG signal of the filtered N-ECG signals data, maternal ECG signal, by utilizing at least one non-linear subtraction procedure to obtain corrected ECG signals data which comprise data representative of a N number of corrected ECG signals, wherein the at least one non-linear subtraction procedure comprises: iteratively performing: i) automatically dividing each ECG signal of N-ECG signals of the filtered N-ECG signals data into a plurality of ECG signal segments, 1) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) automatically modifying each of the second plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being, 2) setting a set of tentative values for a local template for each filtered N-ECG signal segment, 3) utilizing at least one optimization scheme to determine an adaptive template for each filtered N-ECG signal segment based on the local template being matched to the global template within a pre-determined similarity value; and iii) automatically eliminating the modified segments from each of the filtered N-ECG signals, by subtracting the adaptive template from the filtered N-ECG signal thereby generating each corrected ECG signal; extracting, by the at least one computer processor, raw fetal ECG signals data from the filtered N-ECG signals data based on the corrected ECG signals data, wherein the raw fetal ECG signals data comprises a N number of fetal ECG signals (raw N-ECG fetal signals data); processing, by the at least one computer processor, the raw N-ECG fetal signals data to improve a signal-to-noise ratio of the raw N-ECG fetal signals data to form filtered N-ECG fetal signals data; and detecting, by the at least one computer processor, fetal heart peaks in the filtered N-ECG fetal signals data; and calculating, by the at least one computer processor, based on detected fetal heart peaks, at least one of: i) fetal heart rate, ii) fetal heart curve, iii) beat-2-beat fetal heart rate, or iv) fetal heart rate variability; and outputting, by the at least one computer processor, a result of the calculating step.

Pre-Processing of the Acquired Signal Data

In some embodiments, the raw N-ECG signals data are preprocessed to remove noise, to generate filtered N-ECG signals data. In some embodiments, the preprocessing comprises applying a digital signaling filter selected from the group consisting of: a baseline wander filter, a power line frequency filter, and a high frequency filter.

In some embodiments, the baseline wander filter is intended to remove low frequency compartments of the recorded signals and enhance fast time varying parts of the signal.

In some embodiments, the baseline wander filter is a moving average filter with constant weights. In some embodiments, the moving average filter with a length of 501 milliseconds is used.

In some embodiments, the baseline wander filter is a moving median filter.

In some embodiments, the powerline frequency filter is intended to remove the power line interference that is picked up by the ECG sensor pairs. In some embodiments, the cut-off frequency of powerline frequency filter is set to the powerline frequency of the geographical area where the system of the present invention is used. For example, if the system is used in Europe, in some embodiments, the cut-off frequency is 49.5 to 50.5 Hz. If the system is used in the USA, in some embodiments, the cut-off frequency is 59.5 to 60.5 Hz.

In some embodiments, the cut-off frequency of the powerline frequency filter is ±10 Hz of the powerline frequency of the geographical area where the system of the present invention is used. In some embodiments, the cut-off frequency of the powerline frequency filter is ±5 Hz of the powerline frequency of the geographical area where the system of the present invention is used.

In some embodiments, a Butterworth type band-step filter with a cut-off frequency of 49.5 to 50.5 Hz whose order is 10th order, 5 sections is used. In some embodiments, a band-stop digital filter is used to attenuate the frequency components of the power line interference. In some embodiments, a digital adaptive filter is used to automatically determine the exact power line frequency before applying the band-stop filter.

In some embodiments, the high frequency filter is intended to remove very high frequency compartments from the acquired signals. In some embodiments, the high frequency filter is a digital low pass filter. In some embodiments, the digital low pass filter is used to attenuates the high frequency compartments of the acquired signals. In some embodiments, the digital low pass filter is a Chebyshev type I low pass filter.

In some embodiments, the cutoff frequency of the low pass filter is set to 70 cycles/second. In some embodiments, the baseline ripple is 0.12 decibels. In some embodiments, the order is 12th order, 6 sections.

In some embodiments, the high frequency filter is a smoothing filter. In some embodiments, the smoothing filter is used to attenuate the high frequency compartments of the raw N-ECG signals data.

In some embodiments, the high frequency filter is an edge preserving filter. In some embodiments, the edge preserving filter is used to remove high frequency noise from the raw N-ECG signals data while preserving valuable information regarding the fetal and maternal ECG signals contained within the raw N-ECG signals data. In some embodiments, the edge preserving filter is an adaptive mean filter. In some embodiments, the edge preserving filter is an adaptive median filter.

In some embodiments, an additional transformation is applied to the filtered N-ECG signals data. In some embodiments, a digital adaptive inverse-median filter is applied to the filtered N-ECG signals data to enhance the maternal ECG peaks.

Figure 32:
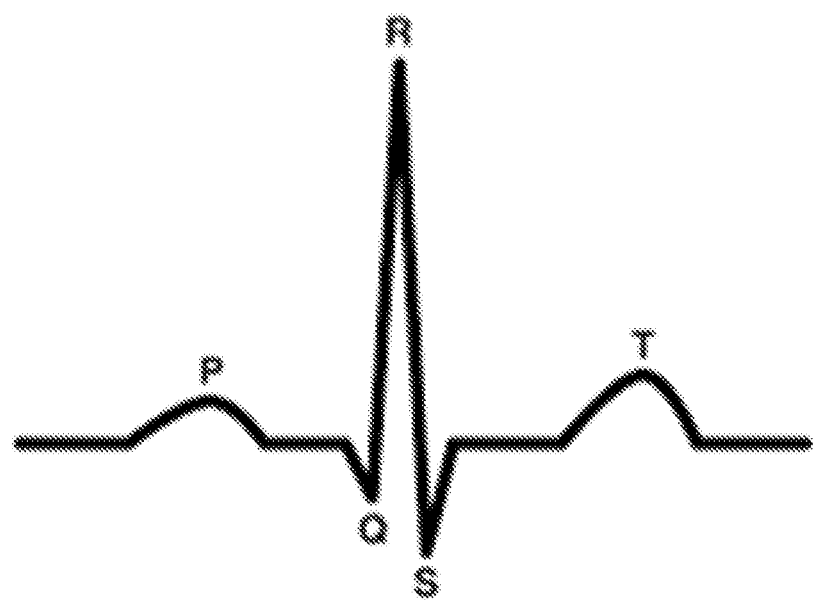
FIG. 32 shows a template maternal electrocardiogram according to some embodiments of the present invention.

The term "maternal ECG peaks" as used herein refers any of the P, Q, R, S or T waves of the electrical activity during a cardiac contraction cycle. FIG. 32 shows a depiction of the electrical activity during a cardiac contraction cycle.

In some embodiments, the additional transformation comprises applying an adaptive median filter to the N filtered N-ECG signals data, and subtracting the result filtered N-ECG signals data.

In some embodiments, the length of the adaptive median filter is selected to be constant. In some embodiments, the length is set to 100 samples.

In some embodiments, the length of the adaptive median filter is adapted depending on the local characteristics of the maternal ECG peaks.

As used herein, the term "local" refers to the signal recorded from a sensor positioned in at a particular location on the abdomen of the pregnant mother.

In some embodiments, the local characteristics are the duration of the QRS segment of the maternal electrical activity during a cardiac contraction cycle.

In some embodiments, the local characteristics are the duration of the ST segment of the maternal electrical activity during a cardiac contraction cycle.

In some embodiments, the local characteristics are the duration of the PR segment of the maternal electrical activity during a cardiac contraction cycle.

In some embodiments, the additional transformation comprises a decomposition to filtered N-ECG signals data to improve the signal to noise ratio. In some embodiments, the decomposition is a singular value decomposition (SVD). In some embodiments, the decomposition is principle component analysis (PCA). In some embodiments, the decomposition is independent component analysis (ICA). In some embodiments, the decomposition is wavelet decomposition (CWT).

In some embodiments, an additional high pass filter is applied to the decomposed filtered N-ECG signals data. In some embodiments, the high pass filter is $5^{th}$ order at 1 Hz. In some embodiments, the decomposed N filtered signal data is examined by preliminary and simple peak detector. In some embodiments, the relative energy of the peaks is calculated (relative to the overall energy of the signal). In some embodiments, the decomposed filtered N-ECG signals data is given a quality score depending on this measure, decomposed filtered N-ECG signals data with a quality score of less than a threshold are excluded and the signals are examined for missing data and NaNs (characters that are non-numerical).

In some embodiments, the quality score is assigned by calculating the relation (energy of peaks)/(Total energy of the filtered N-ECG signal). In some embodiments, the energy of the temporary peaks is calculated by calculating the root mean square of the detected peaks. In some embodiments, the energy of the signal is calculated by calculating the root mean square of the filtered N-ECG signals.

In some embodiments, the threshold is any value from 0.3 to 0.9. In some embodiments, the threshold is 0.8.

Detection of the Portion of the Acquired Signals Corresponding to Maternal Cardiac Activity from the Filtered N-ECG Signals Data and Elimination of the Signals Corresponding to Maternal Cardiac Activity from the Filtered N-ECG Signals Data In some embodiments, maternal heart peaks in each filtered N-ECG signal in the filtered N-ECG signals data are detected and subtracted from each of N-ECG signal of the filtered N-ECG signals data, by utilizing at least one non-linear subtraction procedure to obtain corrected N-ECG signals data which comprise data representative of a N number of corrected ECG signals, wherein the at least one non-linear subtraction procedure comprises: iteratively performing: i) automatically dividing each ECG signal of N-ECG signals of the filtered N-ECG signals data into a plurality of ECG signal segments, 1) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) automatically modifying each of the second plurality of filtered N-ECG signal segments to form a plurality of modified filtered N-ECG signal segments, wherein the modifying is performed using at least one inverse optimization scheme based on a set of parameters, wherein values of the set of parameters is determined based on: iteratively performing: 1) defining a global template based on a standard heartbeat profile of an adult human being, 2) setting a set of tentative values for a local template for each filtered N-ECG signal segment, 3) utilizing at least one optimization scheme to determine an adaptive template for each filtered N-ECG signal segment based on the local template being matched to the global template within a pre-determined similarity value; and iii) automatically eliminating the modified segments from each of the filtered N-ECG signals, by subtracting the adaptive template from the filtered N-ECG signal thereby generating each corrected ECG signal.

Figure 35:
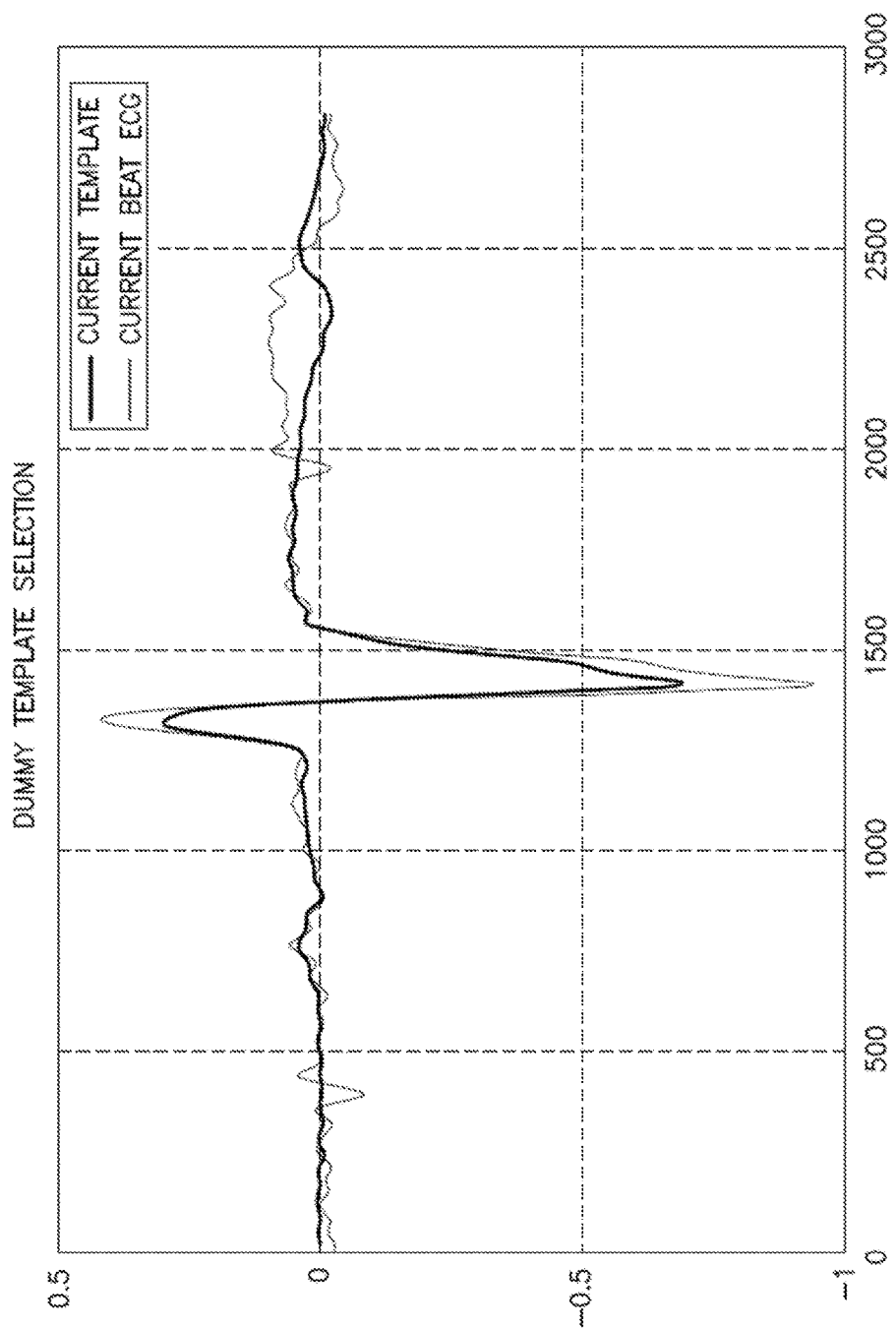
FIG. 35 shows an overlay of a template maternal electrocardiogram over a single maternal heart beat according to some embodiments of the present invention.
Figure 36:
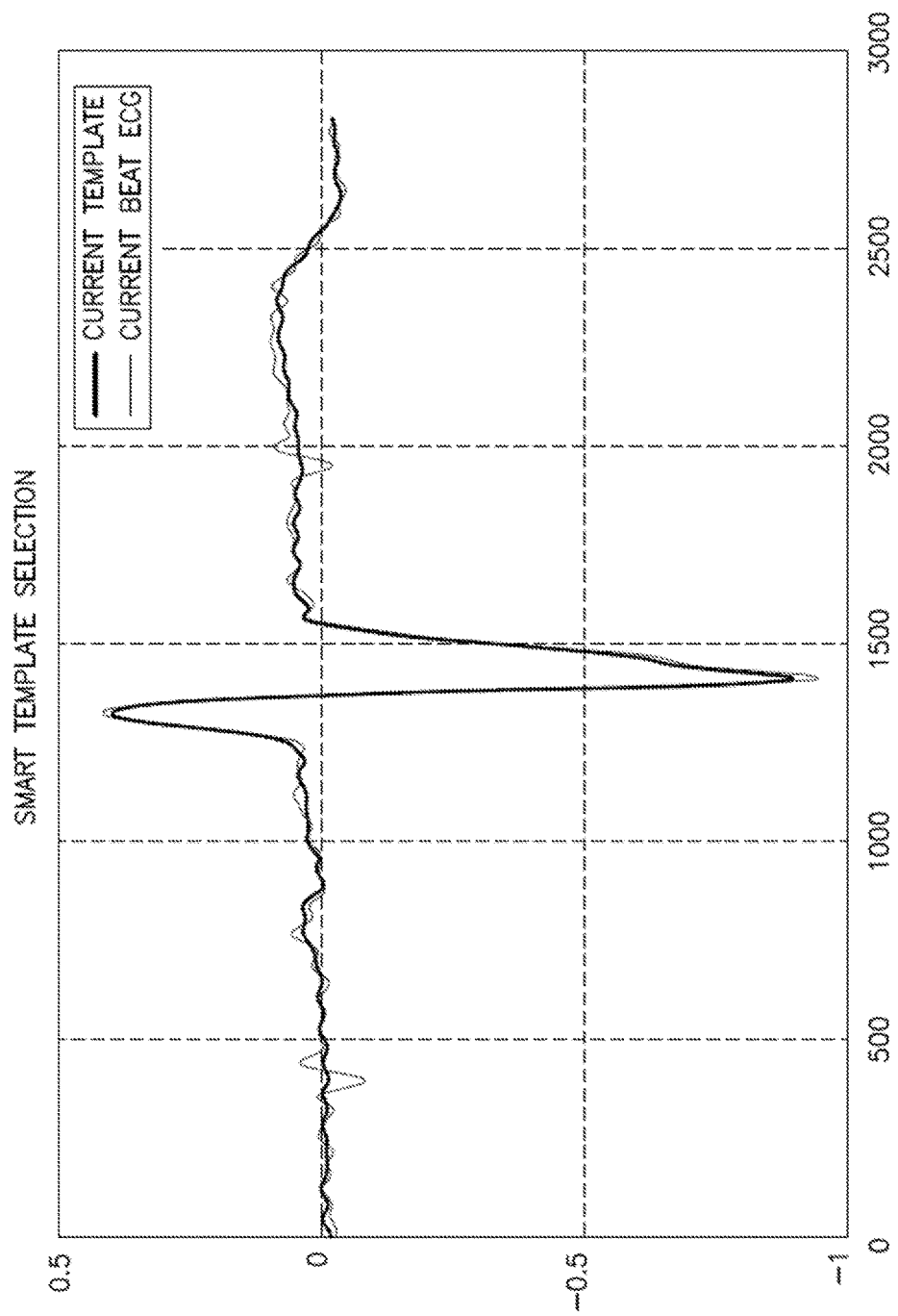
FIG. 36 shows an overlay of a template maternal electrocardiogram over a single maternal heart beat according to some embodiments of the present invention.

Examples of adaptive templates according to some embodiments of the present invention are shown in FIGS. 32, 35 and 36.

In some embodiments, detecting of the maternal heart peaks in each filtered ECG signal in the filtered N-ECG signals data is performed based at least on: i) dividing each filtered ECG signal into a first plurality of ECG signal segments; ii) normalizing a filtered ECG signal in each ECG signal segment; iii) calculating a first derivative of the filtered ECG signal in each ECG signal segment; iv) finding local maternal heart peaks in each ECG signal segment based on determining a zero-crossing of the first derivative; and v) excluding the local maternal heart peaks having at least one of: 1) an absolute value which is less than a pre-determined local peak absolute threshold value; or 2) a distance between the local peaks is less than a pre-determined local peak distance threshold value.

In some embodiments, the pre-determined similarity value is based on an Euclidian distance, wherein the set of parameters is a local minima solution to a non-linear least squares problem solved by at least one of: 1) minimizing a cost function taken as the Euclidian distance; 2) utilizing a Gauss-Newton algorithm; 3) utilizing a Steepest-Descent (Gradient-Descent) algorithm; or 4) utilizing a Levenberg-Marquardt algorithm.

In some embodiments, the length of each segment is set at 10 seconds.

In some embodiments, the length of each segment is selected automatically depending on the length of the recording.

In some embodiments, the signal data in each segment is normalized by the absolute maximum value of the signal data. In some embodiments, the signal data in each segment is normalized by the absolute non-zero minimum value of the signal data.

In some embodiments, a first order forward derivative is used. In some embodiments, a first order central derivative is used.

In some embodiments, the threshold is selected to be a constant value of 0.3.

In some embodiments, the threshold is selected depending on the local characteristics of the signal data. In some embodiments, the local characteristic of the signal is the median value of the signal data or any multiplication of this value. In some embodiments, the local characteristic of the signal is the mean value of the signal data or any multiplication of this value.

In some embodiments, the threshold on the distance is selected to be 100 samples.

In some embodiments, the local characteristics of the signal can be the maximum predicted RR internal or any multiple of this value.

In some embodiments, a "peaks array" is generated from the filtered N-ECG signals data. In some embodiments, the peak array comprises the number of detected peaks for each of the segments of the filtered N-ECG signals data.

In some embodiments, clustering is performed on the peaks array. In some embodiments, k-means clustering is used to group the peaks into a number of clusters. In some embodiments, k-medoids clustering is used to group the peaks into a number of clusters.

In some embodiments, the number of clusters for the clustering is set to be three. In some embodiments, the number of clusters for the clustering is selected automatically depending on the characteristics of the processed N filtered signal data.

In some embodiments, the clustering is used to exclude outliers. In some embodiments, outliers are peaks that have anomalous characteristics.

In some embodiments, the characteristic is the distance between a peak and its neighboring peaks. In some embodiments, the characteristic is the amplitude of the peak.

In some embodiments, a new peak array is constructed after the exclusion of the anomalous peaks.

In some embodiments, the new peak array is further analyzed and the peaks are scored depending on the signal to noise ratio of the filtered N-ECG signals data.

In some embodiments, the signal to noise ratio score is calculated by calculating the relative energy of the QRS complexes from the overall energy of the processed N filtered signal data.

In some embodiments, the detected peaks for each of the filtered N-ECG signals data are fused for a more robust detection. In some embodiments, the fusion of the detected peaks is done using the scores given for each of the peaks of the filtered N-ECG signals data.

In some embodiments, a global array of peaks is defined using the fused peaks.

In some embodiments, the peaks of each of the filtered N-ECG signals data is redetected and the positions are refined using the global peaks array. In some embodiments, the global peak array is constructed based on the best lead with corrections made using the peaks from the other leads and the global peaks array is examined using physiological measures, such as, for example, RR intervals, HR, HRV).

In some embodiments, after the peaks have been defined, the filtered N-ECG signals data is further transformed to eliminate the signals corresponding to maternal cardiac activity. In some embodiments, the transformations/corrections include applying non-linear subtraction to the filtered N-ECG signals data. In some embodiments, the remaining data comprises signal data corresponding to fetal cardiac activity and noise.

In some embodiments of the invention, the non-linear subtraction procedure is applied separately for each one of the processed N filtered signal data. In some embodiments, the non-linear subtraction procedure is applied to all of the processed N filtered signal data in series, in any order. In some embodiments, the non-linear subtraction procedure is applied to all of the processed N filtered signal data simultaneously.

In some embodiments, the non-linear subtraction comprises: dividing the processed N filtered signal data into a large number of segments; modifying each of the segments, separately or jointly, using an inverse optimization scheme; and eliminating the modified segments from the original processed N filtered signal data, thereby obtaining N raw fetal signal data.

The term 'segmentation', as used herein, refers to the division of the processed N filtered signal data into any given number of segments.

In some embodiments, the number of segments is set to be a function of the number of the detected maternal peaks. In some embodiments, the function is the identity function so that the number of segments equals the number of the detected maternal peaks, in which case, each segment is a full heartbeat.

In some embodiments, a beat interval is defined. The term 'beat interval' used hereinafter refers the time interval of a single maternal heart beat.

In some embodiments, the beat interval is taken to be constant and is defined as 500 milliseconds before the R-peak position and 500 milliseconds after the R-peak position.

In some embodiments, the beat interval is detected automatically by detecting the beat onset and beat offset of each beat. Thus, the beat interval depends on the local heart rate value and a more accurate segmentation of the ECG signal is achieved.

In some embodiments, the beat interval onset is defined as the onset (i.e. starting point in time) of the P-wave.

In some embodiments, the beat interval offset is defined as the offset (i.e. end point in time) of the T wave.

In some embodiments, the beat interval onset for the current beat is defined as half the way, in time, between the previous beat and the current beat.

In some embodiments, the beat interval offset for the current beat is defined as half the way, in time, between the current beat and the next beat.

In some embodiments, a second segmentation step is performed on the result of the previous segmentation. The product of this segmenting step is referred to as 'in-beat segments'.

In some embodiments, the number of in-beat segments is selected to be any integer number between one and the number of time samples in the current beat. By way of non-limiting example, the number of in-beat segment can be three.

In some embodiments, an automatic procedure is performed to detect the optimal number of in-beat segments. In some embodiments, the automatic procedure comprises using a Divide and Conquer algorithm, wherein each segment is divided into two equal sub-segments. If the energy content of a sub-segment exceeds a pre-defined relative threshold, the sub-segment itself is divided into two sub-segments and so on recursively. The stop criterion can be reaching a minimum length of sub-segment, reaching a maximum number of segments or dividing into sub-segments such that all of them meet the energy threshold criterion.

In certain embodiments, the entropy measure is used to divide the segment into sub-segments. In this case, the entropy of each segment is minimized.

In some embodiments, the result of the in-beat segmentation is the following seven segments:
1. The isoelectric line from the beat onset to the onset of the P wave;
2. The P wave;
3. The isoelectric line from offset of the P wave to the onset of the QRS complex;
4. The QRS complex;
5. The isoelectric line from the offset of the QRS complex to the onset of the T wave;
6. The T wave; and
7. The isoelectric line from the offset of the T wave to the beat offset.

In some embodiments, the majority of the energy of the filtered N-ECG signals data is in the QRS complex. Thus, in some embodiments, the in-beat segments a the following three in-beat segments:
1. From the beat onset to the onset of the QRS complex;
2. The QRS complex; and
3. From the offset of the QRS complex to the beat offset.

In some embodiments, the onset and offset of the QRS complex, for each of the beats in the ECG signal, are automatically detected using a dedicated method comprising: applying a digital band pass filter to the filtered N-ECG signals data; calculating the curve length transform of the filtered N-ECG signals data; selecting the values of the data that are higher than a threshold; calculating the first derivative of the transformed data; finding the positive transitions and negative transitions in the derivative data; finding pairs of the positive-and-negative transition such that the distance between them, in time samples, is higher than a pre-selected threshold; setting the onset of the QRS complex as the position, in time, of the positive transition from the selected pair; and setting the offset of the QRS complex as the position in time of the negative transition from the selected pair.

In some embodiments, the cutoff frequencies of the band pass filter are set to be 5 and 20 cycles/sec for the lower and upper frequencies respectively.

In some embodiments, the threshold is set to be a constant value of 0.3. In some embodiments, the threshold value is calculated automatically depending of the local characteristics of the data after the curve length transform. In some embodiments, the local characteristic of the data is the mean value of the transformed data.

In some embodiments, the segmentation also comprises an additional complementary transformation that comprises changing the sample rate of the signal by an integer value. In some embodiments, the additional complementary transformation reduces the variability of the resulting raw N-ECG fetal signals data caused by the fine positions of the onsets and offsets of the selected segments.

In some embodiments the sample rate is decreased by a factor of 4 to decrease the calculation time. Alternatively, in certain embodiments, the sample rate is increased by a factor of 4.

In some embodiments, increasing the sample rate is done using interpolation. In some embodiments, increasing the sample rate is done by zero padding the data and then applying a set of low pass FIR filters.

In some embodiments, changing the sample rate of the signals is done before the segmentation procedure. In some embodiments, changing the sample rate is done after the segmentation. In these embodiments, the selected onsets and offsets of the different segments are refined depending on the signals after changing the sample rate.

In some embodiments, the segmentation is updated depending on the convergence of the iterative methods in the next steps described hereinafter.

In some embodiments, the selected segments are modified using a nonlinear parametric transformation in which the values of a predefined set of parameters are changed according to some criterion.

In some embodiments, the values of a predefined set of parameters are determined and modified according to a method comprising: defining reference vectors as, for each filtered N-ECG signals data, the ECG signal and its segments (called 'measured potentials' hereinafter); and finding the values of the set of parameters that provide a good fit to results of the measured potentials.

A "good fit" occurs when the difference between the adapted template and the measured potentials is very small. In one embodiment, very small is defined to be $10^{-5}$ or smaller. In other embodiments, "very small" is defined as $10^{-6}$ or smaller or $10^{-4}$ or smaller or $10^{-7}$ or smaller or other exponents of 10 or other numbers.

In some embodiments, the difference between the adapted template and the measured potentials is the L2 norm of the element-by-element subtraction between the two vectors.

In some embodiments, the values of a predefined set of parameters also include parameters that change the amplitude of a time signal.

In some embodiments, an iterative scheme is used to determine the values of the set of the parameters, comprising: selecting starting conditions; assigning tentative values to the set of parameters; adapting the templates using the set of parameters; comparing the adapted templates to the measured potentials; checking if a stop criterion is reached; updating the values of the set of parameters if none of the stop criteria are reached, and repeating steps (c), (d), (e) and (f). In some embodiments, if a stop criterion is reached, the iterative procedure is terminated and the current set of parameters is deemed the optimal solution of the optimization problem.

In some embodiments, the starting conditions are set to be the ECG templates. In some embodiments, two templates are defined: The first is a global template that is defined for every ECG beat (see, for example, FIG. 35), wherein the template is calculated as a weighted average of M beats. In some embodiments, M is an integer number between 2 and the total number of beats in the ECG signal. In some embodiments, the weights used in the weighted average are equal yielding a normal averaging. In some embodiments, the M beats fulfill the condition that the correlation coefficient between each of the beats should be higher than a threshold. In certain embodiments, the threshold is set to be 0.98. In some embodiments, before the averaging, the beats are shifted and fine aligned using the exact position of the R-wave, the QRS onset and the QRS offset. In some embodiments, the alignment procedure is done using the cross correlation function. In Some embodiments, the M beats fulfill the condition that relation between the energy of the template, defined as an average of these beats, and the energy of the current ECG beat is bounded close to 1. However, in some embodiments, the relation between the energy of the template and the energy of the current ECG beat is higher than 1 by a small value or lower than 1 by a small value.

The second is a local template that is defined for each of the sub-segments in the current beat (see, for example, FIG. 36). In some embodiments, the template is calculated as the average of the sub-segments in the M-selected peaks. In some embodiments, the beats are selected to fulfill the conditions that the local heart rate is similar to the local heart rate for the current beat. By means of a non-limiting example, the heart rate values are close by a factor of 1.5.

In some embodiments, the tentative values are set to random numbers. In some embodiments, the tentative values are set to be constant numbers; by means of a non-limiting example, they are set to be 1.

In some embodiments, the tentative values are saved between different executions of the algorithm and used if available.

In some embodiments, the different templates are adapted separately depending on the appropriate parameters that are assigned to the templates. In some embodiments, the templates are scaled by multiplying the templates vectors with the appropriate set of parameters. In some embodiments, the templates are shifted in time using the appropriate set of parameters.

In some embodiments, the Euclidian distance is used to compare the two sets of vectors; the adapted templates and the measured potentials from the processed N filtered signal data. In some embodiments, the cost function is defined as the error energy function.

In some embodiments, the city-block measure is used to compare the adapted templates to the measured potentials.

In some embodiments, the cross correlation function is used to compare the adapted templates and measured potentials. In some embodiments, a "good fit" is a correlation of 0.95 or greater.

In some embodiments, a maximum number of iterations is used as a stop criterion.

In some embodiments, in the case of using the Euclidian distance as a similarity measure, the value of the error energy function at a specific iteration is used as a stop criterion. In some embodiments, if the error energy becomes lower than a threshold, the stop criterion is reached.

In certain embodiments, the threshold is set to be constant. By means of a non-limiting example, it is set to be $10^{-5}$.

In some embodiments, the threshold is calculated depending on the characteristics of the iterative procedure. For example, in some embodiments, the characteristics of the iterative procedure is the maximum number of allowed iterations; in other embodiments, the characteristics of the iterative procedure is the used cost function, for example the Euclidian distance function; and still other embodiments, the characteristics of the iterative procedure is the number of time samples in the templates.

In some embodiments, an improvement measure is used as a stop criterion.

In some embodiments, the change in the set of parameters is used as an improvement measure. In some embodiments, if the values of the set of parameters does not change, or change slightly, the stop criterion is fulfilled.

In some embodiments, the change in the value of the cost function, e.g. the error energy function, is used as an improvement measure.

In some embodiments, if a stop criterion is reached, an optimization scheme is applied to update the values of the set of parameters.

In some embodiments, when using the Euclidian distance as a similarity measure, the optimization problem becomes a non-linear least squares problem. In some embodiments, the solution of this problem gives the optimal set of parameters that minimizes the cost function taken as the Euclidian distance.

In some embodiments, Gauss-Newton algorithm is used to solve the non-linear least squares problem.

In some embodiments, the Steepest-Descent (Gradient-Descent) method is used to solve the non-linear least squares problem.

In some embodiments, the Levenberg-Marquardt algorithm is used to solve the non-linear least squares problem. In these embodiments, the problem becomes a damped least squares problem. Levenberg-Marquardt algorithm is a method, which interpolates between the Gradient-Descent and Gauss-Newton algorithm taking advantage of both methods to increase the convergence accuracy and decrease the convergence time.

In some embodiments, Gradient-Descent, Gauss-Newton algorithm and Levenberg-Marquardt algorithm, are iterative methods that are repeated a number of times, potentially, bringing the Euclidian distance (the error energy function) to a local minima.

In some embodiments, updating the set of parameters is performed using the relation:

$$P_{k+1} = P_k - [\mathcal{J}_k^T \mathcal{J}_k + \lambda_i \cdot \text{diag}(\mathcal{J}_k^T \mathcal{J}_k)]^{-1} * \mathcal{J}_k^T [\phi_c(P_k) - \phi m]$$

Where $P_k$ is the set of parameters at the $k^{th}$ iteration; and $\phi_c(P_k)$ is the adapted version of the templates for the $P_k$ parameters; and $\lambda_i$ is the damping parameter in the Levenberg-Marquardt algorithm; and $\phi_m$ is the measured potentials (measured ECG signals); and $\mathcal{J}_k$ is the Jacobian matrix calculated for the set of parameters $P_k$ by altering the values of the parameters; and $\text{diag}(\mathcal{J}_k^T \mathcal{J}_k)$ is the diagonal of the approximated Hessian matrix.

In some embodiments, eliminating the modified segments from the N raw signal data is achieved by subtracting the adapted templates from the measured potentials. In some embodiments, the subtraction results in N raw fetal signal data. In some embodiments, the N raw fetal signal data comprises noise and fetal cardiac electrical activity data.

Figure 33:
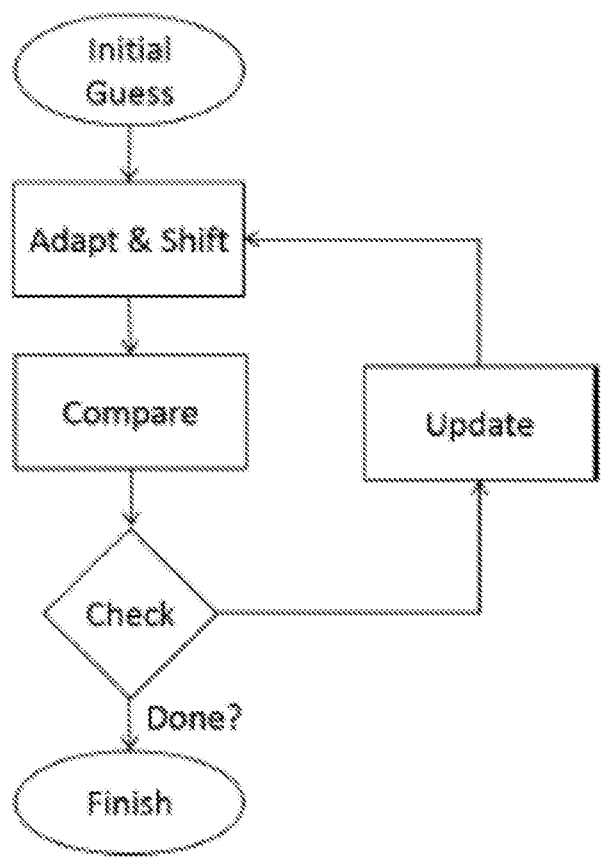
FIG. 33 shows a flow chart of an algorithm used to perform maternal cardiac activity elimination according to some embodiments of the present invention.

In some embodiments, maternal cardiac activity is eliminated using the algorithm shown in FIG. 33.

Figure 34:
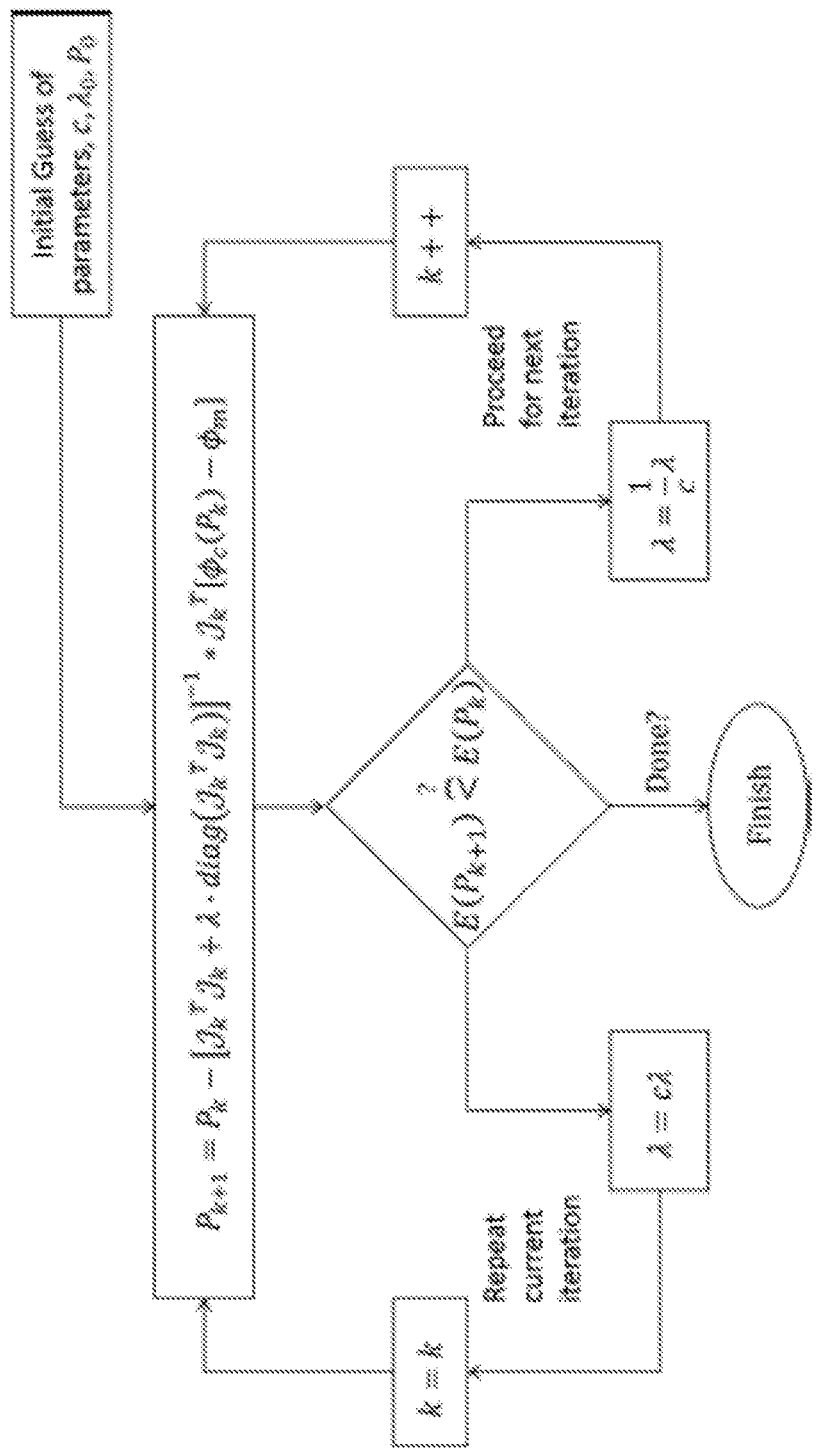
FIG. 34 shows a flow chart of an algorithm used to perform maternal cardiac activity elimination according to some embodiments of the present invention.

In some embodiments, maternal cardiac activity is eliminated using the algorithm shown in FIG. 34.

Figure 37:
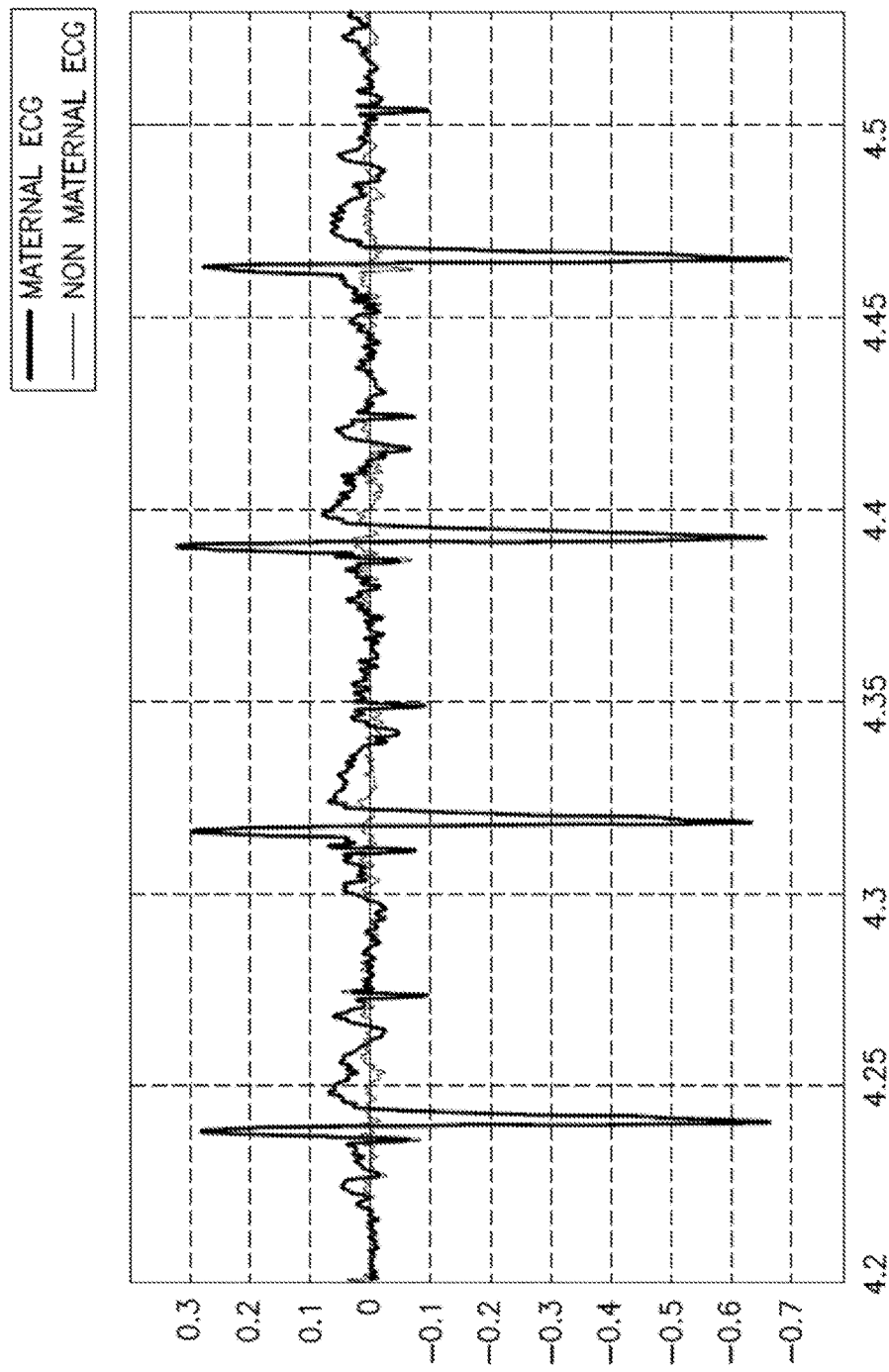
FIG. 37 shows the result of maternal ECG elimination of according to some embodiments of the present invention.

A representative result of maternal ECG elimination according to some embodiments of the present invention is shown in FIG. 37.

Extraction of the Fetal Cardiac Electrical Activity Data and Detecting Fetal Cardiac Electrical Activity Data In some embodiments, raw fetal ECG signals data is extracted and analyzed by utilizing a Blind-Source-Separation (BSS) algorithm on (1) the filtered N-ECG signals data and (2) the corrected N-ECG signals data, wherein the raw fetal ECG signals data comprises a N number of fetal ECG signals (N-ECG fetal signals); processing, by the at least one computer processor, the raw fetal ECG signals data to improve a signal-to-noise ratio by at least: i) applying a band-pass filter within a range of 15-65 Hz to break the plurality of raw N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered fetal ECG signals data, comprising a N number of filtered fetal ECG signals (filtered N-ECG fetal signals data); detecting, by the at least one computer processor, fetal heart peaks in the filtered N-ECG fetal signals data, by performing at least: i) dividing each filtered N-ECG fetal signal into a first plurality of fetal ECG signal segments; ii) normalizing a filtered fetal ECG signal in each fetal ECG signal segment; iii) calculating a first derivative of the filtered fetal ECG signal in each fetal ECG signal segment; and iv) finding local fetal heart peaks in each fetal ECG signal segment based on determining a zero-crossing of the first derivative; calculating, by the at least one computer processor, based on detected fetal heart peaks, at least one of: i) fetal heart rate, ii) fetal heart curve, iii) beat-2-beat fetal heart rate, or iv) fetal heart rate variability; and outputting, by the at least one computer processor, a result of the calculating step.

In some embodiments, the processing of the raw N-ECG fetal signals data to improve the signal-to-noise ratio comprises: i) applying a band-pass filter within a range of 15-65 Hz to break the plurality of N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered ECG fetal signals data, comprising a N number of filtered fetal ECG signals (filtered N-ECG fetal signals data).

In some embodiments, the processing of the raw N-ECG fetal signals data to improve the signal-to-noise ratio comprises: i) applying a band-pass filter within a range of 1-70 Hz to break the plurality of N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered ECG fetal signals data, comprising a N number of filtered fetal ECG signals (filtered N-ECG fetal signals data).

In some embodiments, the processing of the raw N-ECG fetal signals data to improve the signal-to-noise ratio comprises: i) applying a band-pass filter within a range of 5-70 Hz to break the plurality of N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered ECG fetal signals data, comprising a N number of filtered fetal ECG signals (filtered N-ECG fetal signals data).

In some embodiments, the processing of the raw N-ECG fetal signals data to improve the signal-to-noise ratio comprises: i) applying a band-pass filter within a range of 10-70 Hz to break the plurality of N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered ECG fetal signals data, comprising a N number of filtered fetal ECG signals (filtered N-ECG fetal signals data).

In some embodiments, the processing of the raw N-ECG fetal signals data to improve the signal-to-noise ratio comprises: i) applying a band-pass filter within a range of 1-65 Hz to break the plurality of N-ECG fetal signals in to a plurality of frequency channels, ii) scoring an ECG fetal signal per channel based on a peak-2-mean analysis to identify a plurality of fetal heartbeat channels, wherein each fetal heartbeat channel corresponds to a particular fetal ECG fetal signal; and iii) selecting the identified plurality of fetal heartbeat channels into filtered ECG fetal signals data, comprising a N number of filtered fetal ECG signals (filtered N-ECG fetal signals data).

In some embodiments, the processing of the raw N-ECG fetal signals data to improve the signal-to-noise ratio further comprises at least one of: 1) utilizing a Singular-Value-Decomposition (SVD) technique; or 2) utilizing a Wavelet-Denoising (WD) technique.

In some embodiments, all of the raw N-ECG signals data are used in the BSS procedure so that the BSS procedure is applied to 2N signals. In other embodiments, only part of the raw N-ECG signals data is used in the BSS procedure so that the BSS procedure is applied to between N+1 signals and less than 2N signals.

In some embodiments, Principal Component Analysis (PCA) is used as the BSS method. In some embodiments, Independent Component Analysis (ICA) is used as the BSS method.

In some embodiments, the results of the BSS procedure is further analyzed to improve the signal to noise ratio of the signals. In some embodiments, the further analysis includes a band-pass filter in the range of 15-65 cycle/second. In some embodiments, the further analysis includes applying Singular-Value-Decomposition (SVD). In some embodiments, the further analysis includes applying Wavelet-Denoising.

In some embodiments, the further analysis includes applying 'peak-2-mean' transformation, which in some versions is in a separate software module, that comprises:

a. using a moving window (win) to calculate the relation:

$$\frac{\max(\text{Signal[win]})}{\text{mean}(\text{Signal[win]})};$$

and b. calculating the 1st derivative of the result of step a; and
c. finding the zero crossing to find peaks taking the negative part of the derivative; and
d. finding the peaks in the previous result and cluster them based on the difference between them. Identify the best group as the group with the maximum score defined as: SCR=n/RMS where n is the number of peaks in each cluster and RMS is the energy of the derivative of the distances between the peaks; and
e. performing a prediction for the RR interval for the best group; and
f. if the prediction doesn't fit the real physiological model of the fetal RR intervals, the current signal is ignored and one then begins the process at the beginning (i.e. using a moving window to calculate the relation) with the next signal; and
g. if the prediction does fit the real physiological model of the fetal RR, calculate the auto correlation function of a windowed RMS of the signal. If the result has a narrow distribution, the current signal is ignored, and if the result does not have a narrow distribution, then proceed as follows:
h. applying AGC to the negative derivative signal; and
i. normalizing the result.

In certain embodiments, the above 'peak-2-mean transformation' is applied separately to each signal (i.e. each of the 2N signals or each of the between N+1 and less than 2N signals).

In some embodiments, fetal heart beat detection is performed. For example, in some embodiments, the N raw fetal signal data are subjected the fetal peak detection procedure before the further analysis and in other embodiments the results of the further analysis subjected to the fetal peak detection procedure.

In some embodiments, the analysis comprises: dividing the N filtered fetal signal data into segments; normalizing the signal data in each segment; calculating the first derivative of the normalized signal data; identifying the fetal ECG peaks within the normalized signal data by determining the zero-crossing of the first derivative; excluding peaks whose absolute value is less than a threshold pre-selected by the user; and excluding very close peaks where the distance between them is less than a threshold, thereby obtaining processed N filtered fetal signal data.

In some embodiments, the length of each segment is set at 10 seconds.

In some embodiments, the length of each segment is selected automatically depending on the length of the recording.

In some embodiments, the signal data in each segment is normalized by the absolute maximum value of the signal data. In some embodiments, the signal data in each segment is normalized by the absolute non-zero minimum value of the signal data.

In some embodiments, a first order forward derivative is used. In some embodiments, a first order central derivative is used.

In some embodiments, the threshold is selected to be a constant value of 0.3.

In some embodiments, the threshold is selected depending on the local characteristics of the signal data. In some embodiments, the local characteristic of the signal is the median value of the signal data or any multiplication of this value. In some embodiments, the local characteristic of the signal is the mean value of the signal data or any multiplication of this value.

In some embodiments, the threshold on the distance is selected to be 100 samples.

In some embodiments, the local characteristics of the signal can be the maximum predicted RR internal or any multiple of this value.

In some embodiments, a "peaks array" is generated from the filtered N-ECG fetal signals data. In some embodiments, the peak array comprises the number of detected peaks for each of the segments of the filtered N-ECG fetal signals data.

In some embodiments, clustering is performed on the peaks array. In some embodiments, k-means clustering is used to group the peaks into a number of clusters. In some embodiments, k-medoids clustering is used to group the peaks into a number of clusters.

In some embodiments, the number of clusters for the clustering is set to be three. In some embodiments, the number of clusters for the clustering is selected automatically depending on the characteristics of the filtered N-ECG fetal signals data.

In some embodiments, the clustering is used to exclude outliers. In some embodiments, outliers are peaks that have anomalous characteristics.

In some embodiments, the characteristic is the distance between a peak and its neighboring peaks. In some embodiments, the characteristic is the amplitude of the peak.

In some embodiments, a new peak array is constructed after the exclusion of the anomalous peaks.

In some embodiments, the new peak array is further analyzed and the peaks are scored depending on the signal to noise ratio of the filtered N-ECG fetal signals data.

In some embodiments, the signal to noise ratio score is calculated by calculating the relative energy of the QRS complexes from the overall energy of the filtered N-ECG fetal signals data.

In some embodiments, the detected peaks for each of the filtered N-ECG fetal signals data are fused for a more robust detection. In some embodiments, the fusion of the detected peaks is done using the scores given for each of the peaks of filtered N-ECG fetal signals data.

In some embodiments, a global array of peaks is defined using the fused peaks.

In some embodiments, the peaks of each of the filtered N-ECG fetal signals data is redetected and the positions are refined using the global peaks array. In some embodiments, the global peak array is constructed based on the best lead with corrections made using the peaks from the other leads and the global peaks array is examined using physiological measures, such as, for example, RR intervals, HR, HRV).

In some embodiments, the beat-to-beat fetal heart rate is extracted from the detected fetal peaks positions. In some embodiments, the fetal heart curve is also extracted from the detected fetal peak positions.

PCG Signals Data Processing According to Some Embodiments of the Present Invention In some embodiments, the present invention provides a system for detecting, recording and analyzing aucoustic data from a pregnant mother carrying a fetus to discern cardiac data of mother and/or fetus. In some embodiments, a plurality of acoustic sensors is used to record phonocardiogram (PCG) signals, representative of cardiac activity data. The phonocardiogram signals are recordings of all the sounds made by the heart during a cardiac cycle due to, typically, for example, vibrations created by closure of the heart valves. For instance, there can be at list two sound generating events: the first when the atrioventricular valves close at the beginning of systole (S1) and the second when the aortic valve and pulmonary valve close at the end of systole (S2).

In some embodiments, the exemplary inventive system of the present invention can utilize a plurality of acoustic sensors (e.g., 2, 3, 4, 5, 6, 7, 8, 9, 10, etc.) to be positioned on and/or near the abdomen of a pregnant woman. For example, in some embodiments, the acoustic sensors are directly attached. In some embodiments, the acoustic sensors are incorporated into an article, such as, for example, a belt, a patch, and the like, and the article is worn by, or placed on, the pregnant mother.

In some embodiments, the choice of acoustic sensors is readily determined by one of ordinary skill in the art. Factors influencing acoustic sensor choice include, but are not limited to, the sensitivity of the microphone component, the size of the acoustic sensor, the weight of the acoustic sensor, and the like. In some embodiments, the acoustic sensor is configured to compensate for the changes in sound propagation caused by the skin-air interface. Acoustic signals comprise sound waves or vibrations that propagate as a mechanical wave of pressure and displacement, through a medium such as air, water, or the body. Without intending to be limited to any particular theory, the behavior of sound propagation can be affected by the relationship between the density and pressure of the medium though which the sound wave propagates. Also, the behavior of sound propagation can be affected by the motion of the medium though which the sound wave propagates. Furthermore, the behavior of sound propagation can be affected by the viscosity of the medium though which the sound wave propagates.

For example, as shown in FIG. 29, the exemplary inventive system of the present invention utilizes a set of four acoustic sensors (M1-M4) at respective exemplary positions. In some embodiments, the positioning of acoustic sensors can varies based, at least in part, on, for example, shape of mother's stomach, the stage of the pregnancy, physiological characteristics of mother and/or fetus(es), previous acoustic and/or other types of cardio recordings (e.g., Electrocardiogram (ECG) signal recordings and analysis, etc.), and other similarly suitable data.

In some embodiments, the acoustic sensors of the present invention record the internal sound produced inside the woman with added noise from the environment. As detailed below, from these recordings the heartbeat sound of the fetus(es) and/or the mother are extracted and the heart rate of each subject is calculated.

In some embodiments, the level of detection by each acoustic sensor is independent of the other acoustic sensors (e.g, in FIG. 29, on other three acoustic sensors). Referring to FIG. 29, in some embodiments, it is determined that, typically, the fetus PCG signals are detected by the acoustic sensors in locations M3 and/or M4, while the maternal PCG signals are detected by the acoustic sensors in locations M1 and/or M2. In some embodiments, the maternal PCG signals can be detected by all four sensors (M1-M4) and have to be cleaned in order to detect the fetus(es) heartbeats. In some embodiments, as detailed below, the cleaning process is performed using at least one Independent component analysis (ICA) algorithm of the present invention. For instance, in some embodiments, the inventive system of the present invention assumes that the interfering noises are audio sources which are not the fetal origin that thus are statistically independent from the fetal heart sounds.

Figure 38:
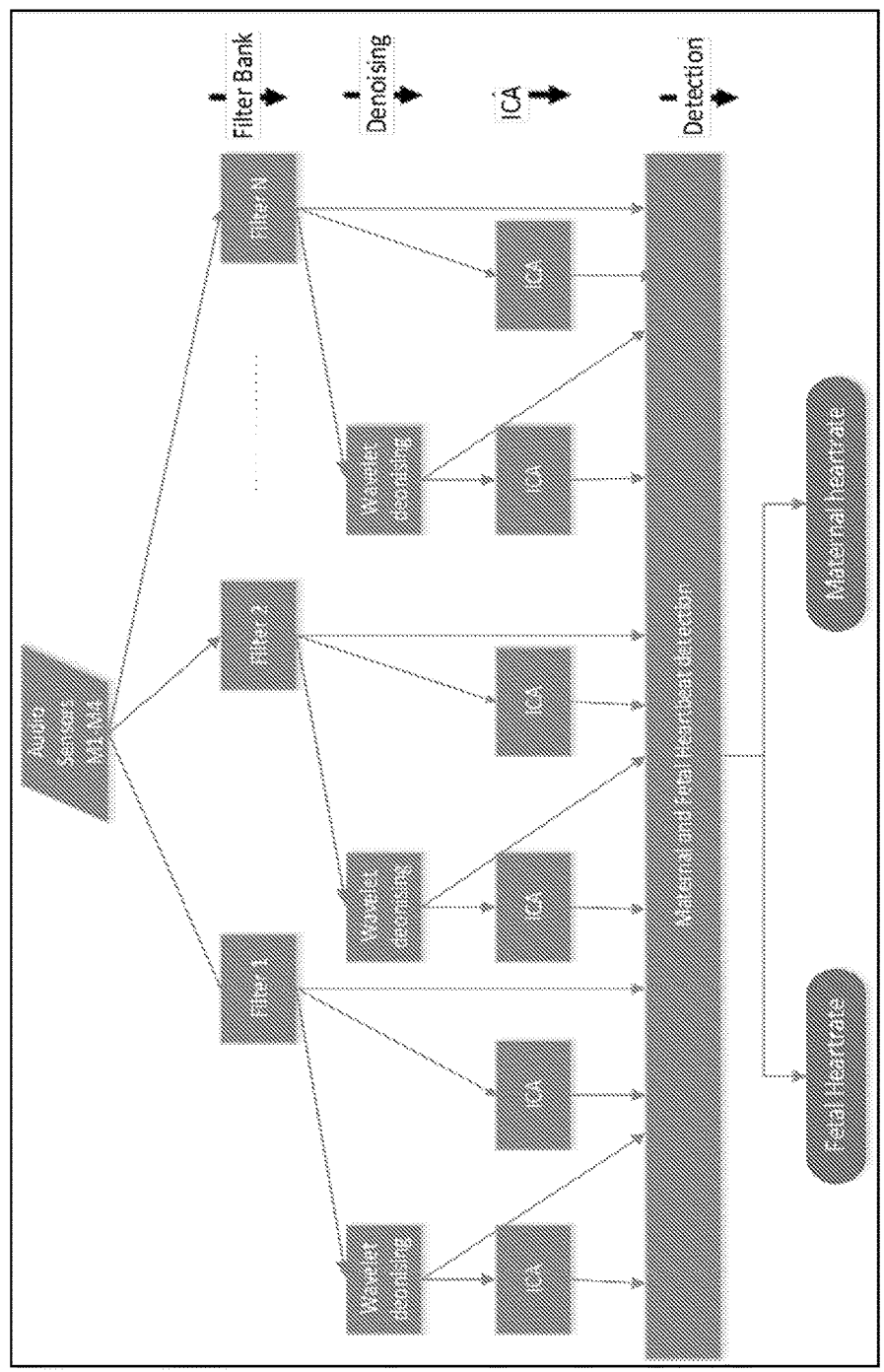
FIG. 38 shows a flow chart of an algorithm used to detect and analyze cardiac activity data according to some embodiments of the present invention.

An Example of an Illustrative Process Utilized to Estimate the Fetus(es) and/or Maternal Heartbeat Data in Accordance with the Present Invention FIG. 38 shows an exemplary process utilized, in some embodiments, by the exemplary inventive system of the present invention to estimate the fetus(es) and/or maternal heartbeat data (e.g., presence of heartbeats, heartbeat patterns, heartbeat frequency, ect.).

Referring to FIG. 38, the illustrative process contains at the following four stages.

Stage 1: Filter Bank

Referring to FIG. 38, the input is the signal data recorded by each acoustic sensor (M1-M4) shown in FIG. 29. In some embodiments, the recorded signal data from each of the four acoustic sensors is passed through, for example but not limited to, L number of bandpass filters, where each filter has a predetermine frequency range. In some embodiments, the exemplary six bandpass filters (L=6) can have the following six bandwidths:
10-45 Hz
20-50 Hz
25-65 Hz
40-80 Hz
55-95 Hz
20-80 Hz.

In some embodiments, there can be at least 3 bandpass filters. In some embodiments, there can be between 3-12 bandpass filters. In some embodiments, there can be between 5-10 bandpass filters. In some embodiments, there can be at least 5 bandpass filters. In some embodiments, there can be at least 7 bandpass filters.

In some embodiments, the bandwidth of a particular filter can be selected from a range of 10-100 Hz. In some embodiments, the bandwidth of a particular filter can be selected from a range of 20-100 Hz. In some embodiments, the bandwidth of a particular filter can be selected from a range of 30-100 Hz. In some embodiments, the bandwidth of a particular filter can be selected from a range of 40-100 Hz. In some embodiments, the bandwidth of a particular filter can be selected from a range of 50-100 Hz. In some embodiments, the bandwidth of a particular filter can be selected from a range of 60-100 Hz. In some embodiments, the bandwidth of a particular filter can be selected from a range of 70-100 Hz. In some embodiments, the bandwidth of a particular filter can be selected from a range of 80-100 Hz. In some embodiments, the bandwidth of a particular filter can be selected from a range of 90-100 Hz.

In some embodiments, a particular filter can have a frequency range of 5-110 Hz. In some embodiments, a particular filter can have a frequency range of 15-110 Hz. In some embodiments, a particular filter can have a frequency range of 25-110 Hz. In some embodiments, a particular filter can have a frequency range of 35-110 Hz. In some embodiments, a particular filter can have a frequency range of 45-110 Hz. In some embodiments, a particular filter can have a frequency range of 55-110 Hz. In some embodiments, a particular filter can have a frequency range of 5-105 Hz. In some embodiments, a particular filter can have a frequency range of 5-100 Hz. In some embodiments, a particular filter can have a frequency range of 5-95 Hz. In some embodiments, a particular filter can have a frequency range of 5-25 Hz. In some embodiments, a particular filter can have a frequency range of 5-50 Hz. In some embodiments, a particular filter can have a frequency range of 5-75 Hz.

In some embodiments, referring to FIG. 38, a K number of outputs (filtered PCG outputs) from each of the six filters are forwarded to the second stage. For example, in some embodiments, detailed below, K is equal to, but not limited to, 4. In some embodiments, K is equal to the number of acoustic sensors (M1-M4) being used to collect the acoustic sensor data. In some embodiments, a predetermined number of outputs is forwarded to the second stage.

Stage 2: Wavelet Denoising

In some embodiments, for example, one of the four filtered PCG outputs from the six bandpass filters is further subject to wavelet denoising, where such particular filtered PCG output is deconstructed by passing through a succession of low and high pass filters up to X times to form the deconstructed filtered PCG output. In some embodiments, the value of X depends on a sampling frequency which allows to achieve suitable results to meet requirements detailed below. For example, in some embodiments, the particular filtered PCG output is deconstructed by passing through a succession of low and high pass filters up to 3 times. For example, in some embodiments, the particular filtered PCG output is deconstructed by passing through a succession of low and high pass filters up to 5 times. For example, in some embodiments, the particular filtered PCG output is deconstructed by passing through a succession of low frequency pass and high frequency pass filters up to 6 times.

FIGS. 39A and 39B show illustrative diagrams of the exemplary denoising stage. In some embodiments, the result of the denoising is the wavelet transform coefficients called approximations and details. Specifically, the deconstructed filtered PCG output can be reconstructed using the details: Dj(n), j=1, . . . , N and the approximation Aj(n) to form the denoised filtered PCG output.

In some embodiments, the denoised filtered PCG output is determined based on equation 1:

$$y_r(n) = A_N(n) + \Sigma_{j=1}^N D_j(n) \tag{1}$$

Specifically, initially, in the first step of the denoising, all details that most likely do not carry information of the heartbeat signal are set to 0, for example but not limited to: D_j (n)=0, j=1, 2, 3, 5, 6, . . . , N. For example, details that do not contain sound data corresponding to S1 and/or S2 phases of the cardiac contraction cycle.

Then, the remaining detail, the fourth detail, is thresholded using a threshold calculated utilizing, for example but not limited to, Stein's Unbiased Risk Estimate (SURE) method illustrated by equation 2:

$$D_4(n) = \begin{cases} 0 & \forall\, D_4(n) < TH_{SURE} \\ D_4(n) & \text{Otherwise} \end{cases} \tag{2}$$

In some embodiments, the threshold can be calculated using any other similarly suitable method.

In some embodiments the remaining detail can be any of the details or a combination of them.

Lastly, the denoised filtered PCG output is calculated using equation (1).

Stage 3: ICA Transformation

Referring to FIG. 38, (1) the filtered PCG output and (2) the denoised filtered PCG output are further transformed using at least one ICA algorithm to form (1) the transformed filtered PCG output and (2) the transformed denoised filtered PCG output, respectively. In some embodiments, the exemplary ICA algorithm is, for example but not limited to, the FAST ICA algorithm. In some embodiments, the FAST ICA algorithm is, for example, utilized in accordance with "*Independent component analysis: Algorithms and applications*," Hyvarinen et al., *Neural Networks* 13 (4-5): 411-430 (2000), whose specific descriptions are hereby incorporated herein for such specific purpose.

The term "transformation(s)" as used herein refers to linear or non-linear mathematical transformations, which may include, inter alia, digital filtering, mathematical linear or non-linear decomposition, mathematical optimization.

Stage 4: Detection of Fetal and Maternal Heart Beats

To summarize, at this stage, all outputs of the filterbank, denoisng, and ICA, from the previous three stages are being utilized as a S number of detection heartbeat (DH) inputs, where S is a number of all outputs of the filterbank, denoisng, and ICA stages, calculated as L×M, as determined below:

1) M filtered PCG outputs, resulted from 4 signal data inputs of the acoustic sensors M1-M4 being passed through L bandpass filters;
2) M filtered ICA transforms of the filtered PCG outputs;
3) M denoised filtered PCG outputs; and
4) M denoised filtered ICA transforms of the denoised filtered PCG outputs, where M=L×K.

In some embodiments, the exemplary inventive system of the present detection assumes that the heart beats of the mother and/or the fetus(es) can be detected in each one of these DH inputs. In some embodiments, the exemplary inventive system has no prior historical data to suggest in which of these DH inputs the heartbeat of the fetus(es) would be detected, or the heartbeat of the mother, or both, or none.

For example, in some embodiments, the L number of filters in the filter bank is 6 and the total number of inputs for stage 4 is M×L=96.

In some embodiments, the stage 4 is further divided into four sub-stages:
Sub-stage 1: Detect all heartbeats in each of the DH inputs;
Sub-stage 2: Calculate a confidences score that describes the probability that the heartbeats detected in Step 1 are actual heartbeats and not the noise;
Sub-stage 3: Divide all the DH inputs into at least two groups:
  Group 1: fetal heartbeat outputs that contain fetal heartbeats
  Group 2: maternal heartbeat outputs that contain maternal heartbeats;
Sub-stage 4: Select from each group the most probable output that contains the corresponding heartbeat.

Sub-Stage 1: Heartbeat Detection

Typically, acoustic signal can contain at least some noise and heartbeats in at least some cases can be "covered" with noise or in a very noisy surrounding. In addition, typically, the heartbeat morphology can vary form one heartbeat to the next. In some embodiments, the Sub-stage 1 is carried out in at least the following number of steps.

Figure 40:
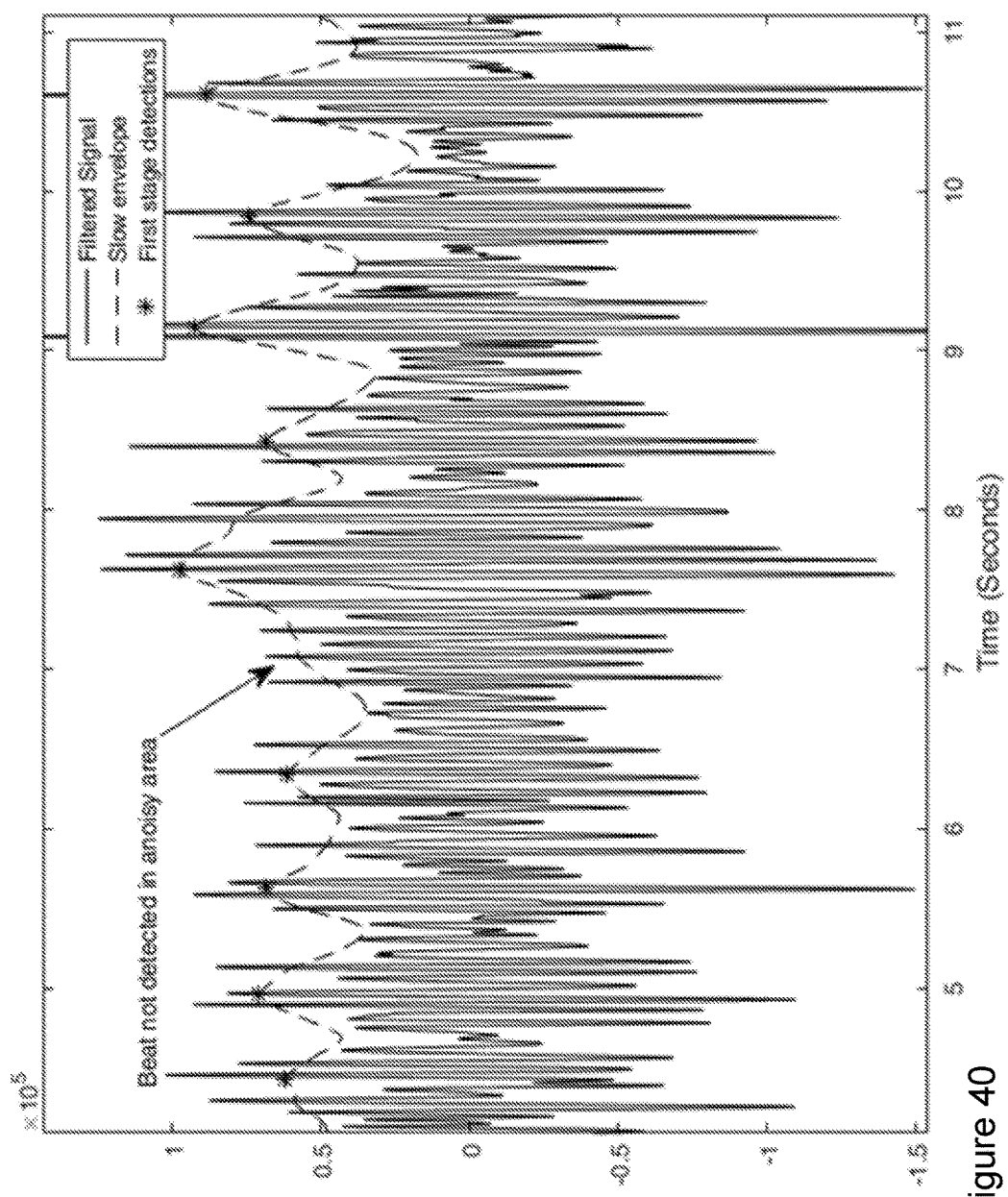
FIGS. 40-44 show graphs illustrating results of processing of data from acoustic sensors according to some embodiments of the present invention.

Step 1: Beat Detection
  i. In some embodiments, the exemplary inventive system of the present invention calculates a slow envelope of the absolute of the Hilbert transform of the acoustic signal. For instance, exemplary inventive system of the present invention calculates this envelope by applying a moving average filter on the absolute value of the Hilbert transform. In some embodiments, the exemplary inventive system of the present invention can utilize the moving average window having a predetermined length of P. For example, in some embodiments, P is 300 milliseconds (ms). In some embodiments, P varies from 100 to 500 ms. In some embodiments, P varies from 200 to 500 ms. In some embodiments, P varies from 300 to 500 ms. In some embodiments, P varies from 400 to 500 ms.
  ii. The exemplary inventive system of the present invention then determines all the peaks of the signal by identifying the zero crossings of the derivative of the signal in each respective DH input.
  iii. The exemplary inventive system of the present invention then discards all peaks that are not prominent enough, based, at least in part, on the following criteria used is:

$$\text{Select } \forall \text{ peaks such that} \frac{p(k)}{\text{median}([p(1), p(2), \ldots , p(N)])} > \text{Thresh } k = 1 \ldots N$$

where $p(k)$ is the prominence of the $k^{th}$ peak.

iv. The exemplary inventive system of the present invention then groups all peaks into two groups according to, for example, shape and size. For example, such grouping is done using a Gaussian Mixture model clustering algorithm with the following features for each peak:

the width of each peak divided by the max peak width, and the height of the peak divided by its prominence.

v. The exemplary inventive system of the present invention then selects a group of peaks that has the smallest variance measure as the peaks for the next steps.

vi. The exemplary inventive system of the present invention then repeats steps i-v using an average window length R ms. In some embodiments, the average window length of 250 ms. In some embodiments, the average window length is between 100-300 ms.

vii. The exemplary inventive system of the present invention then calculates the Excess Kurtosis measure of the distribution (an adjusted version of Pearson's kurtosis) for the locations of peaks, and selects the peak locations that provide the smallest Excess Kurtosis. FIG. 40 shows the result of the detection at this step, specifically the beat located in a noisy area is not detected.

viii. From the selected peaks locations, the exemplary inventive system of the present invention then calculates an initial estimate of the average Heart Rate (HR).

Step 2—Enhanced Detection

Figure 41:
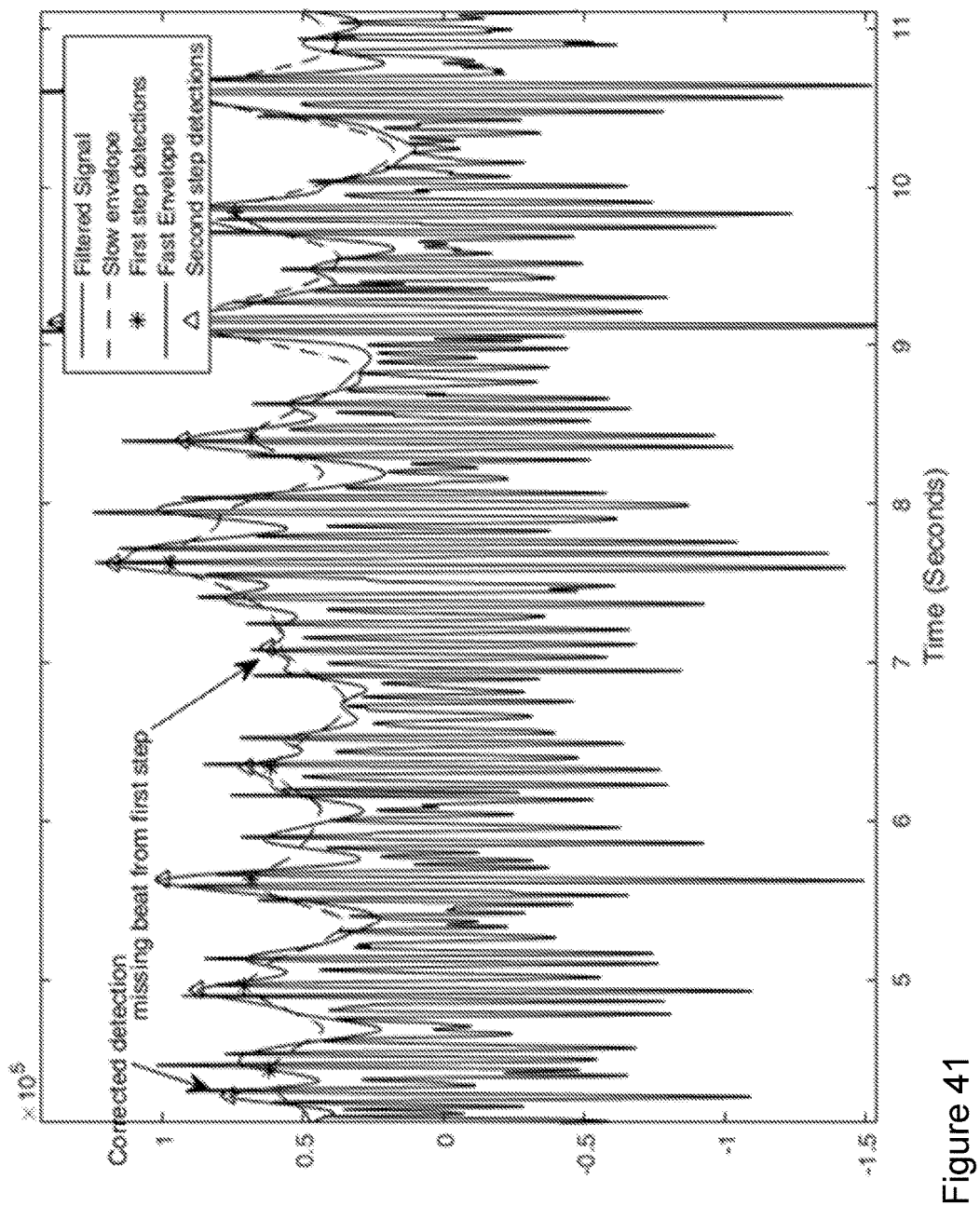

The exemplary inventive system of the present invention refines the detection results of Step 1 by, for example, adding missing beats and correcting the Step 1 detection locations.

i. The exemplary inventive system of the present invention calculates a fast envelope using a Q ms window in the same manner performed as detailed in item (i) of Step 1. For example, in some embodiments, Q is 100 ms. In some embodiments, Q varies between 50-200 ms. In some embodiments, Q varies between 50-150 ms. In some embodiments, Q varies between 50-100 ms.

ii. The exemplary inventive system of the present invention then identifies peaks on the fast envelope signal and selects all prominent peaks in same manner as detailed in item (iii) of Step 1.

iii. The exemplary inventive system of the present invention then calculates all beat to beat intervals (B2B) from the detection results of Step 1, where B2B is an interval between successive beats.

iv. Referring to FIG. 41, the exemplary inventive system of the present invention then completes missing beats which are not identified in Step 1, by reiteratively analyzing all beat to beat intervals determined in the item (iii) of Step 2 based on at least the following exemplary, but not limiting, conditions:

if B2B(k) is higher than 1.5×B2B(average) calculated in item (viii) of Step 1, find a peak from the fast envelope which is as close as possible to the last peak found in item (viii) of Step 1+B2B(average).

v. The exemplary inventive system of the present invention then corrects the detection of Step 1, using the fast envelope.

In some embodiments, the exemplary inventive system of the present invention performs Step 2 to the extent necessary to minimize the beat to beat variance.

Sub-Stage 2: Calculate a Confidence Score for the Heartbeat Detection

Figure 42:
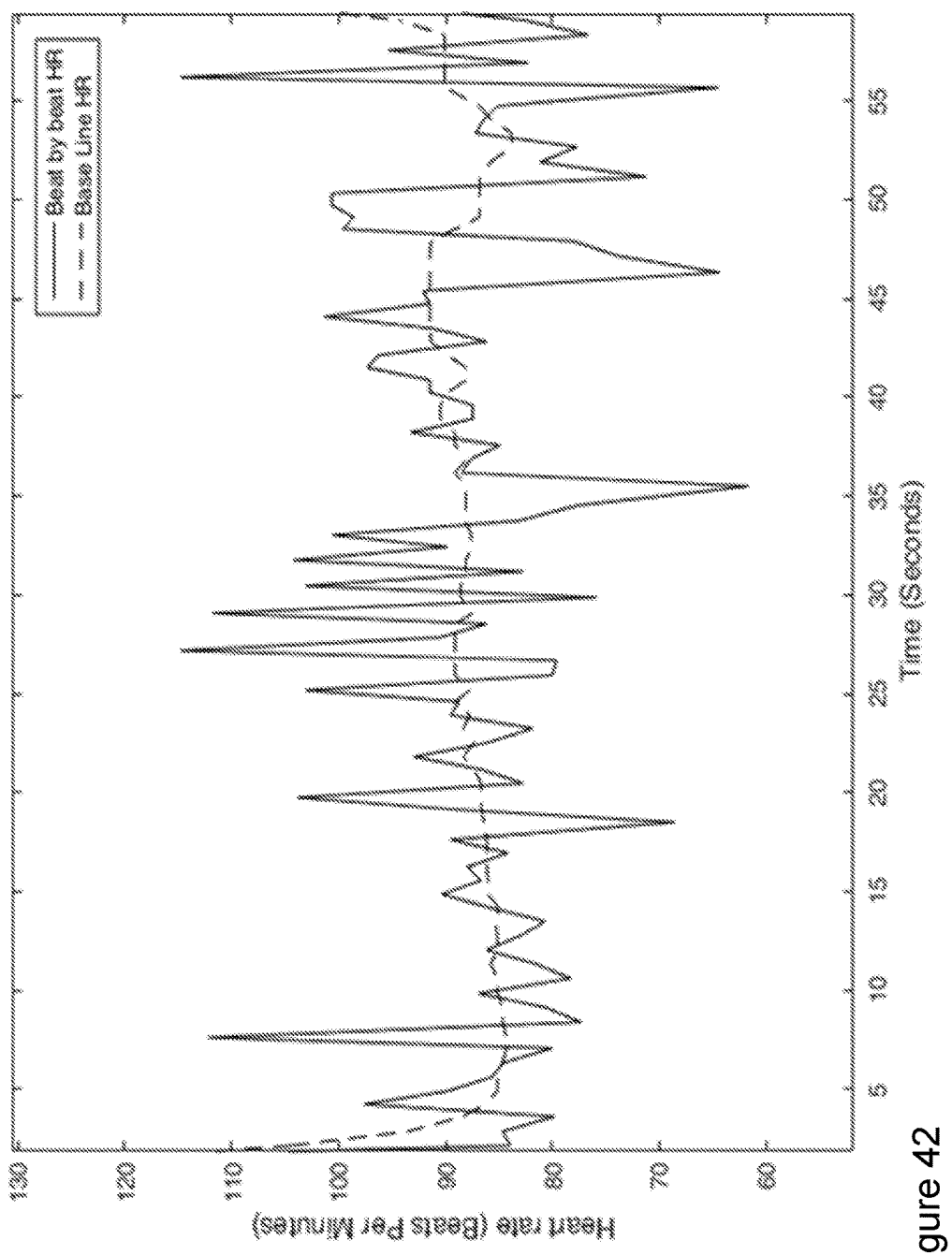

Typically, a beat-by-beat heart rate is a physiological signal which cannot change too fast and usually follows a baseline that defines an average heart rate. In some embodiments, the exemplary inventive system of the present invention utilizes the average heart rate as the base for calculating the confidence score. For each detection of heart beats (for example but not limited to 96 of them, obtained at the end of Sub-Stage 1 from 96 DH inputs), the exemplary inventive system of the present invention calculates the confidence score in accordance with the following steps.

i) The exemplary inventive system of the present invention generates a beat-by-beat heartbeat graph (shown in FIG. 42) based on the locations of the beats.

ii) The exemplary inventive system of the present invention then estimates the heart rate for the whole signal (HRestim), by calculating a histogram of all the beat-by-beat heart rates, where the estimated heart rate for the whole signal is at the maximum of the histogram.

iii) The exemplary inventive system of the present invention then estimates a base line for the beat-by-beat heartbeat graph (FIG. 42) using a median filter (e.g., order 20, etc.).

iv) The exemplary inventive system of the present invention then calculates the confidence score based on the following equation (3):

$$Score = \sqrt{\frac{MfRR^2 + SfRR^2 + OvMP^2}{3}}, \quad (3)$$

where $MfRR = \dfrac{\sum_{n=1}^{N} |HR(n) - HRestim|}{N}$, $SfRR = std(|HR(n) - HRestim|)$, $OvMP = \dfrac{1}{N}\sum 1_{HR}$, $1_{HR} = \begin{cases} 1, & |HR(n) - HRestim| < HRestim \times 0.15 \\ 0, & \text{otherwise} \end{cases}$.

Sub-Stage 3: Group all Heartbeat Detections into 2 Groups: Maternal and Fetal

Based on the Stages 1-3 and Sub-stages 1-2, The exemplary inventive system of the present invention generates S beat-by-beat heartbeat graphs, which are vectors representative of the DH inputs obtained from Stages 1-3 (DH input vectors). For example, in case of 96 DH inputs, 96 beat-by-beat heartbeat graphs is generated. Some of the DH input vectors represent maternal heartbeat and some represent the fetal heartbeat.

In some embodiments, the exemplary inventive system of the present invention can utilize, for example, other contemporaneous maternal heartbeat data about the maternal heartbeat which has been separately determined based on data collected from non-acoustic sensor(s)/equipment (e.g., ECG data) to group all DH input vectors that are highly correlated with the other contemporaneous maternal heartbeat data as candidates for maternal heart rate detection and the remaining DH input vectors are grouped as fetal heartbeat candidates.

In some embodiments, when the other contemporaneous maternal heartbeat data is not available, the exemplary inventive system of the present invention can group the DH input vectors, by clustering the estimated heart rate of each DH input vector according to its value. In some embodiments, the exemplary inventive system of the present invention then designates the DH input vectors with a higher average heartbeat rate into the fetal heartbeat group.

Sub-Stage 4: Select the Fetal and Maternal Best Detections

In some embodiments, based on the best confidence score, the exemplary inventive system of the present invention selects the best representative maternal DH input vector as the best detection of the maternal heartbeat rate from the group of the maternal heartbeat DH input vectors identified in Sub-stage 3.

In some embodiments, based on the best confidence score, the exemplary inventive system of the present invention selects the best representative fetal DH input vector as the best detection of the fetal heartbeat rate from the group of the fetal DH input vectors identified in Sub-stage 3.

Figure 43:
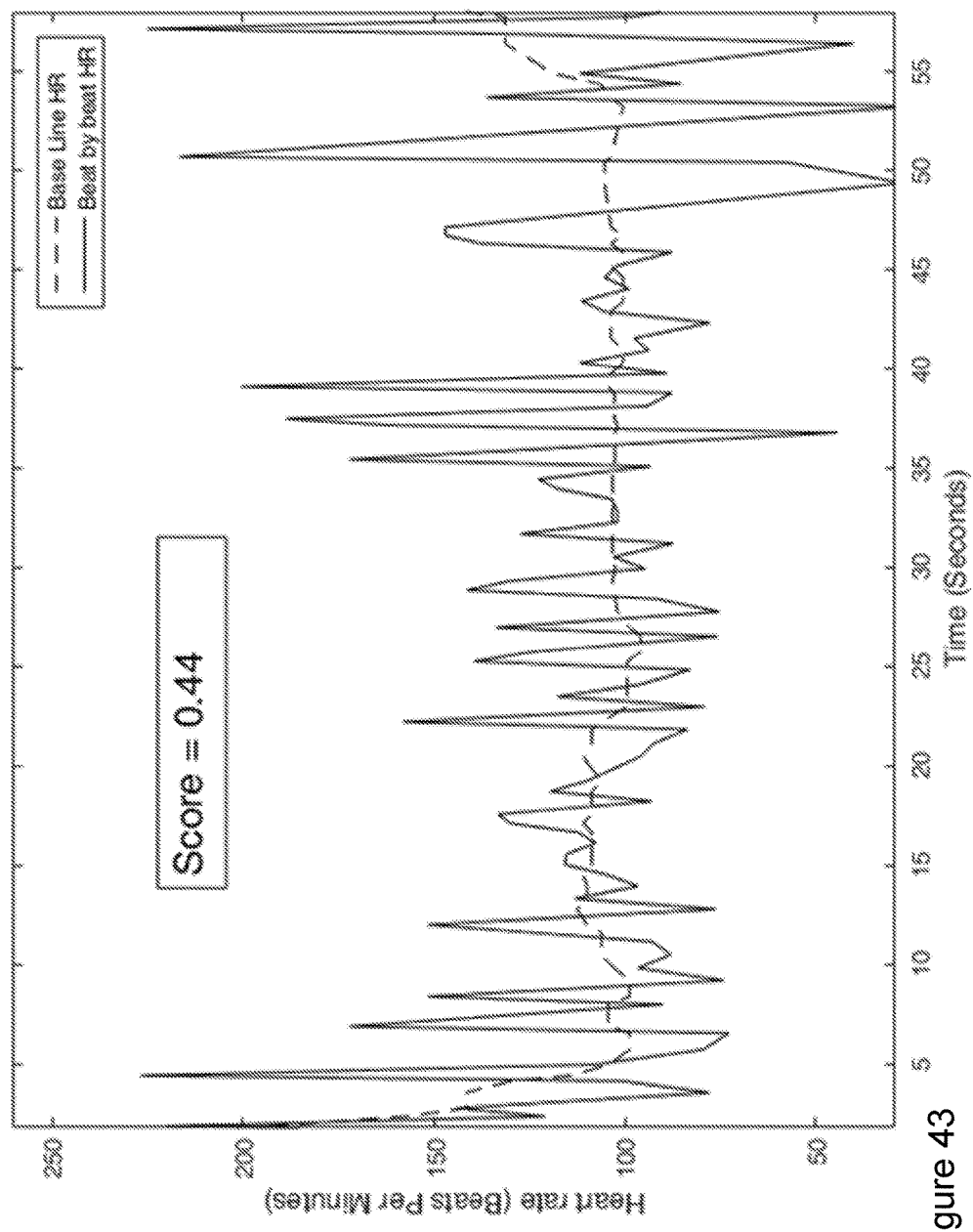

FIG. 43 shows an illustrative example a beat-by-beat heartbeat graph representative of an exemplary DH input vector with a low confidence score.

Figure 44:
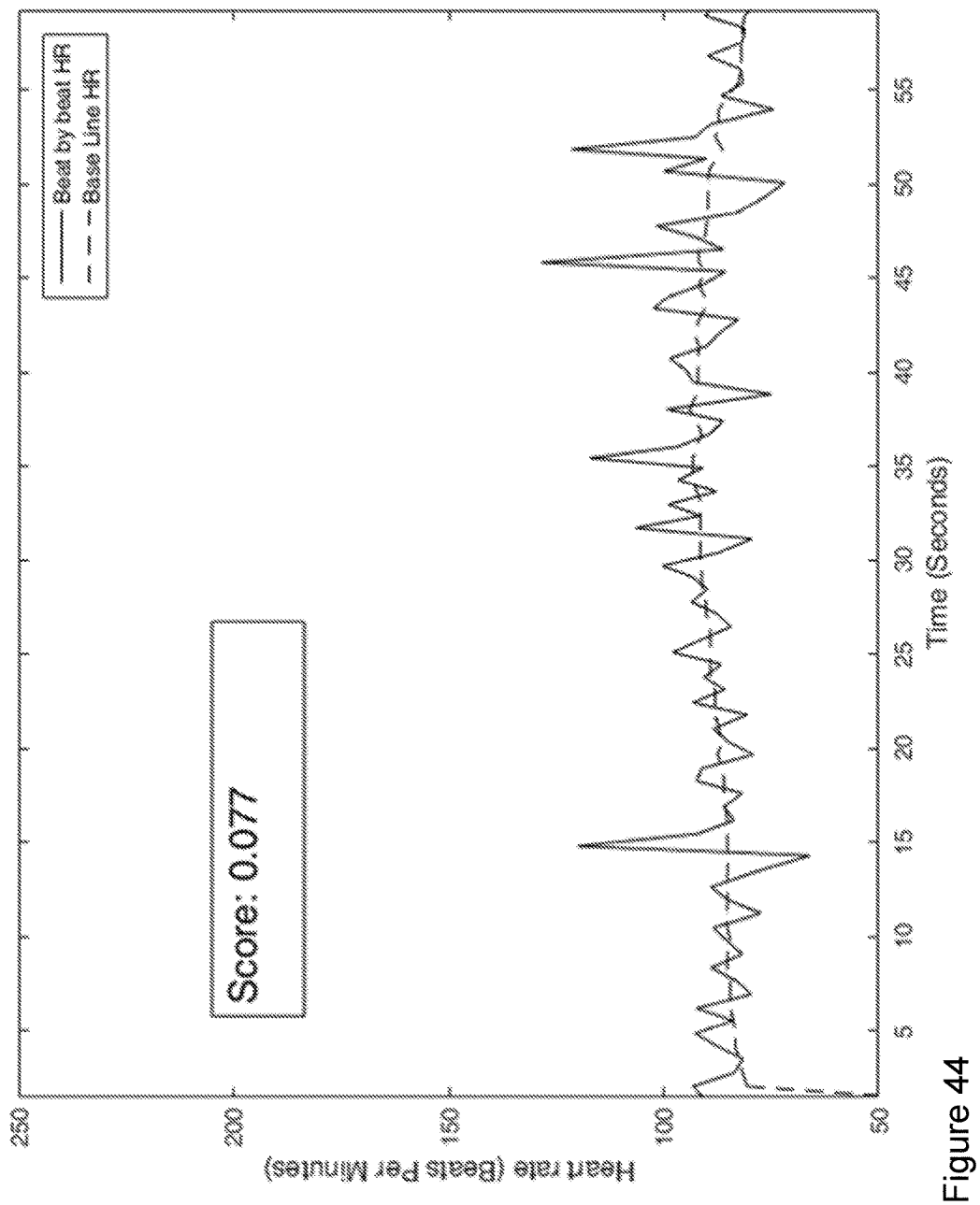

FIG. 44 shows an illustrative example a beat-by-beat heartbeat graph representative of an exemplary DH input vector with a high confidence score.

In some embodiments, the instant invention is directed to a computer-implemented method which includes at least the steps of: receiving, by at least one computer processor executing specific programmable instructions configured for the method, a plurality of Phonocardiogram (PCG) signals data inputs from a plurality of acoustic sensors; digital signal filtering, by the at least one computer processor, utilizing a plurality of bandpass filters, the plurality of PCG signals data inputs to form a plurality of filtered PCG outputs, where the plurality of bandpass filters includes a L number of bandpass filters, where each bandpass filter outputs a K number of filtered PCG outputs; wavelet denoising, by the at least one computer processor, a first subset of filtered PCG outputs of the plurality of filtered PCG outputs to form a M number of denoised filtered PCG outputs, where M is equal to L multiply by K; transforming, by the at least one computer processor, utilizing an Independent-Component-Analysis (ICA), a second subset of filtered PCG outputs of the plurality of filtered PCG outputs to form the M number of filtered ICA transforms; transforming, by the at least one computer processor, utilizing the Independent-Component-Analysis (ICA), a first portion of the second subset of denoised filtered PCG outputs to form the M number of filtered denoised filtered ICA transforms; compiling, by the at least one computer processor, a S number of a plurality of detection heartbeat (DH) inputs, including: i) the M number of filtered PCG outputs, ii) the M number of denoised filtered PCG outputs, iii) the M number of filtered ICA transforms, and iv) the M number of denoised filtered ICA transforms; detecting, by the at least one computer processor, beat locations of beats in each of DH inputs; calculating, by the at least one computer processor, a confidence score that describes a probability that the beats in each DH input of the plurality of DH inputs represent actual heartbeats and not a noise; dividing, by the at least one computer processor, the plurality of DH inputs into at least two groups: i) a first group of DH inputs containing fetal heartbeats, ii) a second group of DH inputs containing maternal heartbeats selecting, by the at least one computer processor, from the first group of DH inputs, at least one particular fetal DH input that contains the fetal heartbeat based on a first confidence score of the at least one particular fetal DH input; and selecting, by the at least one computer processor, from the second group of DH inputs, at least one particular maternal DH input that contains the maternal heartbeat, based on a second confidence score of the at least one particular maternal DH input.

In some embodiments, where the wavelet denoising includes at least: deconstructing, by the at least one computer processor, each filtered PCG output to generate a plurality of transform coefficients, by irrelatively passing each filtered PCG output through a succession of low and high pass filters; identifying, by the at least one computer processor, a subset of heartbeat-carrying transform coefficients from the plurality of transform coefficients, reconstructing, by the at least one computer processor, the subset of heartbeat-carrying transform coefficients to form the M number of denoised filtered PCG outputs.

In some embodiments, K is equal to a number of the plurality of acoustic sensors, and L is equal to 6.

In some embodiments, each filter of the plurality of bandpass filters has a bandwidth of 10-100 Hz and a frequency range of 5-110 HZ.

In some embodiments, the detecting of the beat locations of the beats in each of DH inputs includes at least: calculating, by the at least one computer processor, a predetermined transform filter; iteratively repeating, by the at least one computer processor, based on a predetermined average window length of the predetermined transform filter: identifying, in each DH input, a subset of peaks having a predetermined shape and a predetermined size, and selecting a group of peaks from the subset of peaks, where the group of peaks has the smallest variance measure; calculating, by the at least one computer processor, initial locations of the beats.

In some embodiments, the calculating the confidence score includes at least: generating, by the at least one computer processor, a beat-by-beat heartbeat graph for each DH input based on the beat locations.

In some embodiments, the dividing the plurality of DH inputs into the first group of DH inputs containing fetal heartbeats and the second group of DH inputs containing maternal heartbeats includes at least: clustering, by the at least one computer processor, the beats of each DH input according to each beat value; and assigning, by the at least one computer processor, a particular DH input having a higher average beat rate into the first group of DH inputs containing fetal heartbeats.

In some embodiments, the present invention is directed to a specifically programmed computer system, including at least the following components: at least one specialized computer machine, including: a non-transient memory, electronically storing particular computer executable program code; and at least one computer processor which, when executing the particular program code, becomes a specifically programmed computing processor that is configured to at least perform the following operations: receiving a plurality of Phonocardiogram (PCG) signals data inputs from a plurality of acoustic sensors; digital signal filtering, utilizing a plurality of bandpass filters, the plurality of PCG signals data inputs to form a plurality of filtered PCG outputs, where the plurality of bandpass filters includes a L number of bandpass filters, where each bandpass filter outputs a K number of filtered PCG outputs; wavelet denoising a first subset of filtered PCG outputs of the plurality of filtered PCG outputs to form a M number of denoised filtered PCG outputs, where M is equal to L multiply by K; transforming, utilizing an Independent-Component-Analysis (ICA), a second subset of filtered PCG outputs of the plurality of filtered PCG outputs to form the M number of filtered ICA transforms; transforming, utilizing the Independent-Component-Analysis (ICA), a first portion of the second subset of denoised filtered PCG outputs to form the M number of denoised filtered ICA transforms; compiling a S number of a plurality of detection heartbeat (DH) inputs, including: i) the M number of filtered PCG outputs, ii) the M number of denoised filtered PCG outputs, iii) the M number of filtered ICA transforms, and iv) the M number of denoised filtered ICA transforms; detecting beat locations of beats in each of DH inputs; calculating a confidence score that describes a probability that the beats in each DH input of the plurality of DH inputs represent actual heartbeats and not a noise; dividing the plurality of DH inputs into at least two groups:

i) a first group of DH inputs containing fetal heartbeats, ii) a second group of DH inputs containing maternal heartbeats; selecting, from the first group of DH inputs, at least one particular fetal DH input that contains the fetal heartbeat based on a first confidence score of the at least one particular fetal DH input; and selecting, from the second group of DH inputs, at least one particular maternal DH input that contains the maternal heartbeat, based on a second confidence score of the at least one particular maternal DH input.

Figure 45:
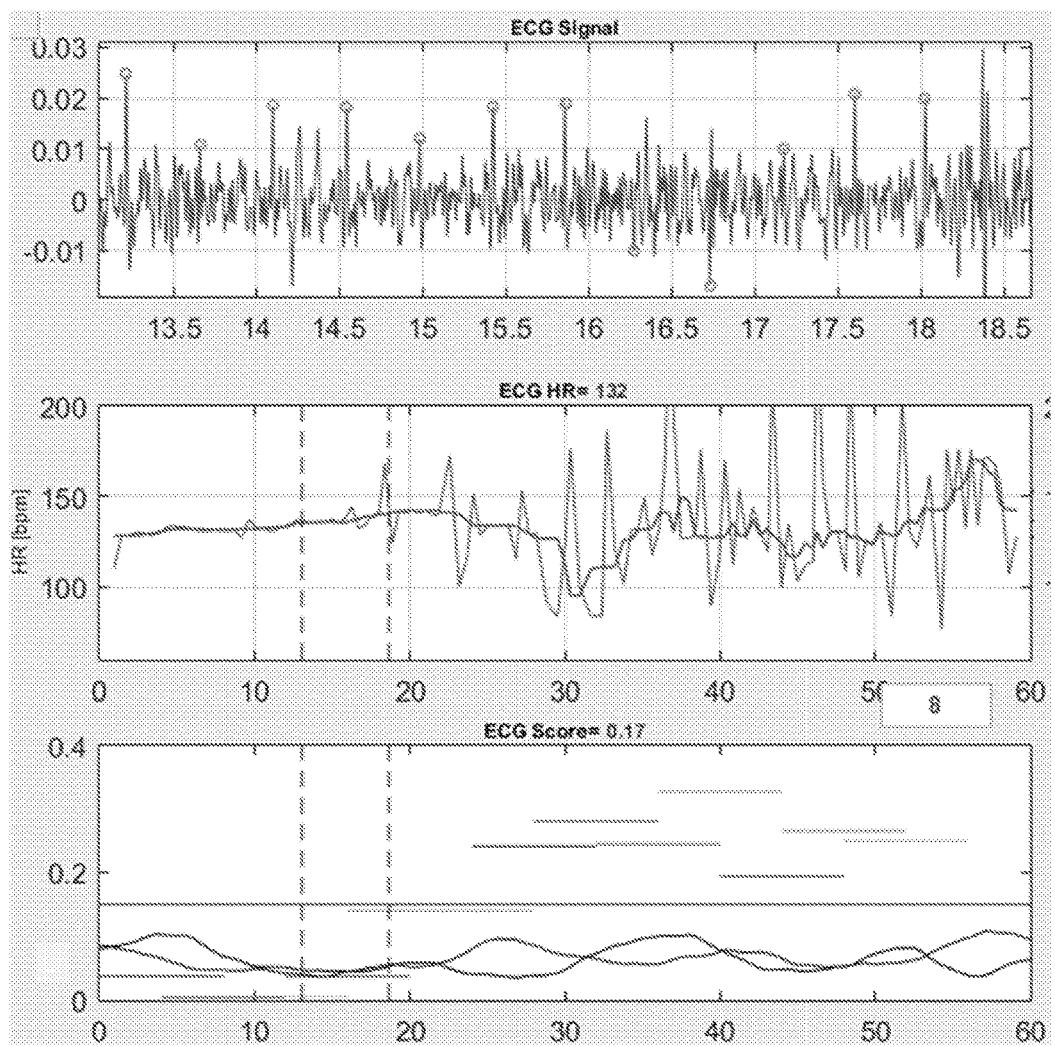
FIG. 45 shows a graphical display where the ECG signals data has "good" signal properties, but the PCG signals data has "poor" signal properties.
Figure 46:
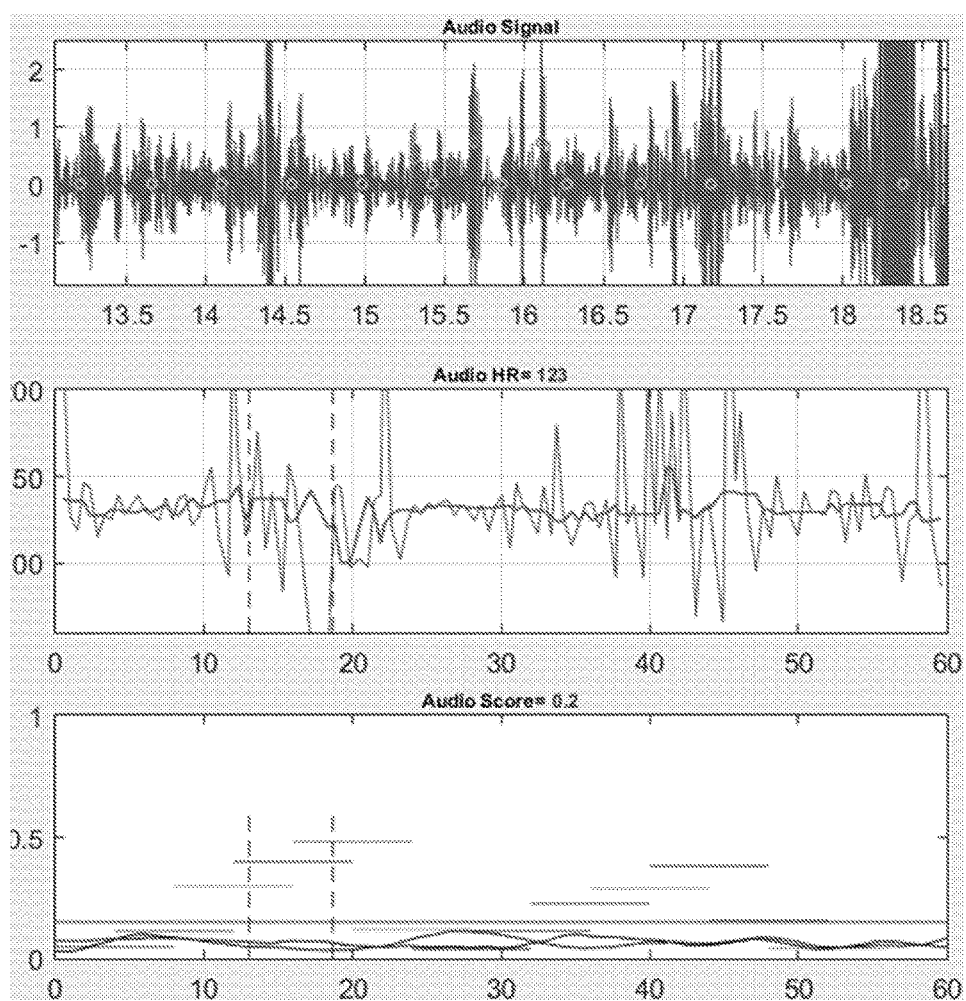
FIG. 46 shows a graphical display where the PCG signals data has "good" signal properties, but the ECG signals data is "poor" shows a graphical display where the ECG signals data has "good" signal properties, but the PCG signals data is "poor".

Estimating Fetal Heart Rate Over a Particular Time Interval According to Some Embodiments of the Present Invention Referring to FIG. 45, a graphical representation is shown where the ECG signals data has "good" signal properties (i.e. is a signal from which fetal heart beats can be detected), but the PCG signals data has "poor" signal properties. Similarly, referring to FIG. 46, a graphical representation is shown where the PCG signals data has "good" signal properties, but the ECG signals data is "poor" shows a graphical display where the ECG signals data has "good" signal properties, but the PCG signals data is "poor".

It is an objective of the present invention to combine the ECG signals data and the PCG signals data to increase the accuracy of the system of the present invention to consolidate ECG signals data and PCG signals data recorded over a particular time interval to calculate an estimation of fetal heart rate over the particular time interval.

In some embodiments, the present invention provides a system for generating an estimation of fetal cardiac activity over a particular time interval comprising:
a) a specifically programmed computer system comprising: at least one specialized computer machine, comprising: a non-transient memory, electronically storing particular computer executable program code; and at least one computer processor which, when executing the particular program code, becomes a specifically programmed computing processor that is configured to at least perform the following operations:
  i. receiving a calculated fetal heart rate for a plurality of time points over a particular time interval from filtered N-ECG fetal signals data and a calculated fetal heart rate for a plurality of time points over a particular time interval from filtered PCG outputs;
  ii. determining the score of the calculated fetal heart rate for the plurality of time points over the particular time interval for the filtered N-ECG fetal signals;
  iii. determining the score of the calculated fetal heart rate for the plurality of time points over the particular time interval for the filtered PCG outputs;
  iv. based on the calculated fetal heart rate and score for a plurality of time points over a particular time interval from filtered N-ECG fetal signals data, and the calculated fetal heart rate and score for a plurality of time points over a particular time interval from filtered PCG outputs, determining a consolidated fetal heart rate and score for the plurality of time points over the particular time interval,
    wherein the consolidated fetal heart rate and score for an individual time point within the plurality of time points is determined as one of the four options selected from the group consisting of:
      1. the weighted average of the calculated heart rate from the filtered N-ECG fetal signals data and the filtered PCG outputs for the individual time point, if the calculated heart rate from the filtered N-ECG fetal signals data and the filtered PCG outputs for the individual time point differs by 10 beats per minute or less, and if the scores of the calculated fetal heart rate for the individual time point for both the filtered N-ECG fetal signals data and the filtered PCG outputs are valid;
      2. the calculated heart rate having the lower score, if the calculated heart rate from the filtered N-ECG fetal signals data and the filtered PCG outputs for the individual time point differs by more than 10 beats per minute, and if the scores of the calculated fetal heart rate for the individual time point for both the filtered N-ECG fetal signals data and the filtered PCG outputs are valid;
      3. the calculated heart rate that has the valid score; and
      4. no consolidated fetal heart rate and score, if neither the calculated heart rate from the filtered N-ECG fetal signals data or the filtered PCG outputs has a valid score;
  v. based on the consolidated heart rate and scores for the plurality of time points over the particular time interval, generating, by the at least one computer processor, a fetal heart rate probability mesh;
  vi. based on the fetal heart rate probability mesh, generating, by the at least one computer processor, an estimated fetal heart rate over the particular time interval,
    wherein the estimated fetal heart rate over the particular time interval is calculated based on (1) cost representing fetal heart probability mesh values at each point of the estimated fetal heart rate over the particular time interval; and (2) cost representing the overall tortuosity of the estimated fetal heart rate over the particular time interval.

In some embodiments, referring to FIG. 32, fetal hear rate is calculated filtered N-ECG signals data and the filtered PCG outputs using the RR interval of the fetal cardiac activity cycle.

In some embodiments, the present invention provides a computer-implemented method, that includes:
a) receiving a calculated fetal heart rate for a plurality of time points over a particular time interval from filtered N-ECG fetal signals data and a calculated fetal heart rate for a plurality of time points over a particular time interval from filtered PCG outputs;
b) determining the score of the calculated fetal heart rate for the plurality of time points over the particular time interval for the filtered N-ECG fetal signals;
c) determining the score of the calculated fetal heart rate for the plurality of time points over the particular time interval for the filtered PCG outputs;
d) based on the calculated fetal heart rate and score for a plurality of time points over a particular time interval from filtered N-ECG fetal signals data, and the calculated fetal heart rate and score for a plurality of time points over a particular time interval from filtered PCG outputs, determining a consolidated fetal heart rate and score for the plurality of time points over the particular time interval,
  wherein the consolidated fetal heart rate and score for an individual time point within the plurality of time points is determined as one of the four options selected from the group consisting of:
    1. the weighted average of the calculated heart rate from the filtered N-ECG fetal signals data and the filtered PCG outputs for the individual time point, if the calculated heart rate from the filtered N-ECG fetal signals data and the filtered PCG outputs for the individual time point differs by 10 beats per minute or less, and if the scores of the calculated fetal heart rate for the individual time point for both the filtered N-ECG fetal signals data and the filtered PCG outputs are valid;
2. the calculated heart rate having the lower score, if the calculated heart rate from the filtered N-ECG fetal signals data and the filtered PCG outputs for the individual time point differs by more than 10 beats per minute, and if the scores of the calculated fetal heart rate for the individual time point for both the filtered N-ECG fetal signals data and the filtered PCG outputs are valid;
3. the calculated heart rate that has the valid score; and
4. no consolidated fetal heart rate and score, if neither the calculated heart rate from the filtered N-ECG fetal signals data or the filtered PCG outputs has a valid score;

e) based on the consolidated heart rate and scores for the plurality of time points over the particular time interval, generating, by the at least one computer processor, a fetal heart rate probability mesh;

f) based on the fetal heart rate probability mesh, generating, by the at least one computer processor, an estimated fetal heart rate over the particular time interval,
  wherein the estimated fetal heart rate over the particular time interval is calculated based on (1) cost representing fetal heart probability mesh values at each point of the estimated fetal heart rate over the particular time interval; and (2) cost representing the overall tortuosity of the estimated fetal heart rate over the particular time interval.

In some embodiments, the particular time interval is 120 seconds. In some embodiments, the particular time interval is 110 seconds. In some embodiments, the particular time interval is 100 seconds. In some embodiments, the particular time interval is 90 seconds. In some embodiments, the particular time interval is 80 seconds. In some embodiments, the particular time interval is 70 seconds. In some embodiments, the particular time interval is 60 seconds. In some embodiments, the particular time interval is 50 seconds. In some embodiments, the particular time interval is 40 seconds. In some embodiments, the particular time interval is 30 seconds. In some embodiments, the particular time interval is 20 seconds. In some embodiments, the particular time interval is 10 seconds.

In some embodiments, data is acquired every five seconds within the particular time interval. In some embodiments, data is acquired every four seconds within the particular time interval. In some embodiments, data is acquired every three seconds within the particular time interval. In some embodiments, data is acquired every two seconds within the particular time interval. In some embodiments, data is acquired every one second within the particular time interval.

Figure 47:
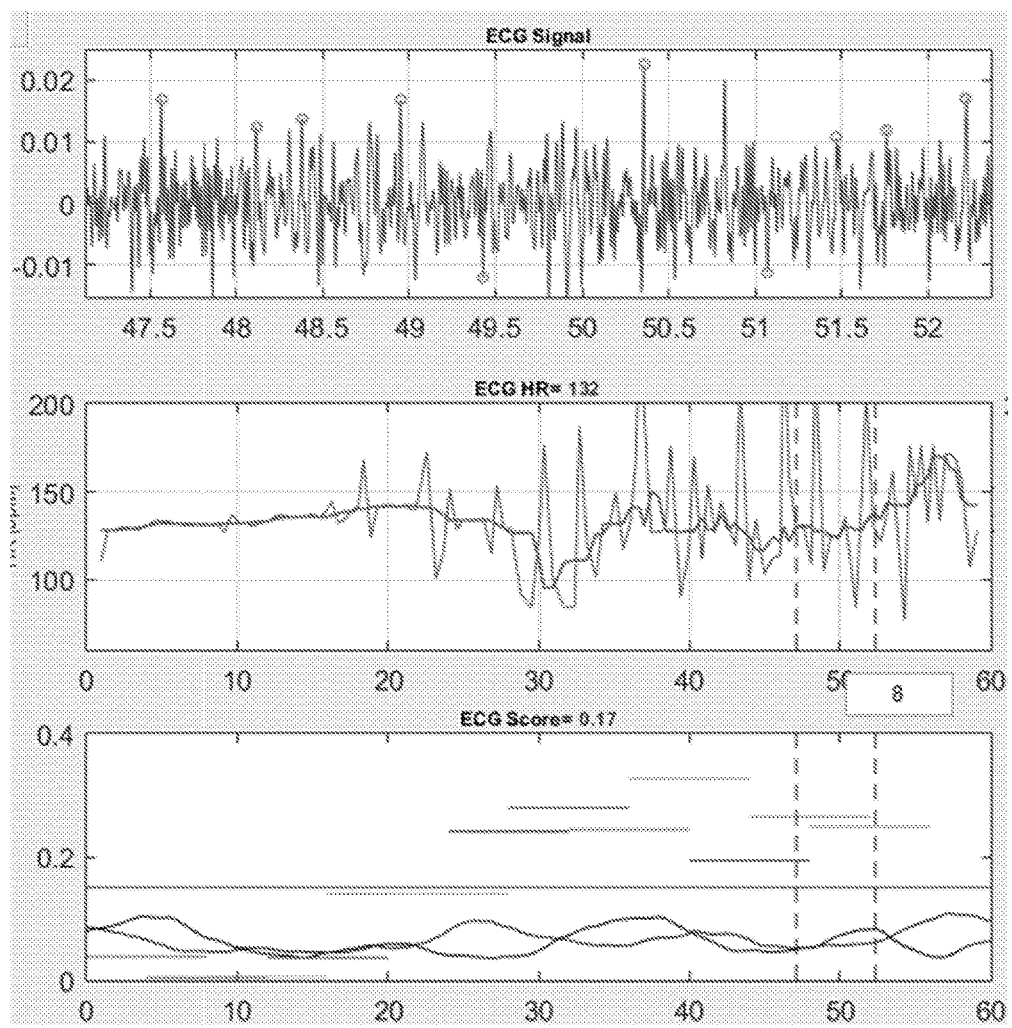
FIG. 47 shows a graphical display of the calculated fetal heart rate and scores for a plurality of time points over a particular time interval from the filtered N-ECG fetal signals data and the calculated fetal heart rate for a plurality of time points over a particular time interval from the filtered PCG outputs Scores are displayed by the marker fullness—a fuller marker means a lower score, meaning higher confidence in the single fetal heart rate estimation.
Figure 48:
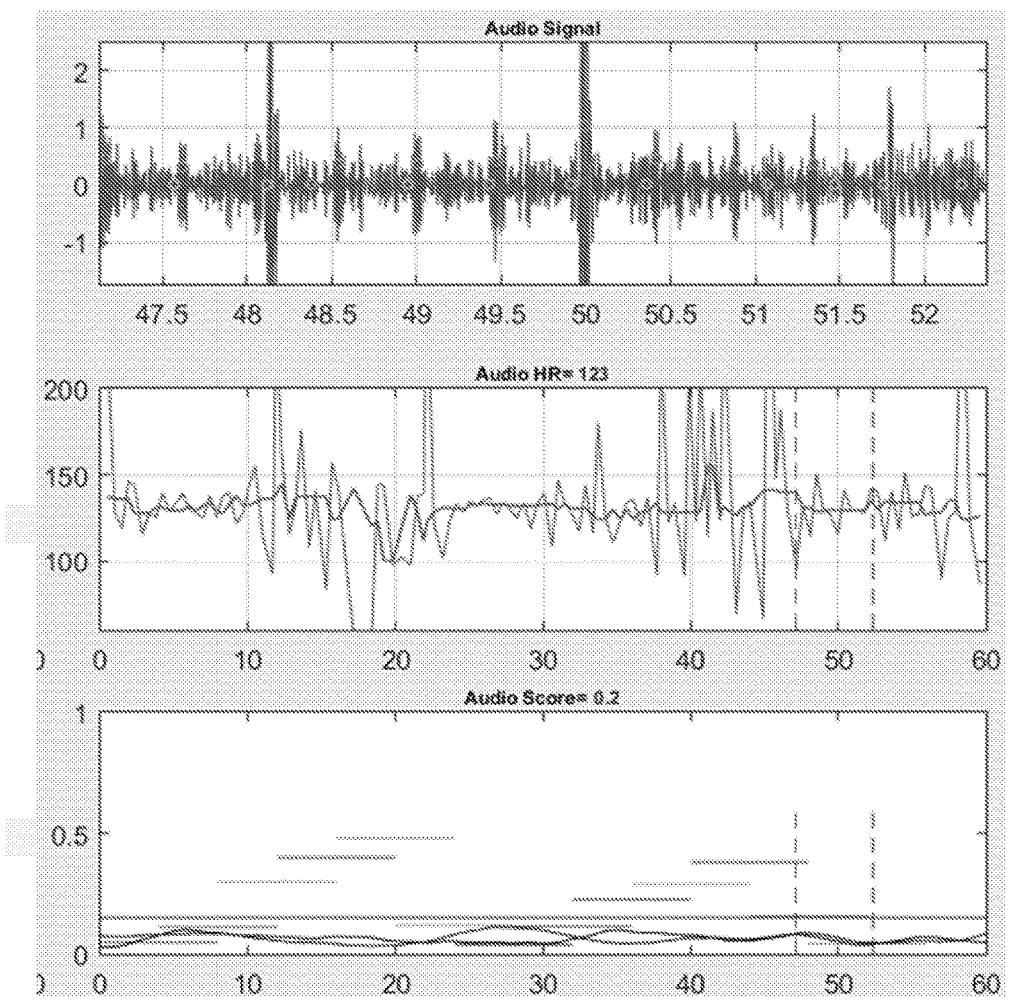
FIG. 48 shows a graphical display of the consolidated fetal heart rate and scores for a plurality of time points over a particular time interval. Scores are displayed by the marker fullness—a fuller marker means a lower score, meaning higher confidence in the single fetal heart rate estimation.

In some embodiments, referring to FIGS. 47 to 48, the specifically programmed computer system determines consolidated fetal heart rate estimations and scores for individual time points within the particular time period wherein the consolidated fetal heart rate and score for an individual time point within the plurality of time points is determined as one of the four options selected from the group consisting of:
1. the weighted average of the calculated heart rate from the filtered N-ECG fetal signals data and the filtered PCG outputs for the individual time point, if the calculated heart rate from the filtered N-ECG fetal signals data and the filtered PCG outputs for the individual time point differs by 10 beats per minute or less, and if the scores of the calculated fetal heart rate for the individual time point for both the filtered N-ECG fetal signals data and the filtered PCG outputs are valid;
2. the calculated heart rate having the lower score, if the calculated heart rate from the filtered N-ECG fetal signals data and the filtered PCG outputs for the individual time point differs by more than 10 beats per minute, and if the scores of the calculated fetal heart rate for the individual time point for both the filtered N-ECG fetal signals data and the filtered PCG outputs are valid;
3. the calculated heart rate that has the valid score; and
4. no consolidated fetal heart rate and score, if neither the calculated heart rate from the filtered N-ECG fetal signals data or the filtered PCG outputs has a valid score.

In some embodiments, the weighted average, is determined as follows:

$$\left(\frac{Acoustic_{Score}}{ECG_{Score} + Acoustic_{Score}}\right) \cdot ECG_{HR} + \left(\frac{ECG_{Score}}{ECG_{Score} + Acoustic_{Score}}\right) \cdot Acoustic_{HR}$$

In some embodiments, the score for the consolidated fetal heart rate estimation above is as follows:

$$\left(\frac{Acoustic_{Score}}{ECG_{Score} + Acoustic_{Score}}\right) \cdot ECG_{Score} + \left(\frac{ECG_{Score}}{ECG_{Score} + Acoustic_{Score}}\right) \cdot Acoustic_{Score}$$

In some embodiments, the calculated heart rate from the filtered N-ECG fetal signals data or the filtered PCG outputs for the individual time point is valid, if the score of the calculated heart rate from the filtered N-ECG fetal signals data or the filtered PCG outputs is not greater than 0.15. Alternatively, the calculated heart rate from the filtered N-ECG fetal signals data or the filtered PCG outputs for the individual time point is valid, if the score of the calculated heart rate from the filtered N-ECG fetal signals data or the filtered PCG outputs is not greater than 0.2. Alternatively, the calculated heart rate from the filtered N-ECG fetal signals data or the filtered PCG outputs for the individual time point is valid, if the score of the calculated heart rate from the filtered N-ECG fetal signals data or the filtered PCG outputs is not greater than 0.10. Alternatively, the calculated heart rate from the filtered N-ECG fetal signals data or the filtered PCG outputs for the individual time point is valid, if the score of the calculated heart rate from the filtered N-ECG fetal signals data or the filtered PCG outputs is not greater than 0.05.

Alternatively, in some embodiments, the at least one computer processor, instead of generating a set of consolidated fetal heart rare estimations and scores, uses either the heart rate determined by either the filtered N-ECG fetal signals data or the filtered PCG outputs.

In some embodiments, a fetal heart rate probability mesh is generated from the consolidated fetal heart rate estimations and scores. In some embodiments, the fetal heart rate probability function for each individual time point within the plurality of time points is modeled as a flipped normalized probability density function. In some embodiments, the fetal heart rate probability function is calculated as follows:
1. Defined for all possible fetal heart rate values ranging from 60 to 180 beats per minute.
2. Location of minimum is set to be the fetal heart rate estimation.
3. Value of minimum is calculated according to score (better score translates to a deeper peak).
4. Width of function is calculated according to score (better score translates to narrower probability function).

Figure 49:
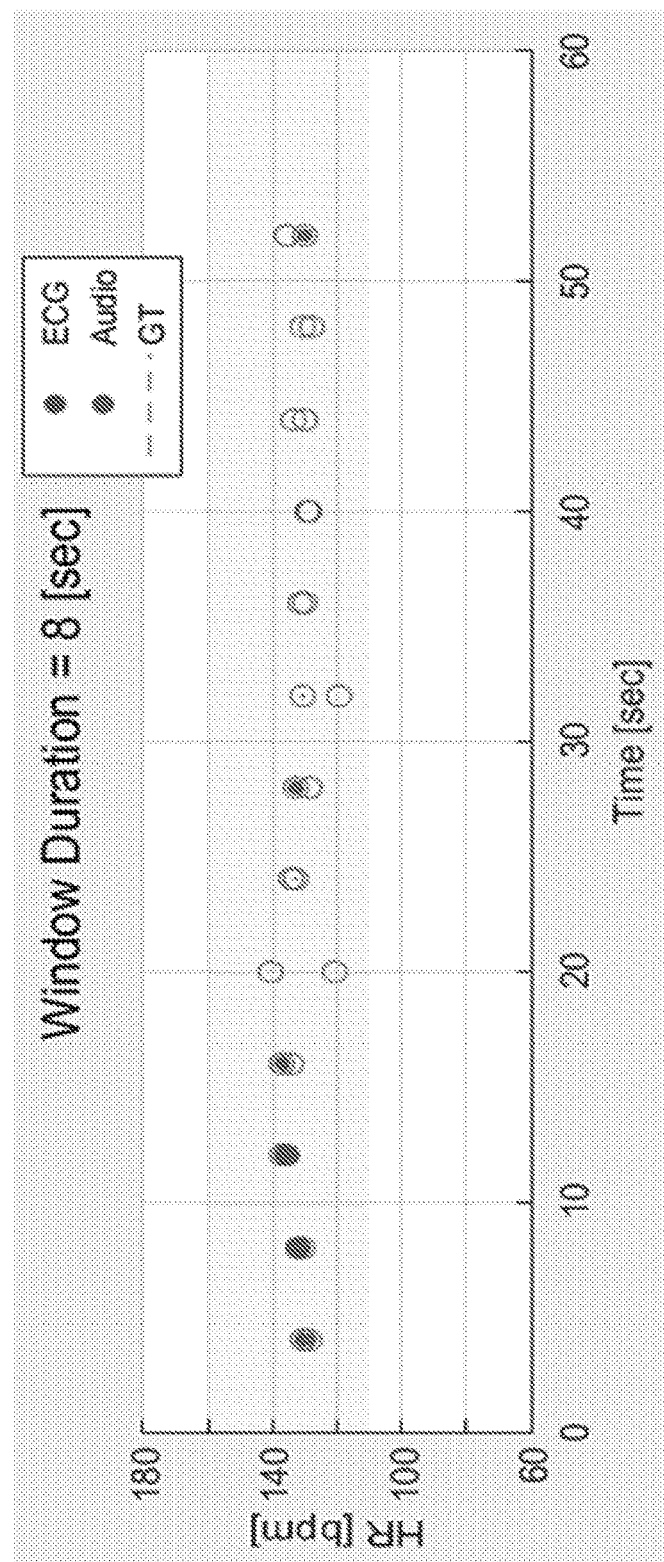
FIG. 49 shows a fetal heart rate probability mesh, based on fetal heart rate estimation and score, as a function of heart rate (beats per minute) and time (seconds).
Figure 50:
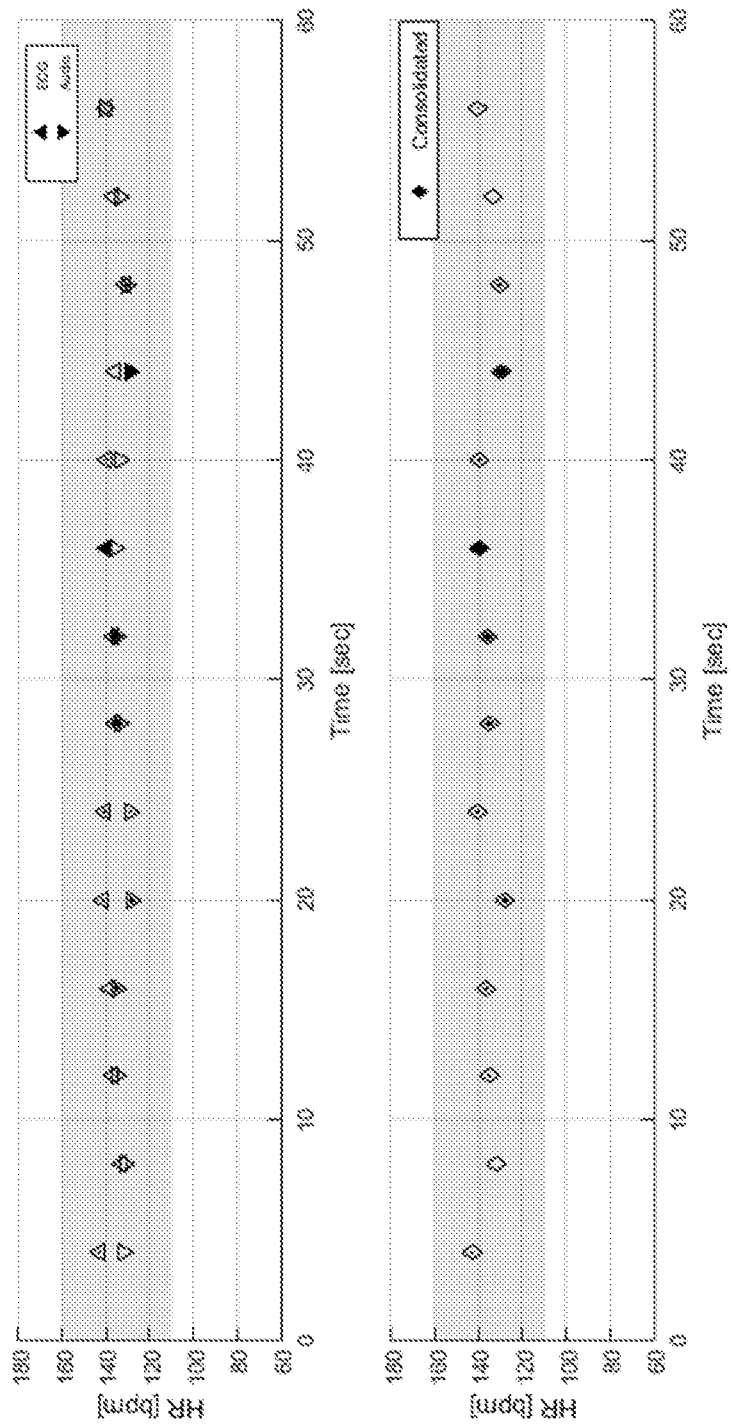
FIG. 50 shows a fetal heart rate probability mesh, based on fetal heart rate estimation and score, as a function of heart rate (beats per minute) and time (seconds).
Figure 51:
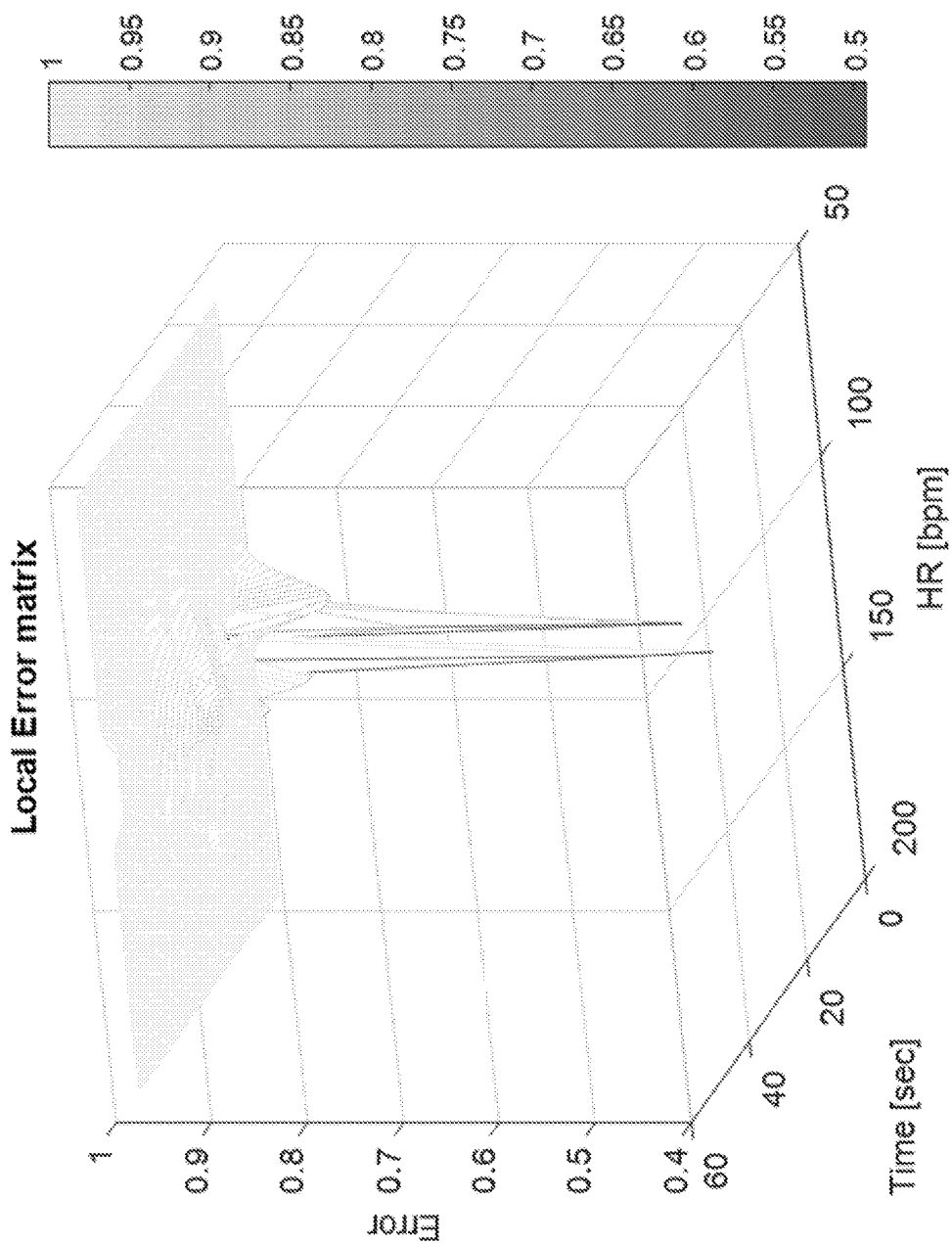
FIG. 51 shows an estimated fetal heart rate over the particular time interval, calculated according to some embodiments of the present invention.

An example of a fetal heart rate probability mesh according to some embodiments of the present invention is shown in FIGS. 49 and 50.

In some embodiments, an estimation of the fetal heart rate over the entire particular period of time is generated by the specifically programmed computer, using the fetal heart rate probability mesh.

In some embodiments, estimating the fetal heart rate over the particular time interval is achieved by calculating an estimation with minimal accumulated cost; wherein the minimal accumulated cost is calculated based on (1) cost representing fetal heart probability mesh values at each point of the estimated fetal heart rate over the particular time interval; and (2) cost representing the overall tortuosity of the estimated fetal heart rate over the particular time interval.

In some embodiments, instead of estimating the fetal heart rate over the particular time interval by calculating an estimation with minimal accumulated cost, the specifically programmed computer generates an estimated fetal heart rate over the particular time interval using the consolidated fetal hear rate estimations.

In some embodiments, estimating the fetal heart rate over the particular time interval is achieved by calculating an estimation with minimal accumulated cost, wherein, using dynamic programming, an accumulated cost mesh is constructed, where each value of the accumulated cost mesh is a sum of the fetal heart rate probability mesh value at that point and of the minimal path in its neighborhood in the previous step:

$$E(i,j)=e(i,j)+\min(E(i-1,j-k));k=-4:4$$

where:
e is the value of the fetal heart rate probability mesh.
E is the accumulated cost.
i represents time, j represents heart rate values in neighborhood of +/−4 [bpm/second].

Figure 52:
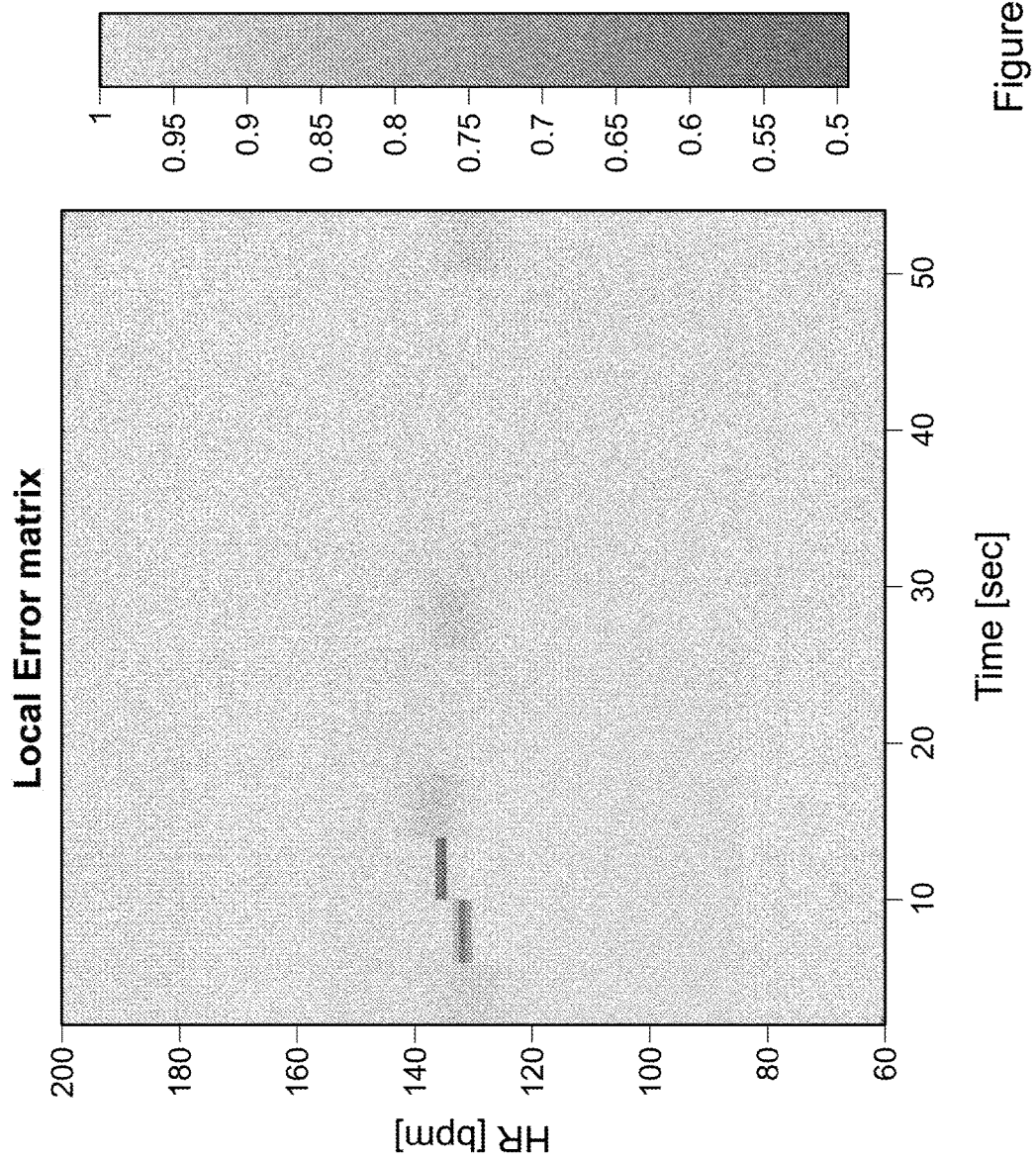
FIG. 52 shows a fetal heart rate estimation probability mesh according to some embodiments of the present invention.
Figure 53:
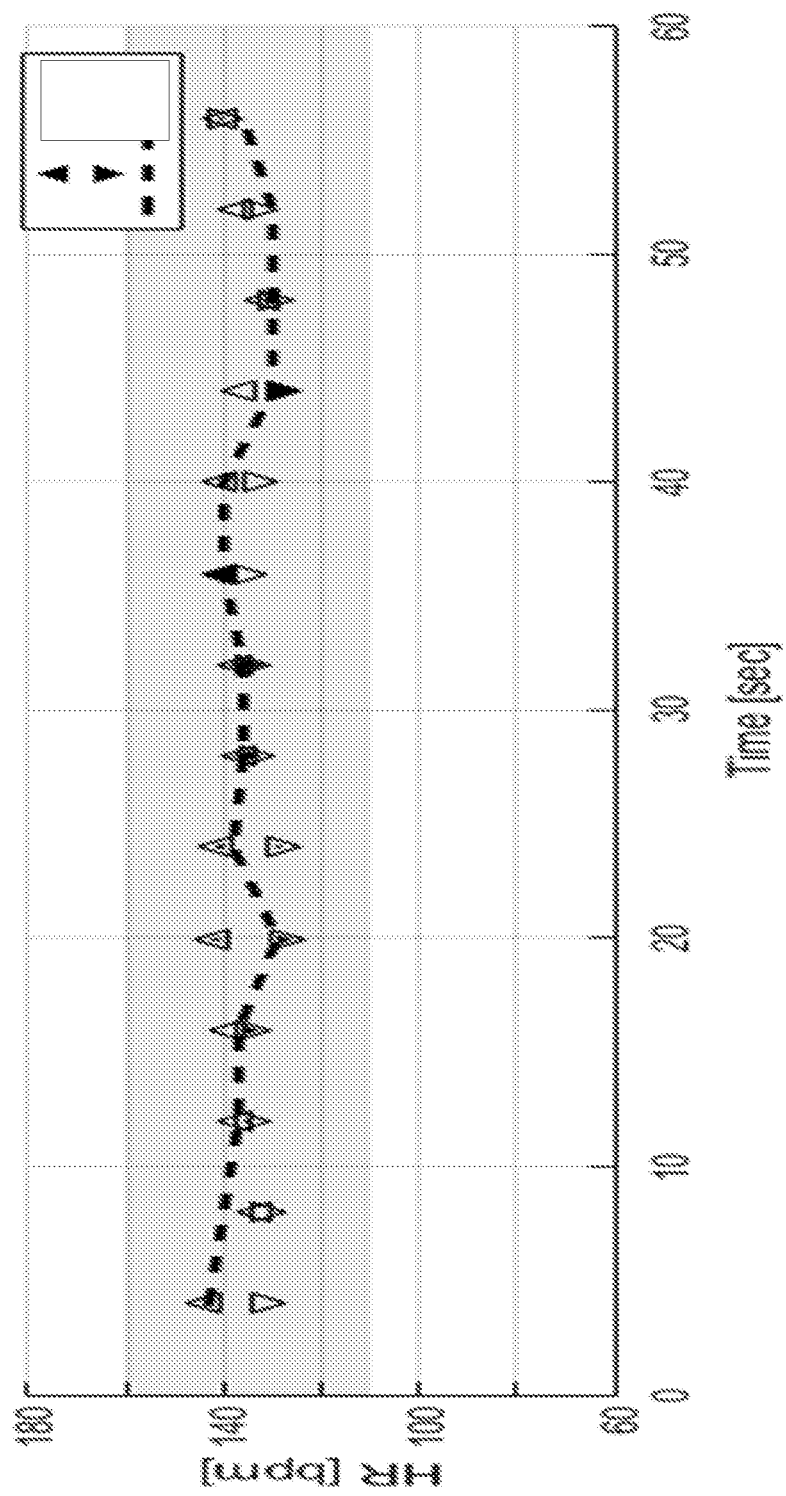
FIG. 53 shows an accumulated cost mesh built according to some embodiments of the present invention.
Figure 54:
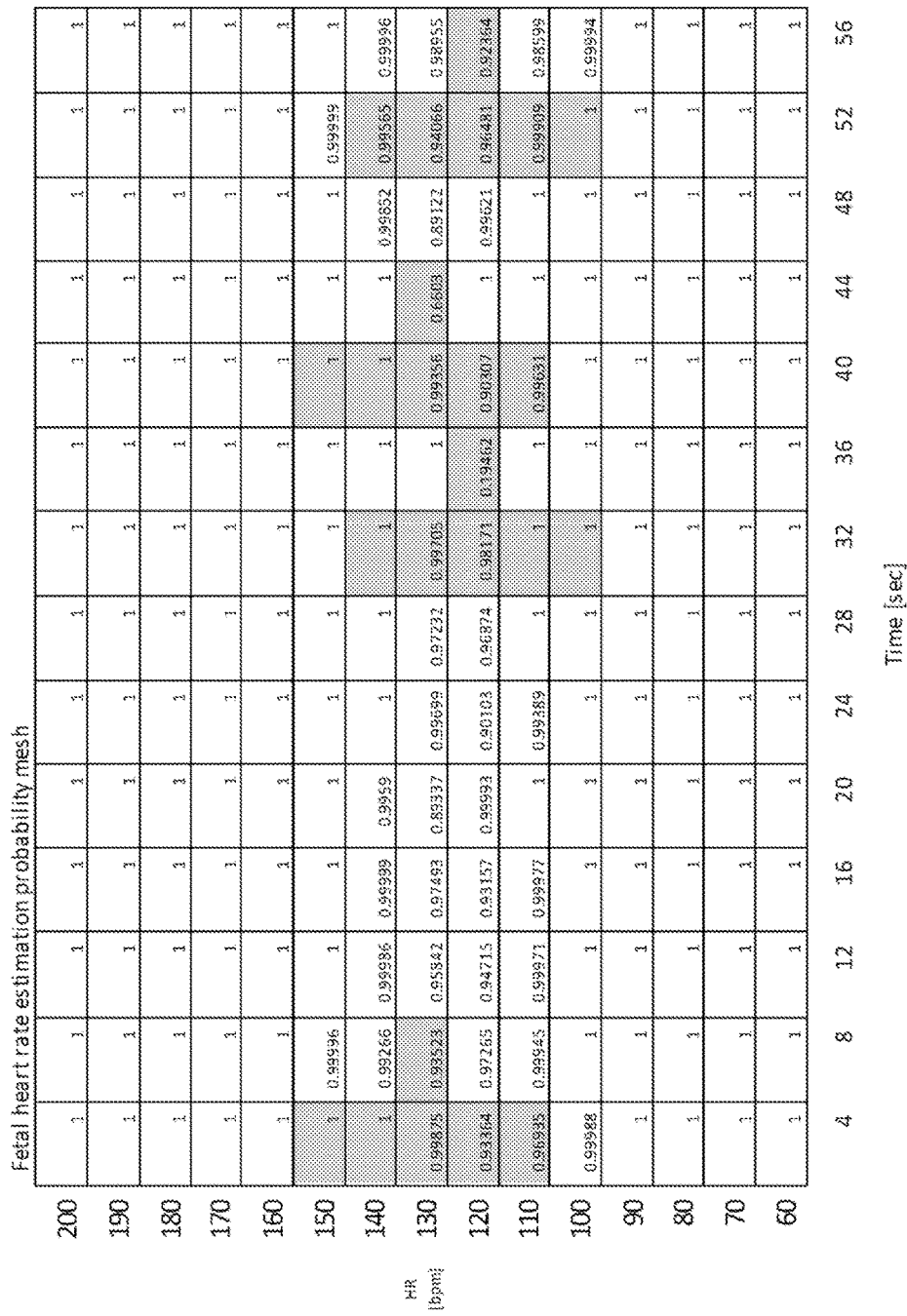
FIG. 54 shows fetal heart rate estimation probability mesh according to some embodiments of the present invention
Figure 55:
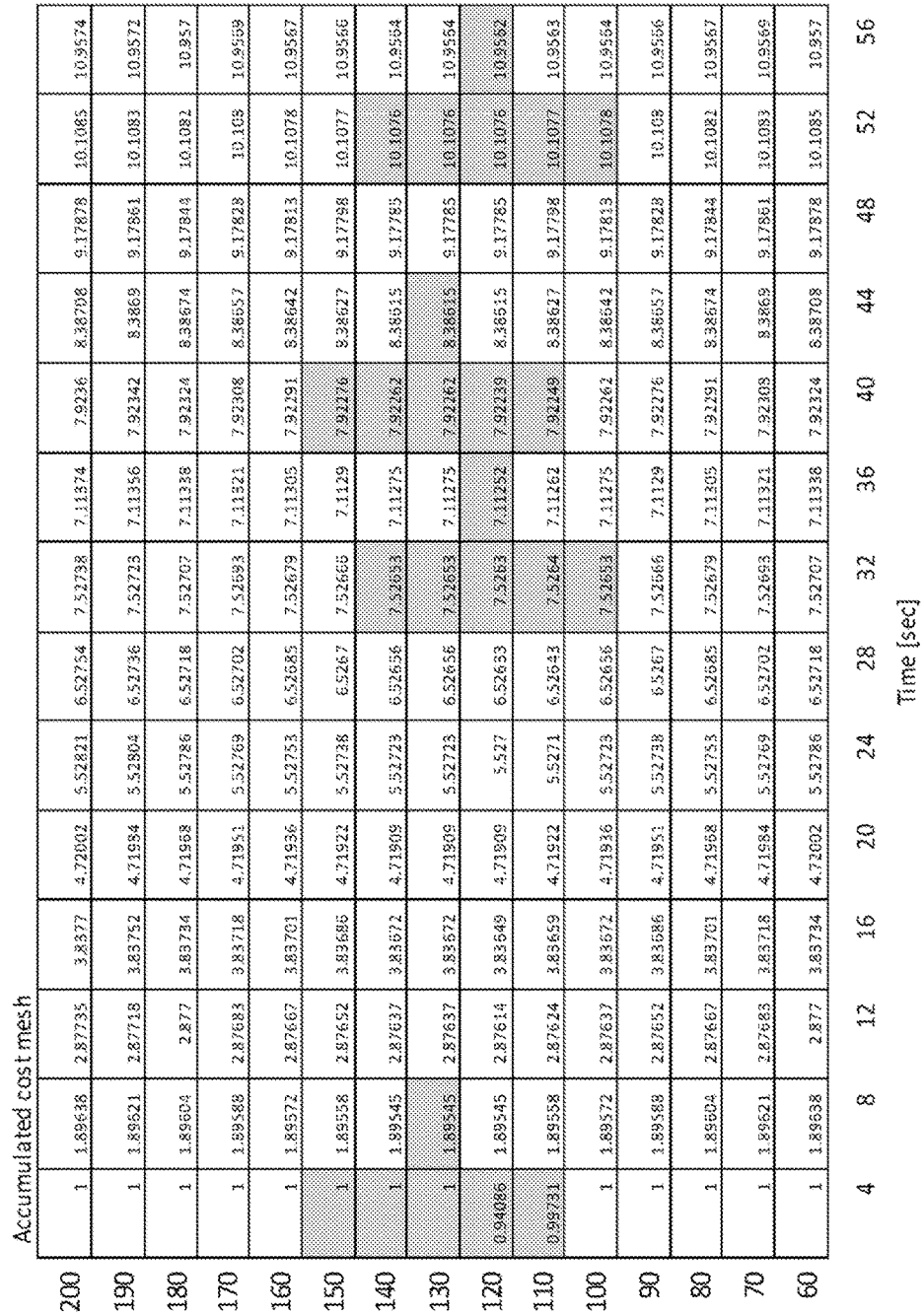
FIG. 55 shows an accumulated cost mesh according to some embodiments of the present invention.

FIGS. 52 and 53 show a fetal heart rate estimation probability mesh, and an accumulated cost mesh built from the fetal heart rate estimation probability mesh, respectively.

Referring to FIGS. 52 and 53 as an illustrative example, in some embodiments, the minimal path is found by finding the minimal value of all possible paths, which is, in the illustrative example, at the right column of the table, at Time=56 seconds. Minimal value is 10.9652, at HR=120 bpm. The minimal path is then selected by moving back in time, choosing the minimal value at each previous step in time in the range of +/−20 bpm/second, alternatively in the range of +/−10 bpm/second, alternatively in the range of +/−9 bpm/second, alternatively in the range of +/−8 bpm/second, alternatively in the range of +/−7 bpm/second, alternatively in the range of +/−6 bpm/second, alternatively in the range of +/−5 bpm/second, alternatively in the range of +/−4 bpm/second, alternatively in the range of +/−3 bpm/second, alternatively in the range of +/−2 bpm/second, alternatively in the range of +/−1 beats per minute.

In an alternate embodiment, the heart rate in the mesh range from 60-200 beats per minute, in 1 bpm increments.

Alternatively, the minimal path is computed using an exhaustive search, computing all possible paths in the fetal heart rate probability mesh.

Reference is now made to the following examples, which together with the above descriptions illustrate some embodiments of the invention in a non-limiting fashion.

EXAMPLES

Example 1: Electrodes According to Some Embodiments of the Present Invention

Various electrodes were manufactured according to the embodiment shown in FIG. 5 and evaluated. The following parameters were tested: the surface resistance/resistivity (MSSR); basic transfer function testing (BTFT); bio-parameters (PhysioPM); and real-life recordings of fetal cardiac electrical signals (RLPysioPM). Table 1 summarizes the electrodes tested.

TABLE 1

| Serial# | ID | Surface conductivity [Ohm/Sq] | Measured* Surface conductivity [Ohm/Sq] | Available size [cm × cm] | Materials | Notes |
|---|---|---|---|---|---|---|
| 1 | Orange_IT | <2 | 3.5 | 20 * 20 | Silver | Anisotropic, Stechable |
| 2 | C+ | <4 | 4 | 70 * 70 | Silver | Anisotropic, Stechable |
| 3 | Shaoxing17 | — | 0.3 | 1 m^2 | Silver | Isotropic, Non-strechable |
| 4 | Shaoxing27 | — | 0.6 | 1 m^2 | Silver | Isotropic, Non-strechable |
| 5 | Tech P130 + B | <5 | 1.1 | 40 * 40 | Silver | Isotropic, Strechable |
| 6 | Silver30 | — | 3.5 | 20 * 15 | Silver | Isotropic, Strechable |

FIG. 9 shows a micrograph of electrically conductive fabric used electrode serial no. 1. FIG. 10 shows a micrograph of electrically conductive fabric used electrode serial no. 2. FIG. 11 shows a micrograph of electrically conductive fabric used electrode serial no. 3. FIG. 12 shows a micrograph of electrically conductive fabric used electrode serial no. 4. FIG. 13 shows a micrograph of electrically conductive fabric used electrode serial no. 5. FIG. 14 shows a micrograph of electrically conductive fabric used electrode serial no. 6.

Table 2 a-f shows the MSSR values observed from the electrodes tested. Table 3 shows the observed anisotropy of the electrodes tested.

TABLE 2a

Sens 1

| Inject | Measure | Check? | M1 | M2 | M3 | AVG [Ω] | Aniso-tropic | Notes |
|---|---|---|---|---|---|---|---|---|
| AB | CD | 1 | 0.243 | 0.245 | 0.246 | 0.245 | 0.230 | |
| CD | AB | 1 | 0.228 | 0.227 | 0.226 | 0.227 | | |
| BA | DC | 1 | 0.224 | 0.225 | 0.222 | 0.224 | | |
| DC | BA | 1 | 0.227 | 0.224 | 0.222 | 0.224 | | |
| BC | DA | 1 | 0.489 | 0.487 | 0.484 | 0.487 | 0.459 | |
| DA | BC | 0 | 0 | 0 | 0 | 0.000 | | |
| CB | AD | 1 | 0.444 | 0.443 | 0.441 | 0.443 | | |
| AD | CB | 1 | 0.45 | 0.448 | 0.446 | 0.448 | | |

TABLE 2b

Sens 2

| Inject | Measure | Check? | M1 | M2 | M3 | AVG [Ω] | Aniso-tropic | Notes |
|---|---|---|---|---|---|---|---|---|
| AB | CD | 1 | 1.022 | 1.02 | 1.014 | 1.019 | 1.032 | |
| CD | AB | 1 | 0.999 | 0.996 | 0.995 | 0.997 | | |
| BA | DC | 1 | 0.994 | 0.984 | 0.979 | 0.986 | | |
| DC | BA | 1 | 1.13 | 1.123 | 1.123 | 1.125 | | |
| BC | DA | 0 | 0 | 0 | 0 | 0.000 | NaN | Main direction |
| DA | BC | 0 | 0 | 0 | 0 | 0.000 | | |
| CB | AD | 0 | 0 | 0 | 0 | 0.000 | | |
| AD | CB | 0 | 0 | 0 | 0 | 0.000 | | |

TABLE 2c

Sens 3

| Inject | Measure | Check? | M1 | M2 | M3 | AVG [Ω] | Iso-tropic | Notes |
|---|---|---|---|---|---|---|---|---|
| AB | CD | 1 | 0.039 | 0.038 | 0.04 | 0.039 | 0.031 | |
| CD | AB | 1 | 0.027 | 0.024 | 0.025 | 0.025 | | |
| BA | DC | 1 | 0.023 | 0.023 | 0.023 | 0.023 | | |
| DC | BA | 1 | 0.036 | 0.035 | 0.035 | 0.035 | | |
| BC | DA | 1 | 0.026 | 0.028 | 0.026 | 0.027 | 0.026 | |
| DA | BC | 1 | 0.024 | 0.025 | 0.023 | 0.024 | | |
| CB | AD | 1 | 0.027 | 0.026 | 0.026 | 0.026 | | |
| AD | CB | 1 | 0.027 | 0.024 | 0.026 | 0.026 | | |

TABLE 2d

Sens 4

| Inject | Measure | Check? | M1 | M2 | M3 | AVG [Ω] | Iso-tropic | Notes |
|---|---|---|---|---|---|---|---|---|
| AB | CD | 1 | 0.026 | 0.063 | 0.064 | 0.051 | 0.058 | |
| CD | AB | 1 | 0.058 | 0.057 | 0.059 | 0.058 | | |
| BA | DC | 1 | 0.06 | 0.059 | 0.058 | 0.059 | | |
| DC | BA | 1 | 0.066 | 0.065 | 0.066 | 0.066 | | |
| BC | DA | 1 | 0.045 | 0.045 | 0.045 | 0.045 | 0.044 | |
| DA | BC | 1 | 0.043 | 0.044 | 0.043 | 0.043 | | |
| CB | AD | 1 | 0.045 | 0.043 | 0.043 | 0.044 | | |
| AD | CB | 1 | 0.044 | 0.042 | 0.043 | 0.043 | | |

TABLE 2e

Sens 5

| Inject | Measure | Check? | M1 | M2 | M3 | AVG [Ω] | Aniso-tropic | Notes |
|---|---|---|---|---|---|---|---|---|
| AB | CD | 1 | 0.222 | 0.224 | 0.223 | 0.223 | 0.194 | |
| CD | AB | 1 | 0.212 | 0.211 | 0.213 | 0.212 | | |
| BA | DC | 1 | 0.22 | 0.219 | 0.222 | 0.220 | | |
| DC | BA | 1 | 0.233 | 0.065 | 0.066 | 0.121 | | |
| BC | DA | 1 | 0.074 | 0.073 | 0.073 | 0.073 | 0.075 | |
| DA | BC | 1 | 0.083 | 0.084 | 0.084 | 0.084 | | |
| CB | AD | 1 | 0.074 | 0.075 | 0.075 | 0.075 | | |
| AD | CB | 1 | 0.065 | 0.067 | 0.067 | 0.066 | | |

TABLE 2f

Sens 6

| Inject | Measure | Check? | M1 | M2 | M3 | AVG [Ω] | Aniso-tropic | Notes |
|---|---|---|---|---|---|---|---|---|
| AB | CD | 1 | 0.05 | 0.048 | 0.049 | 0.049 | 0.046 | |
| CD | AB | 1 | 0.038 | 0.039 | 0.037 | 0.038 | | |
| BA | DC | 1 | 0.055 | 0.057 | 0.056 | 0.056 | | |
| DC | BA | 1 | 0.043 | 0.041 | 0.042 | 0.042 | | |
| BC | DA | 1 | 0.911 | 0.903 | 0.898 | 0.904 | 0.898 | |
| DA | BC | 1 | 0.904 | 0.891 | 0.897 | 0.897 | | |
| CB | AD | 1 | 0.885 | 0.886 | 0.882 | 0.884 | | |
| AD | CB | 1 | 0.903 | 0.903 | 0.908 | 0.905 | | |

TABLE 3

| ID | Main direction | 2nd direction | Anisotropy |
|---|---|---|---|
| 1 | 0.230 | 0.459 | 50% |
| 2 | 0.000* | 1.032 | 100% |
| 3 | 0.026 | 0.031 | 16% |
| 4 | 0.044 | 0.058 | 25% |
| 5 | 0.075 | 0.194 | 62% |
| 6 | 0.046 | 0.898 | 95% |

The impedance between the fabric and the lead connector was also determined. The electrodes were connected to a copper sheet, and a pressure of 34.386 kPa was applied, using a 1.01026 kg weight. The measured impedance of the measuring system was 0.109Ω, and this value was subtracted from the measured impedance of the electrodes. The results are shown in Table 4. Electrode serial no. 5 was observed to have the greatest surface area in contact with the skin.

TABLE 4

| ID | Check? | M1 | M2 | M3 | AVG [Ω] | Value [Ω] |
|---|---|---|---|---|---|---|
| 1 | 1 | 0.694 | 0.685 | 0.682 | 0.687 | 0.578 |
| 2 | 1 | 0.461 | 0.460 | 0.452 | 0.458 | 0.349 |
| 3 | 1 | 0.206 | 0.205 | 0.206 | 0.206 | 0.097 |
| 4 | 1 | 0.271 | 0.269 | 0.268 | 0.269 | 0.160 |
| 5 | 1 | 0.309 | 0.307 | 0.308 | 0.308 | 0.199 |
| 6 | 1 | 0.709 | 0.662 | 0.664 | 0.678 | 0.569 |

Electrodes 3-5 performed best. Performance was scored as follows:

| Req. ID | Category | Test Category | Details |
|---|---|---|---|
| 0.1 | Performance | General | Record ECG signals |
| 1.1 | Performance | MSRR | Surface resistivity below 1 [Ω · m] |

-continued

| Req.<br>ID Category | Test Category | Details |
|---|---|---|
| 1.2 Performance | MSRR | Surface resistance below 1 [Ω/sq] |
| 2.1 Performance | BTFT | SINAD is higher than 50 dB |
| 2.2 Performance | BTFT | SNR is higher than 50 dB |
| 2.3 Performance | BTFT | CORR COEF higher than 0.95 |
| 3.1 Performance | PysioPM | Skin-Sensor impedance below 0.15 [MΩ] |
| 3.2 Performance | PysioPM | Self-noise of the sensor below 0.1 µV |
| 3.3 Performance | PysioPM | Immunity to motion artifacts |
| 3.4 Performance | PysioPM | Power-line noise rejection higher than 80 dB |
| 4.1 Performance | RLPysioPM | Fetal ECG is visible in more than 1 record |
| 4.2 Performance | RLPysioPM | Fetal ECG SNR is higher than 1 dB |
| 3.5 Performance | RLPysioPM | Relative fetal ECG SNR (relative to the reference sensors) is higher than 0.85 |

A summary of the MSSR results for electrodes 3-5 is shown in Table 5. The fabric of electrode serial no. 6 was weak, and has large voids between the fibers (see FIG. 14) and was therefore unsuitable. Electrode serial no. 2 was excluded because the surface resistivity was greater than 1 Ω/square.

TABLE 5

| | Surface resistance | | | | |
|---|---|---|---|---|---|
| ID | Main direction | 2nd direction | Anisotropy | S2C | Notes |
| 3 | 0.026 | 0.031 | 0.163 | 0.097 | Lowest resistance, non-stretchable, Isotropic |
| 4 | 0.044 | 0.058 | 0.251 | 0.160 | Mid |
| 5 | 0.075 | 0.194 | 0.616 | 0.199 | Low resistance, Highest Anisotropy, highly stretchable |

BTFT Results:

BTFT measurements were obtained using the methods described in Example 3 below. Table 6 shows the results.

TABLE 6

| ID | CORRCOEF | CORRLAG | Relative diff RMS [%] | SINAD | | | | SNR | | |
|---|---|---|---|---|---|---|---|---|---|---|
| | | | | Input | Output | Rel | RelRef | input | Output | Rel |
| Ref | 1 | 0 | 0.012 | 48.545 | 48.541 | 0.008% | 0.000% | 53.852 | 53.836 | 0.029% |
| 1 | 1 | 0 | 0.010 | 47.964 | 47.956 | 0.015% | 1.205% | 54.278 | 54.242 | 0.066% |
| 2 | 1 | 0 | 0.016 | 48.088 | 48.077 | 0.021% | 0.955% | 54.173 | 54.136 | 0.068% |
| 3 | 1 | 0 | 0.010 | 48.231 | 48.222 | 0.018% | 0.657% | 54.197 | 54.161 | 0.067% |
| 4 | 1 | 0 | 0.015 | 48.303 | 48.293 | 0.020% | 0.511% | 54.042 | 54.006 | 0.066% |
| 5 | 1 | 0 | 0.015 | 48.527 | 48.517 | 0.020% | 0.049% | 54.137 | 54.102 | 0.064% |
| 6 | 1 | 0 | 0.014 | 48.606 | 48.597 | 0.018% | 0.115% | 54.113 | 54.073 | 0.074% |

CORRCOEF: is the linear correlation coefficient between the input and the output signals; CORRLAG: is the lag between the input and output signals; Relative diff RMS: is the relative difference in the RMS of the input and output signals in %; SINAD.Rel: is the relative percentage difference in the SINAD values between the input and the output signals; SINAD.RelRef: is the relative percentage difference in the signal to noise and distortion ratio (SINAD) values between the output signal and the reference signal; SNR.Rel: is the relative percentage difference in the SNR values between the input and the output signals. The BTFT results show that the electrodes that have the best performance in terms of SNR and relative SINAD is electrode serial no. 5 followed by electrode serial no. 4, then electrode serial no. 3.

PysioPM:

PysioPM measurements were obtained according to the methods described in Example 4. Table 7 shows the results of the measured impedance.

TABLE 7

| ID | Sens1 | Sens2 | Sens3 | Sens4 | MAXDIFF |
|---|---|---|---|---|---|
| 3 | 0.733 | 0.667 | 0.651 | 0.754 | 13.66% |
| 4 | 1.396 | 1.495 | 1.281 | 1.503 | 14.77% |
| 5 | 4.251 | 3.1 | 3.551 | 3.921 | 27.08% |

The values observed include the resistance of a 5 cm lead wire, the copper sheet, and a cable connected to the copper sheet.

Impedance of the Interface Between the Electrode and the Skin:

The impedance was measured between 2 electrodes placed on skin 20 mm apart. Table 8 shows the average of 3 experiments.

TABLE 8

| ID | Average Bioimpedance [MΩ] |
|---|---|
| 3 | 0.602 |
| 4 | 0.227 |
| 5 | 0.135 |

Recorded ECG Signals Data Using the Electrodes:

FIG. 14, panels a-c show recorded ECG signals data using electrode serial nos. 3-5 respectively. Electrodes 3-5 were able to filter out powerline noise, and had similar amplitudes. However, all electrodes were susceptible to movement artifacts.

Figure 16:
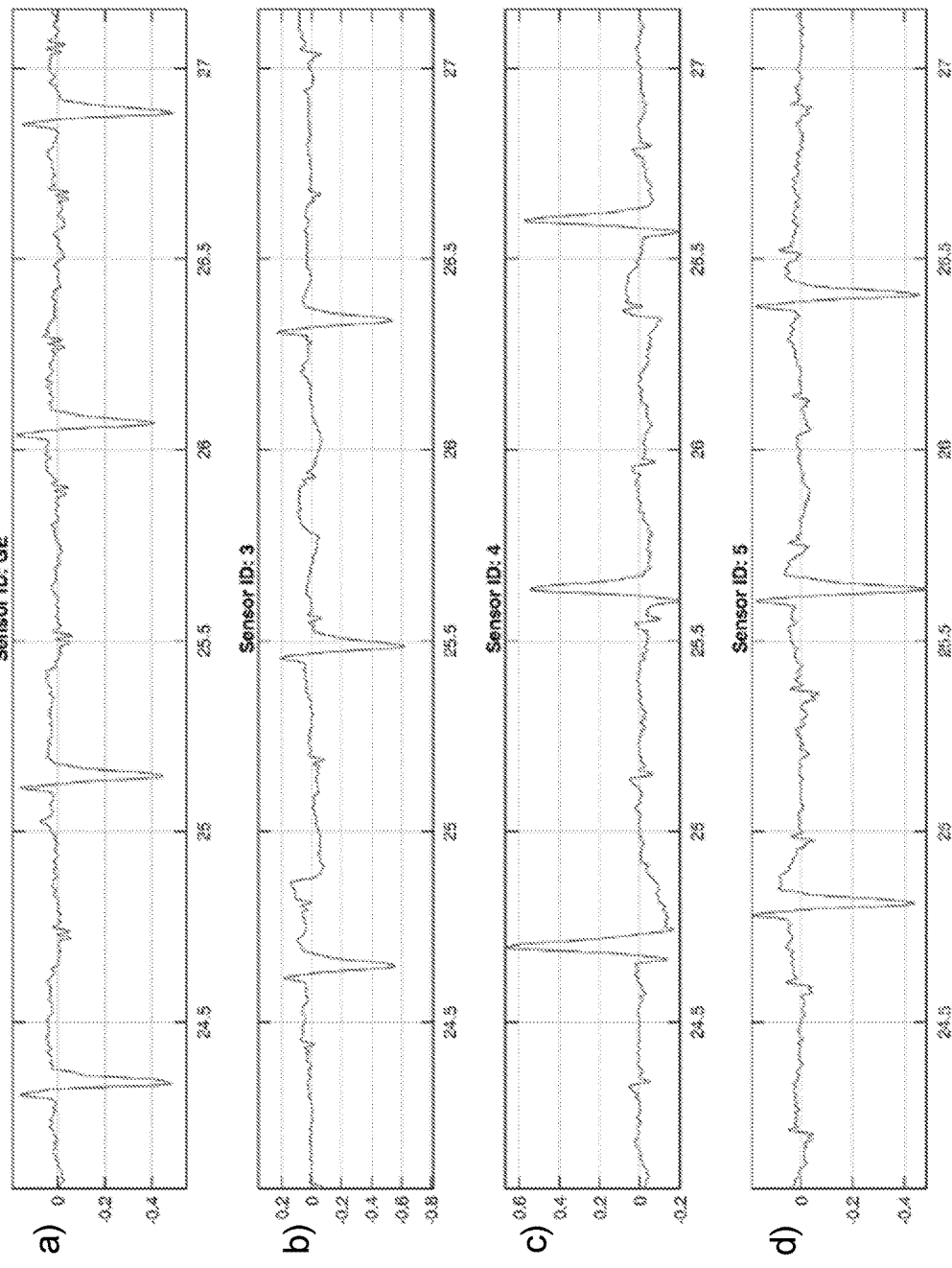
FIG. 16, panels a-d, show the recorded ECG signals data using electrode serial nos. 3-5, and a control wet gel ECG electrode (GE Healthcare), respectively at 25 weeks from a pregnant human subject.
Figure 17:
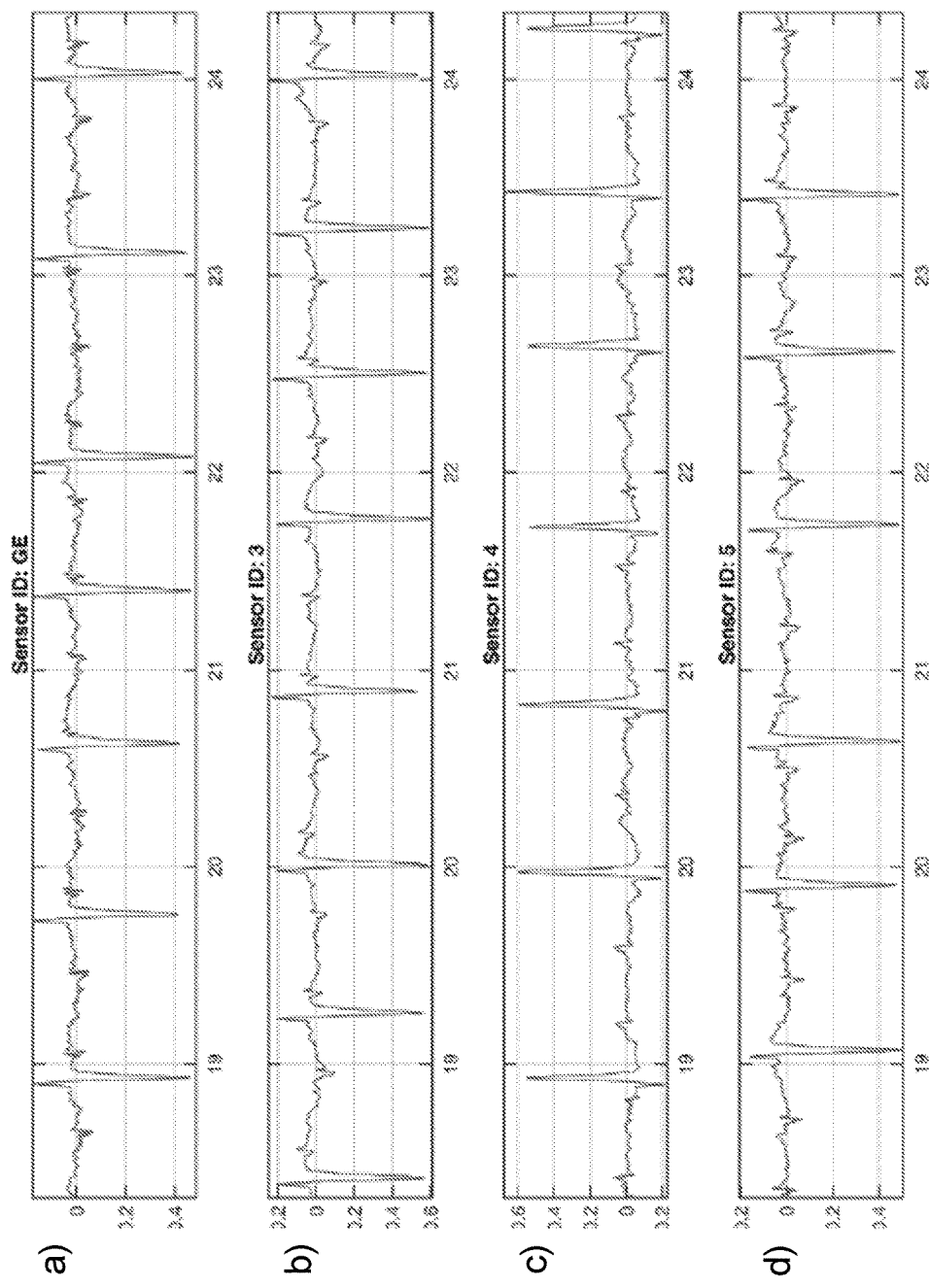
FIG. 17, panels a-d, show the recorded ECG signals data using electrode serial nos. 3-5, and a control wet gel ECG electrode (GE), respectively at 25 weeks from a pregnant human subject.

ECG signal were recorded from two pregnant subjects at week 25 and week 28, using either electrodes 3, 4, 5, and a comparison electrode, using a wet contact electrode, using the electrode position B1-B3 (see FIG. 29 for the electrode position). FIG. 16, panels a-d, and FIG. 17, panels a-d show the recorded ECG signals data using electrode serial nos. 3-5, and the GE comparison electrode respectively at 25 weeks in the two subjects. Fetal ECG were visible in the traces.

Example 2: Measuring Surface Resistivity and Resistance

Figure 18:
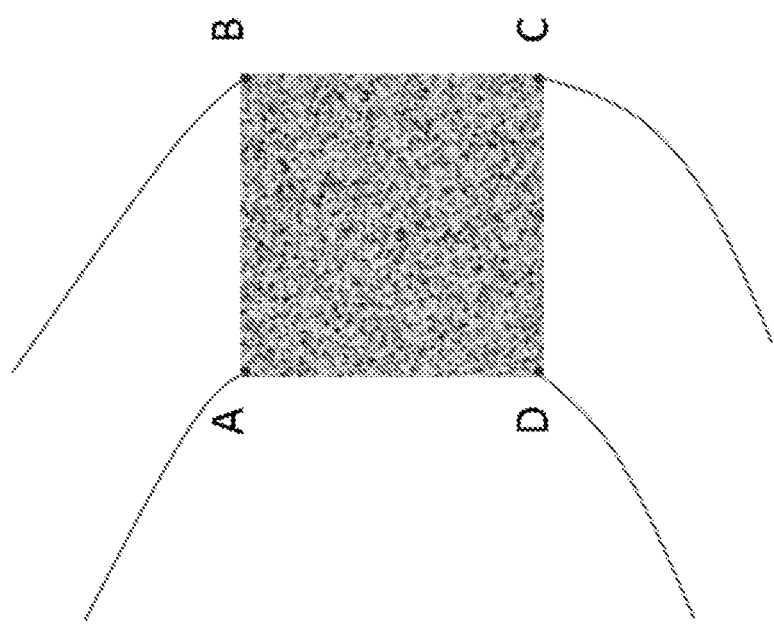
FIG. 18 shows an experimental set up to determine surface resistivity and resistance of an electrically conductive fabric according to some embodiments of the present invention.

FIG. 18 shows an experimental set up to determine surface resistivity and resistance of an electrically conductive fabric according to some embodiments of the present invention. A, B, C, and D are point contact connectors. To measure surface resistivity, current was introduced and recorded according to the following protocol:
1. Connect the sample as described in the background section.
2. Make sure that the current source is running and stable.
3. Inject AB, measure CD;
4. Inject CD, measure AB;
5. Inject BA, measure DC;
6. Inject DC, measure BA;
7. Inject BC, measure DA;
8. Inject DA, measure BC;
9. Inject CB, measure AD;
10. Inject AD, measure CB;

Surface resistance was calculated according to the following:

$$\exp\left(-\frac{\pi R_{AB,CD}}{R_s}\right) + \exp\left(-\frac{\pi R_{BC,AD}}{R_s}\right) = 1$$

where $$R_{AB,CD}[\Omega] = \frac{V_{DC}}{i_{AB}} = \frac{V_D - V_C}{i_{AB}}$$

is the resistance measured between C and D while introducing current between points A and B; and $i_{AB}[A]$ is the injected current between points A and B; and d [m] is the thickness of the sample; and ρ is the resistivity.

$$\rho = R_s d [\Omega \cdot m]$$
$$R_s = \frac{\pi}{\ln 2} \cdot R$$
$$R = R_{vertical} = R_{horizontal}$$
$$R_{vertical} = \frac{(R_{AB,CD} + R_{CD,AB} + R_{BA,DC} + R_{DC,BA})}{2}$$
$$R_{horizontal} = \frac{(R_{BC,DA} + R_{DA,BC} + R_{CB,AD} + R_{AD,CB})}{2}$$

The above protocol was performed using an electrode alone, or an electrode contacting a copper sheet (to measure the resistivity of the electrode-surface interface). Additionally, measurements were obtained after the electrically conductive fabric was stretched either 20%, or 50% in the man direction, or in the direction perpendicular to the main direction.

Example 3: Basic Transfer Function Testing

Figure 19:
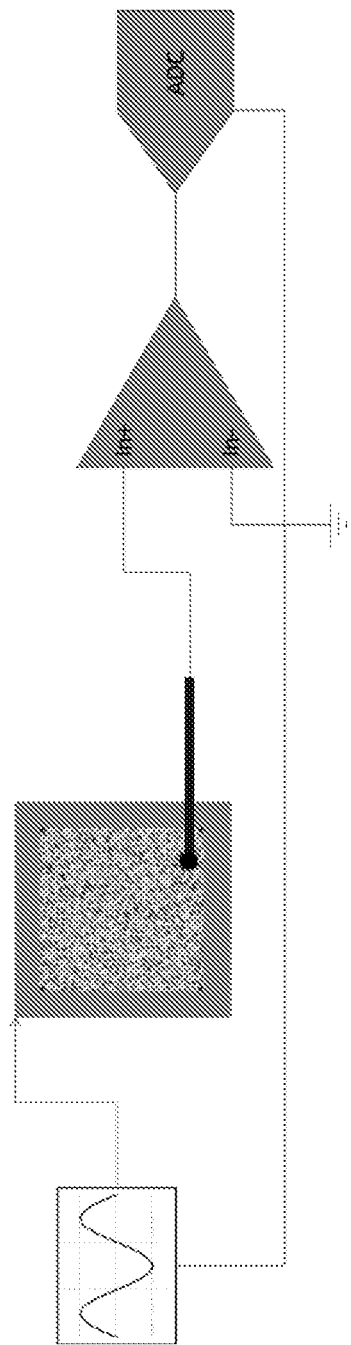
FIG. 19 shows an experimental set up to determine BTFT of an electrically conductive fabric according to some embodiments of the present invention.

An electrode was placed on a copper sheet, such that the cutaneous contact is in contact with the copper sheet, and a 1 kg mass was applied to the electrode. The copper sheet was connected to the positive terminal of a signal generator, the electrode was connected to the positive input of an amplifier, and the other input of the amplifier was connected to ground. FIG. 19 shows the experimental setup described above. A 30 Hz signal was generated by the signal amplifier, and the following parameters were recorded:
1. Time domain:
   a. amplitude-2-amplitude; and
   b. non-zero division; and
   c. time shifts; and
   d. cross correlation; and
   e. correlation coefficient; and
   f. Histogram: Mean, RMS, STD.
2. Frequency domain:
   a. Welch PSD estimation (magnitude); and
   b. Cross coherence; and
   c. Main frequency magnitude; and
   d. Dominant frequencies magnitude; and
   e. SINAD, SNR.

Example 4: Electrophysiological Performance Measurements

The source of the physiological signals detected using the electrodes according to some embodiments of the present invention are located within the body of the pregnant human subject and have extremely low amplitude and low frequency. Without intending to be limited by any particular theory, the physiological signals flow within the body of the pregnant human subject by the movement of ions. The electrodes according to some embodiments of the present invention act as signal transducers, and transduce the movement of ions to the movements of electrons. The skin-electrode interface (SSI) is one determining factor of the electrode's ability to transduce the physiological signals.

Figure 20:
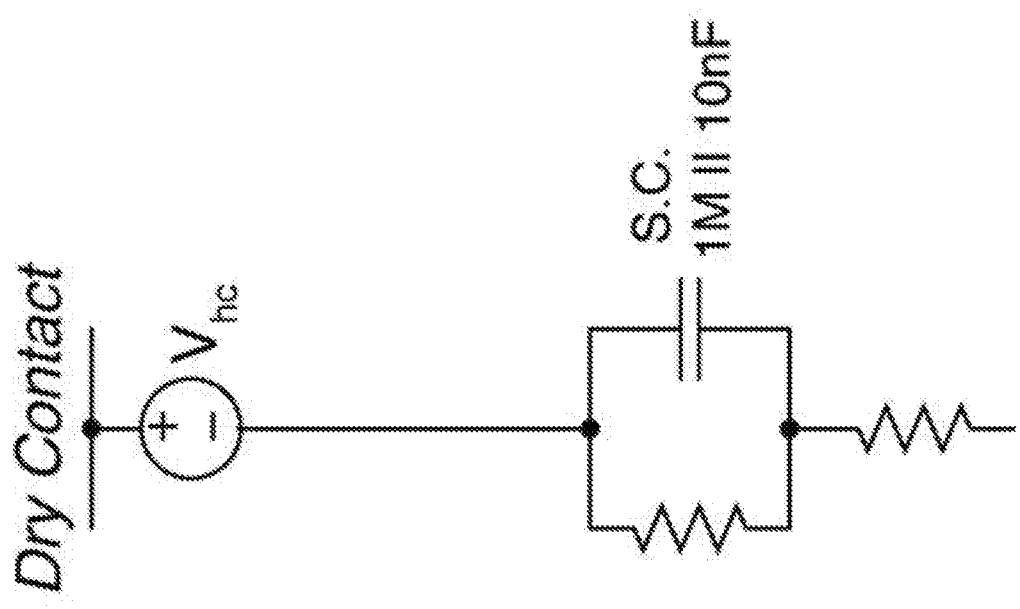
FIG. 20 shows a diagram if a skin-electrode interface equivalent circuit according to some embodiments of the present invention.

The SSI for the electrodes according to some embodiments of the present invention may be modeled by a parallel circuit of an ohmic and capacitive impedance with an additional Warburg resistance (see FIG. 20). Without intending to be limited to any particular theory, both the conductive and the capacitive compartments affect the performance of an electrode according to some embodiments of the present invention. The skin-electrode impedance (SSiM) is equivalent to the impedance of the circuit shown in FIG. 20, and ranges from 10 kΩ to 100 MΩ. Decreasing the impedance improves the performance of an electrode according to some embodiments of the present invention. Decreasing impedance may be achieved by increasing the surface areas of the cutaneous contact, or by reducing the resistivity of the cuntaneous contact. An increase in input impedance and a decrease in input capacitance of the amplifier may also improves the performance of an electrode according to some embodiments of the present invention.

Figure 21:
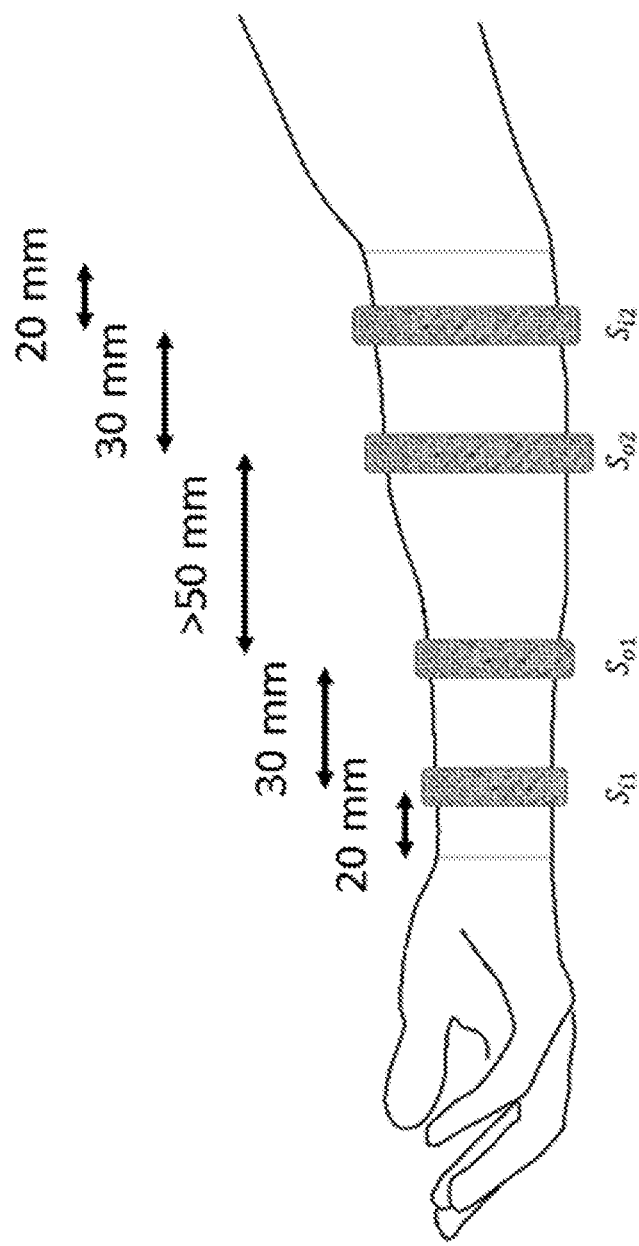
FIG. 21 shows a representation of a test electrode configuration.

In the test protocol, electrodes were applied to the skin of a subject's hand, according to the arrangement shown in FIG. 21. The surface of the hand having first been cleaned. Four VELCRO straps were applied, the pressure of the straps was confirmed to be equal, using a surface pressure sensor. Test electrodes were then inserted under the straps. The pressure that the electrodes contact the skin was confirmed to be equal, using a surface pressure sensor. Impedance was measured as follows:
  2-wire: measure the 2wire resistance between the $S_i$ electrodes and the $S_o$ electrodes (2 measurements).
  4-wire: use the $S_i$ electrodes as the injectors and the $S_o$ electrodes as the measurers. Measure the resistance (1 measurement).
  Capacitance measurement: measure the 2wire capacitance between the $S_i$ electrodes and the $S_o$ electrodes (2 measurements).

A 150 $mV_{pp}$ sine wave was applied to the $S_i$ electrodes, and the voltage developed at the $S_o$ electrodes was recorded using a BioPac amplifier. Recordings were obtained using a sine wave of the following frequencies: 0.1, 1, 5, 10, 15, 20, 25, 30, 35, 40, 45, 50, 55, 60, 70, 80, 90, Hz.

Example 4: Algorithm Design According to Some Embodiments of the Present Invention

TABLE 9

5. Low Level Design of the algorithm: The fECG detection algorithm have the following LLD:
   5.1. The acquired N-channels signals should be preprocessed:
      5.1.1. Signal exclusion: Saturated signals are excluded in this version (if the saturated part exceeds 10% of the overall length of the signal). For the next versions, this criterion should be replaced by an online examiner.
      5.1.2. Baseline removal: the baseline of the ECG signal needs to be removed. It can be removed using a number of methods. In the algorithm the baseline is removed using a moving average filter with an order of 501 (milliseconds).
      5.1.3. Low pass filtering with an IIR filter (auto designed by Matlab):
         5.1.3.1. Type: Chebyshev Type I
         5.1.3.2. Cutoff freq: 70 Hz
         5.1.3.3. Baseband ripple: 0.12 dB
         5.1.3.4. Order: 12th order, 6 sections
      5.1.4. Power line interference cancelation: to be in the safe side and for simplicity purposes, the following filter is used:
         5.1.4.1. Type: Butterworth (band-stop)
         5.1.4.2. Cutoff freq: 49.5-50.5 Hz
         5.1.4.3. Order: 10th order, 5 sections
   5.2. Maternal ECG detection: The following steps are performed:
      5.2.1. Examination: the data is passed through an additional high pass filter (5th order @1 Hz). The data is examined by preliminary and simple peak detector. The relative energy of the peaks is calculated (relative to the overall energy of the signal). Each signal is given a quality score depending on this measure. Signals with a quality score of less than a threshold are excluded. In addition, the signals are examined for missing data and NaNs.
      5.2.2. Peak enhancement: The preprocessed ECG data is passed through an additional median filter with an order of 100 samples to enhance the maternal peaks.
      5.2.3. Peaks detection: for each signal:
         5.2.3.1. Divide the signal into 10 seconds segments, for each segment:

TABLE 10

5.2.3.2. Normalize the data
5.2.3.3. Find the local peaks in the segment using derivative, thresholding and minimum distances methods
5.2.3.4. After finishing with all of the segments perform kmedoids clustering on the number of peaks in each segments:
5.2.3.4.1. For segments with very low number of peaks, (apparently there is a noise spike) perform AGC on the data and redetect the peaks. If the new number of peaks belongs to one of the good clusters, add these peaks. If not, ignore these peaks
5.2.3.4.2. For segments with very high number of peaks (due to high noise most probably), ignore these peaks
5.2.3.5. After finishing, perform kmedoids clustering on the amplitudes of the peaks, very low peaks and very high peaks are filtered using this step.
5.2.3.6. After finishing with the signal, do the following:
5.2.3.6.1. Check that the number of peaks falls into an expected interval (based on the maximum and minimum possible heart rates)
5.2.3.6.2. Is step 1 is passed, check that the relative energy of the QRS complexes is higher than a threshold
5.2.3.6.3. If step 2 is passed, perform peak redetection using the cross correlation method (helps removing false positive and adding false negatives)
5.2.4. Peak re-detection: if the previous step is failed to detect the peaks in at least one channel, apply ICA to the
data and then repeat step (5.2.3)
5.2.5. Peaks examination:
5.2.5.1. A score is given for each one of the N signals. The best lead is defined as the lead with the biggest score
5.2.5.2. A global peak array is constructed based on the best lead with corrections made using the peaks from the other leads

TABLE 11

5.5.5.3. The global peaks array is examined using physiological measures (RR intervals, HR, HRV)
5.2.6. HRC calculation: the mHRC is calculated using the detected maternal R-waves
5.3. Maternal ECG Elimination: The purpose of this step is to eliminate the maternal ECG and thereafter stay with the fetal ECG signals and some noise according to the model that have been previously developed. The following steps are performed for each of the N-channels:
5.3.1. Resample the signal to match a 4kSPS sampling frequency
5.3.2. Find the QRS onset and offset positions using the Curve Length Transform (CLT)
5.3.3. For each one of the detected maternal peaks:
5.3.3.1. Define a beat interval: the beat interval is defined as, except for the first and last peaks, (1) beat onset: half the distance between the current peak and the previous peak and (2) beat offset: half the distance between the current peak and the next peak. Due to the beat-2-beat changing heart rate, the beat interval should change for each beat
5.3.3.2. Define a local template, a template that depends on the current beat:

TABLE 11-continued 5.3.3.2.1. Step 1: Search for at least 10 beats that have a correlation coefficient (obtained from cross correlation) of at least 0.98 This step is usually fast and gives results for not-noisy signals
5.3.3.2.2. Step 2: Step 1 usually fails for noisy signals hence an iterative scheme is used:
5.3.3.2.2.1. Define the template as the beat itself
5.3.3.2.2.2. An initial correlation coefficient is defined (high value threshold: 0.99)
5.3.3.2.2.3. Search for the beats that are very similar to the current beat (have higher correlation than the threshold)
5.3.3.2.2.4. If none is found, decrease the correlation threshold and repeat

TABLE 12

5.3.3.2.2.5. If some is found, update the template and continue
5.3.3.2.2.6. The procedure is terminated if: (1) a maximum number of iterations is reached, (2) the number of beats to include reached a minimum number or (3) the current iteration yields the same results as the previous iteration
5.3.3.2.3. A byproduct of this process is a score for how noisy each beat is
5.3.4. Start the adaptation procedure, iterative Levenberg-Marquardt Parametric Optimization (LMPO) for solving non-linear damped least squares problems. Divide the beat into 3 parts: (1) P-wave region, (2) QRS complex and (3) T-wave region. The iterative procedure:
5.3.4.1. Initialize the LMA algorithm (Algorithm params)
5.3.4.2. Perform initial guess for the mECG (first guess is the template, let it be $\phi\_c$)
5.3.4.3. Adapt the initial guess
5.3.4.4. Compare the result to the measured current ECG (current beat with maternal data, fetal data and noise, let it be $\phi\_m$)
5.3.4.5. Check if a termination criteria is reached, if yes terminate returning the last good result
5.3.4.6. If not, update the algorithm parameters and repeat steps 3-5.
5.3.4.7. This algorithm has the following characteristics:
    It interpolates between Gauss - Newton (GN) method and the Gradient Decent (GD) method taking the good form both
    At first, it convergence very fast due to the fast convergence of GD. When it advances, the steps become smaller, yielding a slow convergence when it is close to the local minimum (Slow yet cautious progress near the minimum!)

TABLE 13

It operates by the principle of "worst case scenario is to stay the same"
The only problem with this iterative algorithm is the convergence to local minima. This isn't a big issue in our case since we know that the local minima is also, always, the global one (due to the educated guess of the start conditions)
The algorithm minimizes the error energy function defined as the l2 norm of the difference between the calculated potentials and the measured potentials: $E = ||\phi\_c - \phi\_m||^2$
The final result of the algorithm is a stable, global and reproducible solution due to the fact the number of parameters to be reconstructed is way smaller than the number of the available observations
The reconstruction parameters of the algorithm are:
P region multiplier
QRS region multiplier
T region multiplier
Beat shift

TABLE 14

5.3.5. Construct the maternal ECG (mECG) array (started form the templates for each beat and get close to the current channel measured ECG)
5.3.6. Construct the fetal ECG array, fECG = ECG − mECG
5.3.7. Downsample the mECG and the fECG signals to match the initial sampling rate
5.4. Fetal ECG preprocessing: After the elimination (near-perfect elimination) of the mECG, the remaining data is processed for fECG enhancement (see the next step for more info). A preliminary prediction of the best fetal channel is performed depending on the energy distribution of the auto correlation function of the signal
5.5. Fetal ECG detection:
5.5.1. First step is to prepare the data. Usually, the fetal signals do not appear in all of the channels hence it is better to decrease the dimension of the data. This is done by:
5.5.2. Apply Singular Value Decomposition (SVD) keeping only the N-1 singular values and vectors
5.5.3. Apply fastICA to the resulting data (with 'tanh')
5.5.4. Apply peak-2-mean transformation:
5.5.4.1. Use a moving window to calculate the relation: max(signal[win])/mean(signal[win]) (enhances peaks)
5.5.4.2. Calculate the 1st derivative of the result of step 1
5.5.4.3. Find the zero crossing to find peaks, take the negative part of the derivative
5.5.4.4. Find the peaks in the previous result and cluster them based on the difference between them. Identify the best group as the group with the maximum score: SCR = n/RMS where n is the number of peaks in each cluster and RMS is the energy of the derivative of the distance between the peaks
  5.5.4.5. Perform a prediction for the RR interval for the best group
5.5.4.6. If the prediction doesn't fit the real model, ignore this channel

TABLE 15

5.5.4.7. If so, calculate the auto correlation function of a windowed RMS of the signal, if the result have a narrow distribution ignore this channel, else:

TABLE 15-continued 5.5.4.8. Apply AGC to the negative derivative signal
5.5.4.9. Normalize the result, and flag it as the processing data
5.5.4.10.Repeat steps 1-10 to the N-channels
5.5.5. Try to perform fetal peak detection using the same methodology as for the maternal peak detection with different parameters
5.5.6. If the previous step is successful, skip this step. If not, this means that the fetal data is noisy. In this case perform the following preprocessing:
5.5.6.1. The fetal data is band-pass filtered between the range 15-70 Hz
5.5.6.2. Wavelet denoising is applied to the data
5.5.6.3. Windowed RMS is applied on the data
5.5.6.4. The results are low pass filtered @35 Hz
5.5.6.5. The data is normalized and AGC is applied to the data
5.5.7. Following step (5.5.6), perform fetal peak detection without the correlation part
5.5.8. Following step (5.5.7), if more than one channel is valid, calculate the kurtosis of the distribution of the distances between the peaks. The best lead is defined as the peak with the maximum relative kurtosis
5.5.9. Following step (5.5.8), perform peak redetection using the RR intervals. Also try to build, using a Kalman filter, an array of the positions of the peaks
5.5.10. Following step (5.5.5/5.5.9), perform fetal peak examination using the information about the RR intervals
5.5.11. Following step (5.5.10), build the fetal peaks array:
5.5.11.1.Time varying RR interval is extracted from the results
5.5.11.2.A characteristic region in the previous signal is defined: a region in which the RR interval curve is very smooth (which means that there is minimum falses in this region)-this region is called the seed region
5.5.11.3.Perform region growing staring from the seed points while including only points that are close to the local RR interval

TABLE 16

5.5.12.Perform peak examination and correction:
5.5.12.1. Stage 1: find false negatives and Zigzags (caused by two consecutive, opposite misdetections)
5.5.12.2. Stage 2: Find mis-positioning of the peaks by detecting spikes in the updating RR curve Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A system for monitoring maternal and fetal cardiac activity comprising:
 a. at least one electrocardiogram sensor configured to contact skin of an abdomen of a pregnant human subject and detect fetal and maternal cardiac electrical activity;
 b. at least one acoustic sensor configured to contact the skin of the abdomen of the pregnant human subject and detect the fetal and maternal cardiac electrical activity;
 c. a garment configured to position the at least one electrocardiogram sensor and the at least one acoustic sensor on the abdomen of the pregnant human subject;
 d. at least one first specialized computer machine, comprising: a first non-transient memory, electronically storing first particular computer executable program code; and at least one first computer processor which, when executing the first particular program code, becomes a first specifically programmed computing processor that is configured to at least perform the following operations: receiving raw Electrocardiogram (ECG) signals data from the at least one pair of ECG sensors; wherein the at least one pair of ECG sensors is positioned on the abdomen of the pregnant human subject; wherein the raw ECG signals data comprise data representative of a N number of raw ECG signals (raw N-ECG signals data) which are being acquired in real-time from the at least one pair of ECG sensors; detecting maternal heart peaks in each N-ECG signal in the N-ECG signals data; subtracting, from each of the N-ECG signal of the N-ECG signals data, a maternal ECG signal, by utilizing at least one non-linear subtraction procedure to obtain corrected ECG signals data which comprise data representative of a N number of corrected ECG signals (corrected N-ECG signals data), wherein the at least one non-linear subtraction procedure comprises: iteratively performing: i) dividing each N-ECG signal of N-ECG signals of the N-ECG signals data into a plurality of ECG signal segments, 1) wherein each ECG signal segment of the plurality of ECG signal segments corresponds to a beat interval of a full heartbeat, and 2) wherein each beat interval is automatically determined based, at least in part on automatically detecting an onset value and an offset value of each respective beat interval; ii) modifying each of the plurality of N-ECG signal segments to form a plurality of modified N-ECG signal segments, wherein the modifying is performed using at least one inverse optimization scheme based on a set of parameters, wherein values of the set of parameters are determined based on: iteratively performing: 1) defining a global template based on a standard heartbeat profile of an adult human being; 2) setting a set of tentative values for a local template for each N-ECG signal segment; and 3) utilizing at least one optimization scheme to determine an adaptive template for each N-ECG signal segment based on the local template being matched to the global template within a predetermined similarity value; and iii) eliminating the modified N-ECG segments from each of the N-ECG signals, by subtracting the adaptive template from each N-ECG signal thereby generating each corrected ECG signal; extracting raw fetal ECG signals data from the N-ECG signals data based on the corrected ECG signals data, wherein the raw fetal ECG signals data comprises a N number of fetal ECG signals (raw N-ECG fetal signals data); detecting fetal heart peaks in the N-ECG fetal signals data; calculating, based on the detected fetal heart peaks, at least one of: i) fetal heart rate, ii) fetal heart curve, iii) beat-2-beat fetal heart rate, or iv) fetal heart rate variability; and outputting a result of the calculating operation;

e. at least one second specialized computer machine, comprising: a second non-transient memory, electronically storing second particular computer executable program code; and at least one second computer processor which, when executing the second particular program code, becomes a second specifically programmed computing processor that is configured to at least perform the following operations: receiving, by at least one computer processor executing specific programmable instructions configured for the method, a plurality of Phonocardiogram (PCG) signals data inputs from a plurality of acoustic sensors; compiling a S number of a plurality of detection heartbeat (DH) inputs, comprising: i) the M number of filtered PCG inputs, detecting beat locations of beats in each of DH inputs; calculating a confidence score that describes a probability that the beats in each DH input of the plurality of DH inputs represent actual heartbeats and not a noise; dividing the plurality of DH inputs into at least two groups: i) a first group of DH inputs containing fetal heartbeats, ii) a second group of DH inputs containing maternal heartbeats; selecting, from the first group of DH inputs, at least one particular fetal DH input that contains the fetal heartbeat based on a first confidence score of the at least one particular fetal DH input; and selecting, from the second group of DH inputs, at least one particular maternal DH input that contains the maternal heartbeat, based on a second confidence score of the at least one particular maternal DH input; and f. at least one third specialized computer machine, comprising: a third non-transient memory, electronically storing third particular computer executable program code; and at least third one computer processor which, when executing the third particular program code, becomes a third specifically programmed computing processor that is configured to at least perform the following operations:
  i. receiving a calculated fetal heart rate for a plurality of time points over a particular time interval from N-ECG fetal signals data and a calculated fetal heart rate for a plurality of time points over a particular time interval from PCG inputs;
  ii. determining a first score of the calculated fetal heart rate for the plurality of time points over the particular time interval for the N-ECG fetal signals;
  iii. determining a second score of the calculated fetal heart rate for the plurality of time points over the particular time interval for the PCG inputs;
  iv. based on the calculated fetal heart rate and the first score for a plurality of time points over the particular time interval from N-ECG fetal signals data, and the calculated fetal heart rate and the second score for the plurality of time points over the particular time interval from the PCG inputs, determining a consolidated fetal heart rate and score for the plurality of time points over the particular time interval,
    wherein the consolidated fetal heart rate and score for an individual time point within the plurality of time points is determined as one of the four options selected from the group consisting of:
      1. a weighted weighted average of the calculated heart rate from the N-ECG fetal signals data and the PCG inputs for the individual time point, if the calculated heart rate from the N-ECG fetal signals data and the PCG inputs for the individual time point differs by 10 beats per minute or less, and if the scores of the calculated fetal heart rate for the individual time point for both the N-ECG fetal signals data and the PCG inputs are valid;
      2. the calculated heart rate having a lower score, if the calculated heart rate from the N-ECG fetal signals data and the PCG inputs for the individual time point differs by more than 10 beats per minute, and if the scores of the calculated fetal heart rate for the individual time point for both the N-ECG fetal signals data and the PCG inputs are valid;
      3. the calculated heart rate that has a valid score; and
      4. no consolidated fetal heart rate and score, if neither the calculated heart rate from the N-ECG fetal signals data nor the PCG inputs has the valid score;
  v. based on the consolidated heart rate and scores for the plurality of time points over the particular time interval, generating a fetal heart rate probability mesh;
  vi. based on the fetal heart rate probability mesh, generating an estimated fetal heart rate over the particular time interval,
    wherein the estimated fetal heart rate over the particular time interval is calculated based on (1) cost representing fetal heart probability mesh values at each point of the estimated fetal heart rate over the particular time interval; and (2) cost representing an overall tortuosity of the estimated fetal heart rate over the particular time interval.

2. The system of claim 1, wherein the garment comprises a belt.

3. A system for generating an estimation of fetal cardiac activity, comprising:
  a specifically programmed computer system comprising:
    at least one specialized computer machine, comprising:
    a non-transient memory, electronically storing particular computer executable program code; and at least one computer processor which, when executing the particular program code, becomes a specifically programmed computing processor that is configured to at least perform the following operations:
      i. receiving a calculated fetal heart rate for a plurality of time points over a particular time interval from a N number of fetal Electrocardiogram (ECG) signals (N-ECG fetal signals data) and a calculated fetal heart rate for a plurality of time points over a particular time interval from Phonocardiogram (PCG) outputs;
      ii. determining the score of the calculated fetal heart rate for the plurality of time points over the particular time interval for the N-ECG fetal signals;
      iii. determining the score of the calculated fetal heart rate for the plurality of time points over the particular time interval for the PCG outputs;
      iv. based on the calculated fetal heart rate and score for a plurality of time points over a particular time interval from N-ECG fetal signals data, and the calculated fetal heart rate and score for a plurality of time points over a particular time interval from PCG outputs, determining a consolidated fetal heart rate and score for the plurality of time points over the particular time interval,
        wherein the consolidated fetal heart rate and score for an individual time point within the plurality of time points is determined as one of the four options selected from the group consisting of:

a. a weighted average of the calculated heart rate from the N-ECG fetal signals data and the PCG outputs for the individual time point, if the calculated heart rate from the N-ECG fetal signals data and the PCG outputs for the individual time point differs by 10 beats per minute or less, and if the scores of the calculated fetal heart rate for the individual time point for both the N-ECG fetal signals data and the PCG outputs are valid;

b. the calculated heart rate having a lower score, if the calculated heart rate from the N-ECG fetal signals data and the PCG outputs for the individual time point differs by more than 10 beats per minute, and if the scores of the calculated fetal heart rate for the individual time point for both the N-ECG fetal signals data and the PCG outputs are valid;

c. the calculated heart rate that has a valid score; and d. no consolidated fetal heart rate and score, if neither the calculated heart rate from the N-ECG fetal signals data nor the PCG outputs has the valid score;

v. based on the consolidated heart rate and scores for the plurality of time points over the particular time interval, generating a fetal heart rate probability mesh; and vi. based on the fetal heart rate probability mesh, generating an estimated fetal heart rate over the particular time interval,
wherein the estimated fetal heart rate over the particular time interval is calculated based on (1) cost representing fetal heart probability mesh values at each point of the estimated fetal heart rate over the particular time interval; and (2) cost representing the overall tortuosity of the estimated fetal heart rate over the particular time interval.

4. The system of claim 3, wherein the cost representing fetal heart probability mesh values at each point of the estimated fetal heart rate over the particular time interval and the cost representing the overall tortuosity of the estimated fetal heart rate over the particular time interval are determined using dynamic programming.

5. The system of claim 4, wherein each value of the accumulated cost mesh is calculated as a sum of the fetal heart rate probability mesh value at that point and of the minimal path in its neighborhood in the previous step, based on:

$$E(i,j)=e(i,j)+\min(E(i-1,j-k));k=-4:4$$

wherein e is the value of the fetal heart rate probability mesh; E is the accumulated cost; i represents time; and j represents heart rate values in neighborhood of +/−4 [bpm/second].

6. The system of claim 3, wherein the cost representing fetal heart probability mesh values at each point of the estimated fetal heart rate over the particular time interval and the cost representing the overall tortuosity of the estimated fetal heart rate over the particular time interval are determined using an exhaustive search.

7. A computer implemented method comprising:
a. receiving Electrocardiogram (ECG) signals data from at least one pair of ECG sensors; wherein the at least one pair of ECG sensors is positioned on an abdomen of a pregnant human subject; wherein the ECG signals data comprise data representative of a N number of ECG signals (N-ECG signals data) which are being acquired in real-time from the at least one pair of ECG sensors; detecting maternal heart peaks in each N-ECG signal in the N-ECG signals data; subtracting, from each N-ECG signal of the N-ECG signals data, a maternal ECG signal, by utilizing at least one non-linear subtraction procedure to obtain corrected ECG signals data which comprise data representative of a N number of corrected ECG signals (corrected N-ECG signals data), wherein the at least one non-linear subtraction procedure comprises: iteratively performing: i) dividing each N-ECG signal of the N-ECG signals data into a plurality of ECG signal segments, 1) wherein each ECG signal segment of the plurality of ECG signal segments corresponds to a beat interval of a full heartbeat, and 2) wherein each beat interval is automatically determined based, at least in part on automatically detecting an onset value and an offset value of such beat interval; ii) modifying each of the plurality of N-ECG signal segments to form a plurality of modified N-ECG signal segments, wherein the modifying is performed using at least one inverse optimization scheme based on a set of parameters, wherein values of the set of parameters are determined based on: iteratively performing: 1) defining a global template based on a standard heartbeat profile of an adult human being; 2) setting a set of tentative values for a local template for each N-ECG signal segment; and 3) utilizing at least one optimization scheme to determine an adaptive template for each N-ECG signal segment based on the local template being matched to the global template within a pre-determined similarity value; and iii) eliminating the modified N-ECG segments from each of the N-ECG signals, by subtracting the adaptive template from the N-ECG signal thereby generating each corrected ECG signal; extracting fetal ECG signals data from the N-ECG signals data based on the corrected ECG signals data, wherein the fetal ECG signals data comprises a N number of fetal ECG signals (N-ECG fetal signals data); detecting fetal heart peaks in the N-ECG fetal signals data; calculating, based on the detected fetal heart peaks, at least one of: i) fetal heart rate, ii) fetal heart curve, iii) beat-2-beat fetal heart rate, or iv) fetal heart rate variability; and outputting a result of the calculating operation;

b. receiving, by at least one computer processor executing specific programmable instructions configured for the method, a plurality of Phonocardiogram (PCG) signals data inputs from a plurality of acoustic sensors; compiling, by the at least one computer processor, a S number of a plurality of detection heartbeat (DH) inputs, comprising: i) the M number of PCG inputs, detecting, by the at least one computer processor, beat locations of beats in each of the DH inputs; calculating, by the at least one computer processor, a confidence score that describes a probability that the beats in each DH input of the plurality of DH inputs represent actual heartbeats and not a noise; dividing, by the at least one computer processor, the plurality of DH inputs into at least two groups: i) a first group of DH inputs containing fetal heartbeats, ii) a second group of DH inputs containing maternal heartbeats; selecting, by the at least one computer processor, from the first group of DH inputs, at least one particular fetal DH input that contains the fetal heartbeat based on a first confidence score of the at least one particular fetal DH input; and selecting, by the at least one computer processor, from the second group of DH inputs, at least one particular maternal DH input that contains the maternal heartbeat, based on a second confidence score of the at least one particular maternal DH input; and c. performing the following operations on the results of step a and b:
  i. receiving a calculated fetal heart rate for a plurality of time points over a particular time interval from the N-ECG fetal signals data and a calculated fetal heart rate for a plurality of time points over a particular time interval the PCG outputs;
  ii. determining a first score of the calculated fetal heart rate for the plurality of time points over the particular time interval for the N-ECG fetal signals;
  iii. determining a second score of the calculated fetal heart rate for the plurality of time points over the particular time interval for the PCG inputs;
  iv. based on the calculated fetal heart rate and the first score for the plurality of time points over the particular time interval from the N-ECG fetal signals data, and the calculated fetal heart rate and the second score for the plurality of time points over the particular time interval from the PCG inputs, determining a consolidated fetal heart rate and score for the plurality of time points over the particular time interval,
    wherein the consolidated fetal heart rate and score for an individual time point within the plurality of time points is determined as one of the four options selected from the group consisting of:
    1. a weighted average of the calculated heart rate from the N-ECG fetal signals data and the PCG inputs for the individual time point, if the calculated heart rate from the N-ECG fetal signals data and the PCG inputs for the individual time point differs by 10 beats per minute or less, and if the scores of the calculated fetal heart rate for the individual time point for both the N-ECG fetal signals data and the PCG inputs are valid;
    2. the calculated heart rate having a lower score, if the calculated heart rate from the N-ECG fetal signals data and the PCG inputs for the individual time point differs by more than 10 beats per minute, and if the scores of the calculated fetal heart rate for the individual time point for both the N-ECG fetal signals data and the PCG inputs are valid;
    3. the calculated heart rate that has a valid score; and
    4. no consolidated fetal heart rate and score, if neither the calculated heart rate from the N-ECG fetal signals data nor the PCG inputs has the valid score;
  v. based on the consolidated heart rate and scores for the plurality of time points over the particular time interval, generating, by the at least one computer processor, a fetal heart rate probability mesh;
  vi. based on the fetal heart rate probability mesh, generating, by the at least one computer processor, an estimated fetal heart rate over the particular time interval,
    wherein the estimated fetal heart rate over the particular time interval is calculated based on (1) cost representing fetal heart probability mesh values at each point of the estimated fetal heart rate over the particular time interval; and (2) cost representing an overall tortuosity of the estimated fetal heart rate over the particular time interval.

8. The method of claim 7, wherein the cost representing fetal heart probability mesh values at each point of the estimated fetal heart rate over the particular time interval and the cost representing the overall tortuosity of the estimated fetal heart rate over the particular time interval are determined using dynamic programming.

9. The method of claim 8, wherein each value of the accumulated cost mesh is calculated as a sum of the fetal heart rate probability mesh value at that point and of the minimal path in its neighborhood in the previous step, based on:

$$E(i,j)=e(i,j)+\min(E(i-1,j-k));k=-4{:}4$$

wherein e is the value of the fetal heart rate probability mesh; E is the accumulated cost; i represents time; and j represents heart rate values in neighborhood of +/−4 [bpm/second].

10. The method of claim 7, wherein the cost representing fetal heart probability mesh values at each point of the estimated fetal heart rate over the particular time interval and the cost representing the overall tortuosity of the estimated fetal heart rate over the particular time interval are determined using an exhaustive search.

* * * * *